United States Patent
Bavetsias

(10) Patent No.: US 7,250,511 B2
(45) Date of Patent: Jul. 31, 2007

(54) PROCESS FOR THE PREPARATION OF CYCLOPENTA[G]QUINAZOLINE DERIVATIVES

(75) Inventor: Vassilios Bavetsias, Surrey (GB)

(73) Assignee: BTG International Limited, London (GB)

( * ) Notice: Subject to any disclaimer, the term of this patent is extended or adjusted under 35 U.S.C. 154(b) by 122 days.

(21) Appl. No.: 10/487,863

(22) PCT Filed: Aug. 30, 2002

(86) PCT No.: PCT/GB02/03967

§ 371 (c)(1), (2), (4) Date: Aug. 23, 2004

(87) PCT Pub. No.: WO03/020706

PCT Pub. Date: Mar. 13, 2003

(65) Prior Publication Data

US 2004/0266798 A1 Dec. 30, 2004

(30) Foreign Application Priority Data

Aug. 31, 2001 (GB) .................................. 0121214.1

(51) Int. Cl.
*C07D 241/36* (2006.01)
(52) U.S. Cl. ........................... 544/344; 544/1; 544/224
(58) Field of Classification Search ............... 544/1, 544/224, 344
See application file for complete search history.

(56) References Cited

U.S. PATENT DOCUMENTS 6,878,707 B2 *  4/2005  Ksander .................. 514/237.8
6,878,721 B1 *  4/2005  Cuenoud et al. ............ 514/312

FOREIGN PATENT DOCUMENTS

| WO | WO 94 11354 A1 | 5/1994 |
| WO | WO 95 30673 A1 | 11/1995 |
| WO | WO 00 50417 A1 | 8/2000 |

OTHER PUBLICATIONS

Bavetsias, V. et al; "Design and Synthesis of Cyclopenta'g!quinazoline-based antifolates as inhibitors of thymidylate synthase and potential antitumor agents"; *Journal of Medicinal Chemistry*, American Chemical Society, Wash., US, vol. 43, No. 10, 2000, pp. 1910-1926-26; XP002187697.

Melin, C. et al; "Novel cyclopenta'g!quinazoline dipeptide antifolates: Thymidylate synthase inhibitors with activity independent of the reduced folate carrier and folylpolyglutamate synthetase", *Chemistry and Biology of Peteridines and Folates*; 1997, Proceedings of the Int'l Symposium on Pteridines and Folates, 11th, Berchtesgaden, Germany; Eds. Pfleiderer, Wolfgang; Rokos, Hartmut; Publ.: Blackwell Wissenschafts-VErlag; Jun. 15-20, 1997, pp. 139-144, XP009000407.

Bavetsias, V. , et al; "Synthetis and antitumour activity of cyclopenta'g!quinazoline-based antifolates, a novel class of thymidylate synthase (TS) inhibitors"; *Chemistry and Biology of Pteridines and Folates 1997*, Proceedings of the Int'l Symposium on Pteridines and Folates, 11th, Berchtesgaden, Germany, Eds.: Pfleiderer, Wolfgang; Rokos, Hartmut; Publ.: Blackwell Wissenschafts-Verlag, Jun. 15-20, 1997, pp. 205-208, XP009000408.

Roth, K.D., et al; "Nicholas Reactions of Amines"; *Tetrahedron Letters* (1993) vol. 34, No. 18, pp. 2919-2911.

Thetl et al; *Clinical Cancer Research*, vol. 5, Nov. 1999 (Supplemental) at #566.

Jackman et al; *Proceedings of the American Association for Cancer Research*, 41, Mar. 2000 at #33.

* cited by examiner

*Primary Examiner*—James O. Wilson
*Assistant Examiner*—Paul V. Ward
(74) *Attorney, Agent, or Firm*—Nixon & Vanderhye

(57) ABSTRACT

Cyclopenta[g]quinazolines of formula (I), and esters and amides thereof may be made by reacting an ester or amide of formula (II); or a protected derivative thereof with a complex containing the $(propargyl)Co_2(CO)_6^+$ ion

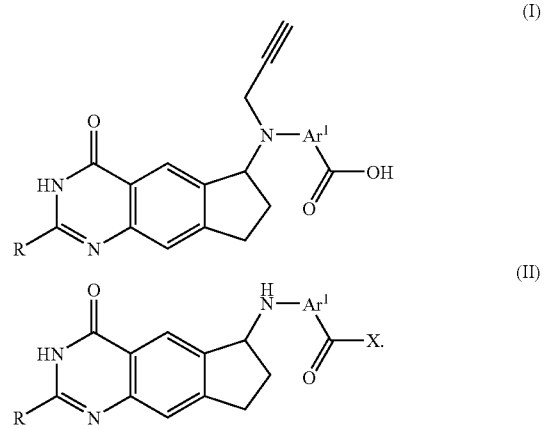

16 Claims, No Drawings

PROCESS FOR THE PREPARATION OF CYCLOPENTA[G]QUINAZOLINE DERIVATIVES

This application is the U.S. National Phase of International Application PCT/GB02/03967 filed 30 Aug. 2002, which designated the U.S.

This invention relates to a process for the preparation of certain cyclopenta[g]-quinazoline derivatives which are intermediates in the preparation of cyclopenta[g]-quinazoline derivatives which possess anti-cancer activity.

Cyclopenta[g]quinazoline derivatives which possess anti-cancer activity are disclosed in WO-A-94/11354 (British Technology Group Limited), which discloses tricyclic compounds of formula:

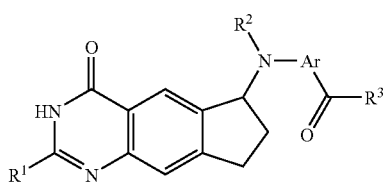

wherein $R^3$ is a group of one of the following formulae:

—NHCH(CO₂H)—A¹—Y¹—NH—A³—Y³ or $R^3$ is a N-linked naturally-occurring amino acid selected from the group consisting of L-alanine, L-leucine, L-isoleucine, L-valine and L-phenylalanine.

Further examples of such compounds are disclosed in WO-A-95/30673 (British Technology Group Limited), which discloses cyclopenta[g]quinazolines of formula:

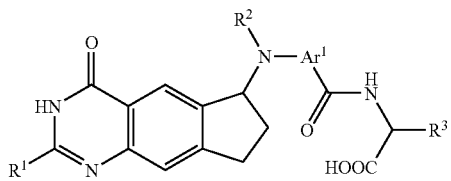

The synthesis of these cyclopenta[g]quinazoline-compounds is reported in *J. Med. Chem.*, 2000, 43, 1910-1926 (Bavetsias et al.). When $R^1$ represents a methyl group, $R^2$ a propargyl group and $Ar^1$ a 1,4-phenylene group, then 4{N-[(6RS)-2-methyl-4oxo-3,4,7,8-tetrahydro-6H-cyclopenta[g]quinazolin-6-yl]-N-(prop-2-yn-yl)amino}benzoic acid:

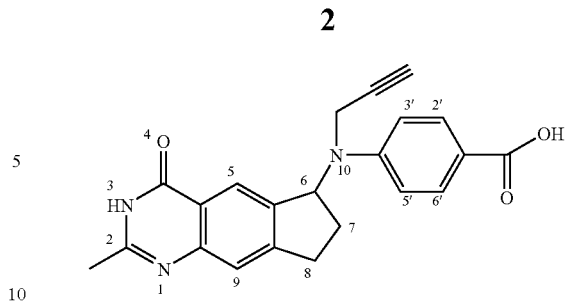

is the key intermediate for the synthesis of this class of compounds, and has been prepared from N-(4-{N-[(6RS)-2-methyl-4oxo-3,4,7,8-tetrahydro-6H-cyclopenta[g]-quinazolin-6-]-N-(prop-2-ynyl)amino}benzoyl)-L-glutamic acid by the enzymatic cleavage of its glutamyl residue, as also reported in *J. Chem. Soc., Perkin Trans.* 1, 1999, 1495 (Marriott et al.). The propargyl group in this intermediate is introduced under fairly severe conditions by using propargyl bromide and calcium carbonate in DMA [N,N-dimethylacetamide] at 100° C. This reaction is facilitated when an amide functionality is present at a position para to the $N^{10}$—H, when compared with a compound having an ester such as $CO_2Bu^t$. Therefore, this step has to be performed on a compound of formula:

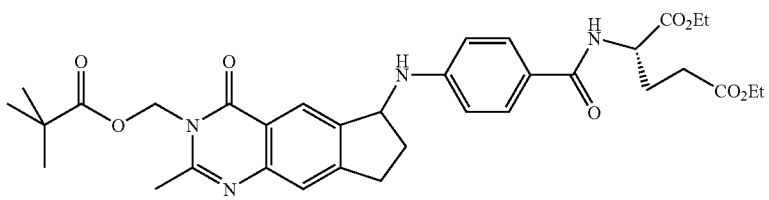

This has a glutamyl residue which has to be cleaved to generate COOH again, using the carboxypeptidase G enzyme, which is very expensive. It has in turn been made by amination of a ketone of formula:

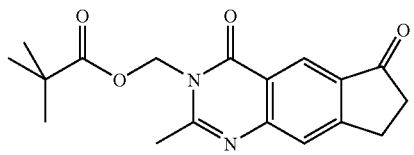

No regiospecific synthesis of this cyclopentanone is available, so the synthesis involves oxidation of the corresponding cyclopentane with tert-butyl hydroperoxide and chromium(VI) oxide in dichloromethane, and wastefully discarding the isomeric by-product:

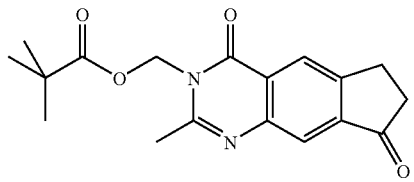

The ring-closing step is performed even earlier on in the scheme, by means of the following reaction using hydrogen peroxide and sodium hydroxide in ethanol and water at 50° C.:

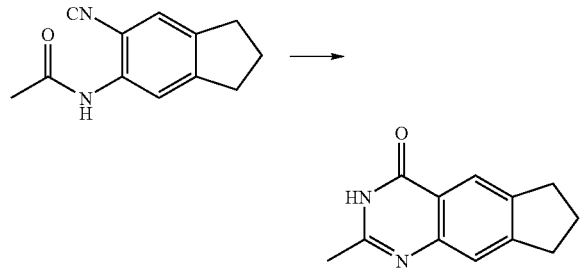

Thus the prior art might be summarised as the following main steps:

ring closure;

protection;

oxidation;

reductive amination;

propargylation;

deprotection; and enzymatic cleavage of the glutamyl residue.

We have now developed an improved route to this key intermediate in which the propargyl group is introduced in the penultimate step using the (propargyl)Co$_2$(CO)$_6^+$ complex as the electrophilic propargyl synthon. Accordingly the present invention comprises a process for the preparation of a cyclopenta[g]-quinazoline of formula (I):

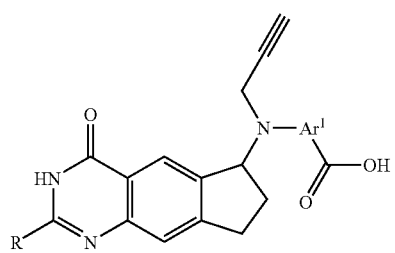

wherein:

R is hydrogen, $C_{1-4}$ alkyl, $C_{2-4}$ alkenyl, $C_{2-4}$ alkynyl, $C_{1-4}$ halogenoalkyl or $C_{1-4}$ cyanoalkyl; or R is a group $A(CH_2)_p$ where A is $R^0O$ or $R^0R^1N$ wherein $R^0$ and $R^1$ are each independently hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl, or $R^0$ and $R^1$ together with the intermediate N form a five- or six-membered heterocyclic ring and p is an integer in the range 0 to 4; and $Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy;

or an ester or amide thereof;

including the step of reacting an ester or amide of formula (II):

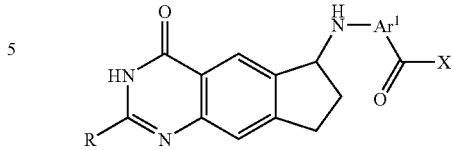

wherein R and $Ar^1$ are as defined above and X is an alkoxy, aryloxy or optionally substituted amino group;

or a protected derivative thereof;

with a complex containing the (propargyl)Co$_2$(CO)$_6^+$ ion.

The complex containing the (propargyl)Co$_2$(CO)$_6^+$ ion is preferably the tetrafluoroborate salt of formula (propargyl)Co$_2$(CO)$_6^+$BF$_4^-$. This is conveniently prepared from the corresponding hydroxy derivative HO(propargyl)Co$_2$(CO)$_6$ by reaction with a solution of HBF$_4$ in diethyl ether. It may also be prepared in situ by treatment of the corresponding hydroxy derivative HO(propargyl)Co$_2$(CO)$_6$ with a Lewis acid such as BF$_3$.Et$_2$O. The hydroxy derivative itself may be made by reacting the commercially available cobalt complex dicobalt octacarbonyl [Co$_2$(CO)$_8$] with propargyl alcohol in dichloromethane.

The reaction of the ester or amide of formula (II) with a complex containing the (propargyl)Co$_2$(CO)$_6^+$ ion is an example of the Nicholas reaction (see K.-D. Roth and U. Muller, Tetrahedron Letters 1993, 34, 2919 and K. L. Salazar and K. M. Nicholas, Tetrahedron 2000, 56, 2211). It has never been used in the context of cyclopenta[g]quinazoline derivatives, however. Reaction is conveniently performed in an anhydrous organic solvent, such as dichloromethane, in the presence of an organic base such as N,N-diisopropylethylamine at room temperature.

The reaction can be performed in an anhydrous organic solvent such as dichloromethane or dimethoxyethane (DME) in a presence of a base at temperatures ranging between −30° C. to room temperature under argon. Preferably the reaction is in anhydrous dichloromethane using N,N-diisopropylethylamine as the base and at room temperature under argon.

The use of the (propargyl)Co$_2$(CO)$_6^+$ ion gives great versatility in the synthetic route that may be used, and the concomitant milder conditions mean that there is no need to have a glutamate group at the right-hand side of the molecule before reaction takes place, as in the prior art process. Thus the reaction can be done using an ester as the compound of formula (II). Conveniently the reaction may be performed on the tert-butyl ester of formula (IIA):

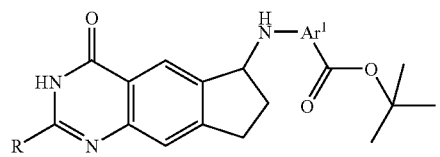

The ester functionality can be hydrolysed to the corresponding acid under standard conditions, e.g. with trifluoroacetic acid in the case of the tert-butyl ester of formula (IIA).

The ring-closing reaction to create the core of the structure can be performed at a late stage in the reaction sequence. It can be achieved via the step:

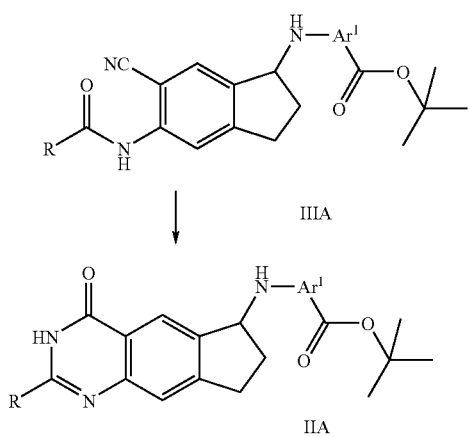

IIIA

↓

IIA

This means the reaction scheme is significantly different from the published one. It also has the advantage that the oxidation step to introduce the ketone group (which is then reacted further) is done early in the scheme. This step produces two positional isomers:

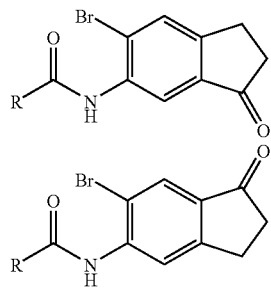

and the first of these may be discarded so there is no need to use double the amount of reagents later on. This oxo functionality, required for the formation of the $C^6$—$N^{10}$ bond via a reductive amination reaction, is introduced in the initial steps of the synthesis, whereas the cyclopenta[g]quinazoline ring is constructed after the formation of the $C^6$—N bond, making this route simpler and more flexible. This compares favourably with the prior art process, where the compound:

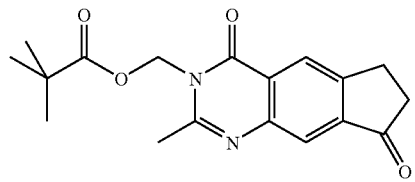

had to be discarded in the later stages of the synthesis.

Thus in a further aspect of the invention there is provided a process for the preparation of a cyclopenta[g]quinazoline of formula (I) including the step of ring-closing a compound of formula (III):

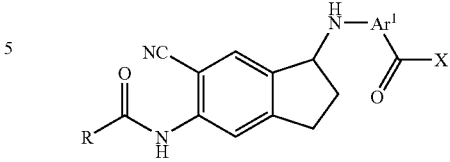

(III)

wherein R and $Ar^1$ are as defined above and X is an alkoxy, aryloxy or optionally substituted amino group;
or a protected derivative thereof;
to form a compound of formula (II) as defined above;
or a protected derivative thereof.

Various reaction conditions are possible. Acidic conditions might be used (acetic acid/sulfuric acid, 100° C., stirring for a few hours) as reported by R. H. Lemus et al., *J. Org. Chem.* 1992, 57, 5649-5660) for the preparation of quinazolinones-4-ones from o-amidobenzamides. The use of hydrogen peroxide in basic conditions is however preferred. For example, conditions similar to those used to make quinazolin-4-ones from ortho-amidobenzonitriles with urea-hydrogen peroxide, water/acetone and potassium carbonate are possible (see B. P. Bandgar, *Synth. Communications,* 1997 27(12), 2065-2068). Reaction is conveniently performed using hydrogen peroxide and sodium hydroxide in ethanol and water at elevated temperature, around 55° C.

The sequence of steps, by contrast to the prior art sequence discussed above, is now:
protection (optional);
oxidation;
reductive amination;
ring closure;
propargylation; and
deprotection (optional).

In this specification the terms "alkyl", "alkenyl", "alkynyl" and "alkylene" include both straight and branched chain groups but references to individual alkyl or alkylene groups, such as "propyl", are specific for the straight chain group only. An analogous convention applies to other generic terms. Moreover, the numbering system used for the cyclopenta[g]quinazoline nucleus is the conventional one as shown below:

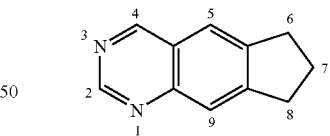

It will be observed that a cyclopenta[g]quinazoline of the invention contains at least one asymmetric carbon atom [present at the point of attachment of the group amino group to the tricyclic ring system] and can therefore exist in racemic and optically active forms. It is to be understood that this invention encompasses both racemic and optically active forms of Cyclopenta[g]quinazolines, it being a matter of common general knowledge how such optically active forms may be obtained by stereospecific synthesis or by separation of a mixture of isomeric compounds. It will be appreciated that one isomer may be of more interest than another due to the nature of the activity which the final product exhibits or due to superior physical properties, for example aqueous solubility.

It is also to be understood that a cyclopenta[g]quinazoline of the formula (I) may exhibit the phenomenon of tautomerism and that the formulae shown in this specification represent only one of the possible tautomeric forms. It is to be understood therefore that the invention is not limited merely to any one tautomeric form which is illustrated. For example, in the case where R is simply hydroxyl (in other words a group $A(CH_2)_p$ where A is HO and p is 0), the a cyclopenta[g]-quinazoline of formula (I) is likely to exist in its keto tautomeric form, i.e. 2-oxo, of formula (IA):

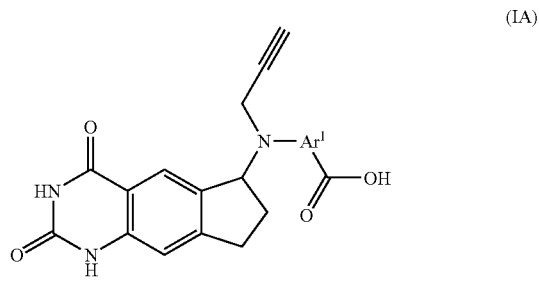

(IA)

and the intermediates are similarly likely to exist in this form.

It is also to be understood that certain cyclopenta[g] quinazolines of the formula (I) can exist in solvated as well as unsolvated forms such as, for example, hydrated forms.

A suitable value for R, $R^0$ or $R^1$ when it is $C_{1-4}$ alkyl, or for a $C_{1-4}$ alkyl substituent which may be present on $Ar^1$, is, for example, methyl, ethyl, propyl or isopropyl.

A suitable value for R when it is $C_{1-4}$ alkoxy, or for a $C_{1-4}$ alkoxy substituent which may be present on $Ar^1$, is, for example, methoxy, ethoxy, propoxy, isopropoxy or butoxy.

A suitable value for a halogeno substituent which may be present on $Ar^1$ is, for example, fluoro, chloro or bromo.

A suitable value for R when it is $C_{2-4}$ alkenyl is, for example, vinyl, prop-2-enyl, but-2-enyl, but-3-enyl or 2-methylprop-2-enyl; and when it is $C_{2-4}$ alkynyl is, for example, ethynyl, prop-2-ynyl or but-3-ynyl. A suitable value for $R^0$ or $R^1$ when it is $C_{3-4}$ alkenyl is, for example, prop-2-enyl, but-2-enyl, but-3-enyl or 2-methylprop-2-enyl; and when it is $C_{3-4}$ alkynyl is, for example, prop-2-ynyl or but-3-ynyl.

A suitable value for R when it is $C_{1-4}$ halogenoalkyl is, for example, fluoromethyl, difluoromethyl, trifluoromethyl or 2-fluoroethyl.

A suitable value for $R^0$ or $R^1$ when it is $C_{2-4}$ hydroxyalkyl is, for example, 2-hydroxyethyl or 3-hydroxypropyl; when it is $C_{2-4}$ halogenoalkyl is, for example, 2-fluoroethyl, 2-chloroethyl, 2-bromoethyl, 3-fluoropropyl, 3-chloropropyl or 3-bromopropyl. A suitable value for R, $R^0$ or $R^1$ when it is $C_{1-4}$ cyanoalkyl is, for example, cyanomethyl, 2-cyanoethyl or 3-cyanopropyl.

When $R^0$ and $R^1$ together with the intermediate N form a five- or six-membered heterocyclic ring, this may bear substituents, but the ring is preferably an unsubstituted saturated ring such as pyrrolidine or piperidine.

A suitable value for $Ar^1$ when it is phenylene is, for example, 1,3- or 1,4-phenylene, especially 1,4-phenylene.

A suitable value for $Ar^1$ when it is thiophenediyl is, for example, thiophene-2,4-diyl or thiophene-2,5-diyl; when it is thiazolediyl is, for example thiazole-2,4-diyl or thiazole-2,5-diyl; when it is pyridinediyl is, for example, pyridine-2,4-diyl, pyridine-2,5-diyl, pyridine-2,6-diyl or pyridine-3,5-diyl; and when it is pyrimidinediyl is, for example, pyrimidine-2,4-diyl, pyrimidine-2,5-diyl or pyrimidine-4,6-diyl.

As indicated, $Ar^1$ may carry one or two substituents. A preferred level of substitution in $Ar^1$, where substitution is present, is either two substituents or especially one substituent; and the one or two substituents may conveniently be at positions adjacent to the atom bonded to the group —COOH, halogeno substituents such as fluoro being preferred.

A suitable ester form of a Cyclopenta[g]quinazoline of the invention is, for example, an ester with an aliphatic alcohol of up to 6 carbon atoms, for example a methyl, ethyl or tert-butyl ester. The ester should be stable to the conditions used for the ring-closure reaction. A suitable amide is any of the compounds disclosed in WO-A-94/11354 or WO-A-95/30673 (8British Technology Group Limited). The contents of these earlier documents are thus incorporated herein by way of reference. Although the process of the invention obviates the need to have to use a compound having a glutamyl residue which has to be cleaved to generate COOH again, using the expensive carboxypeptidase G enzyme, we have found that the reaction of a protected derivative of a compound of formula (IV):

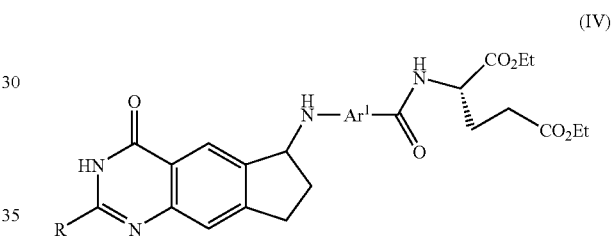

(IV)

may likewise be reacted with a complex containing the (propargyl)$Co_2(CO)_6^+$ ion according to the present invention. With suitable protection, any ester or amide may be used.

A protecting group is conveniently employed where other functional groups are present which could interfere with the reaction (propargyl)$Co_2(CO)_6^+$ ion. For example, where a hydroxyl group is present, such as the compound where R is a group $A(CH_2)_p$ where A is HO, a hydroxyl-protecting group may be employed which prevents the —OH from reacting. The hydroxyl group can be protected as the methyl ether—the methyl group can be removed by a Lewis acid such as $BBr_3$. Other suitable ether protecting groups are methoxymethyl (MOM), which can be removed with a Lewis acid such as $BF_3.Et_2O$. The tert-butyldimethylsilyl group could also be used—this can be cleaved with $Bu_4N^+$ $F^-$. Preferably a group such as 2,2-dimethyl-propionyl, sterically hindered but easily removed by hydrolysis, is used.

When an amino group is present in addition to the one in the $N^{10}$ position, this may be protected with conventionally employed peptide chemistry N-terminal protecting groups. A suitable protecting group for the amino functionality is benzyl-oxycarbonyl, which can be removed by catalytic hydrolysis, a Lewis acid such as $BBr_3$ or 30% HBr in acetic acid. The butoxycarbonyl group (BOC) can also be used—this can be removed with trifluoroacetic acid (TFA). The triphenylmethyl group (Tr) can also be used—this can be removed with 80% acetic acid or TFA. A group such as 2,2-dimethylpropionyl could also be a suitable group and could be removed under alkaline hydrolysis conditions.

A preferred cyclopenta[g]quinazoline which may be made according to the invention has the formula (I) wherein R is $C_{1-4}$ alkyl, $C_{2-4}$ alkenyl, $C_{2-4}$ alkynyl or a group $A(CH_2)_p$, wherein $R^0$ and $R^1$ are each independently hydrogen or $C_{1-4}$ alkyl, especially methyl; and wherein $Ar^1$ is 1,4-phenylene which may optionally bear one or two substituents selected from the group consisting of chloro and especially fluoro, thiophene-2,5-diyl, thiazole-2,5-diyl or pyridine-2,5-diyl.

A preferred value for p is 1.

An especially preferred cyclopenta[g]quinazoline has the formula (I) wherein R is methyl, hydroxymethyl or methoxymethyl; and $Ar^1$ is 1,4-phenylene or 2-fluoro-1,4-phenylene.

Specific particularly preferred cyclopenta[g]quinazolines of formula (I) are:

4-{N-[(6RS)-2-methyl-4-oxo-3,4,7,8-tetrahydro-6H-cyclopenta[g]quinazolin-6-yl]-N-(prop-2-ynyl)amino}benzoic acid;

4-{N-[(6RS)-2-methoxymethyl-4-oxo-3,4,7,8-tetrahydro-6H-cyclopenta[g]-quinazolin-6-yl]-N-(prop-2-ynyl) amino}benzoic acid;

4-[N-((6RS)-2-(hydroxymethyl)-4-oxo-3,4,7,8-tetrahydro-6H-cyclopenta[g]-quinazolin-6-yl)-N-(prop-2-ynyl) amino]benzoic acid;

or esters or amides thereof.

Although the compounds of the present invention can exist as a mixture of stereoisomers it is preferred that they are resolved into one optically active isomeric form.

The compound of formula (III) and its halo precursor are key intermediates in the preferred ring-closing process. Thus in a further aspect of the invention there is provided a compound of formula (V):

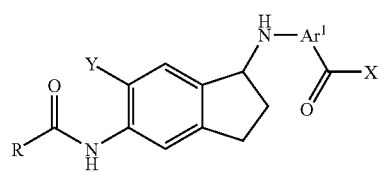

wherein:

R is hydrogen, $C_{1-4}$ alkyl, $C_{2-4}$ alkenyl, $C_{2-4}$ alkynyl, $C_{1-4}$ halogenoalkyl or $C_{1-4}$ cyanoalkyl; or R is a group $A(CH_2)_p$ where A is $R^0O$ or $R^0R^1N$ wherein $R^0$ and $R^1$ are each independently hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl, or $R^0$ and $R^1$ together with the intermediate N form a five- or six-membered heterocyclic ring and p is an integer in the range 0 to 4; and $Ar^1$ is phenylene, thiophenediyl, thiazolediyl, pyridinediyl or pyrimidinediyl which may optionally bear one or two substituents selected from halogeno, hydroxy, amino, nitro, cyano, trifluoromethyl, $C_{1-4}$ alkyl and $C_{1-4}$ alkoxy;

X is an alkoxy, aryloxy or optionally substituted amino group;

Y is CN or a leaving group selected from Br, Cl and I; or a protected derivative thereof Preferably X is a residue of an aliphatic alcohol of up to 6 carbon.

Preferably R is $C_{1-4}$ alkyl, $C_{2-4}$ alkenyl, $C_{2-4}$ alkynyl or a group $A(CH_2)_p$, wherein $R^0$ and $R^1$ are each independently hydrogen or $C_{1-4}$ alkyl, especially methyl; and $Ar^1$ is 1,4-phenylene which may optionally bear one or two substituents selected from the group consisting of chloro and especially fluoro, thiophene-2,5-diyl, thiazole-2,5-diyl or pyridine-2,5-diyl. Preferably p is 1.

The present invention may be used to prepare a cyclopenta[g]quinazoline of formula (VI):

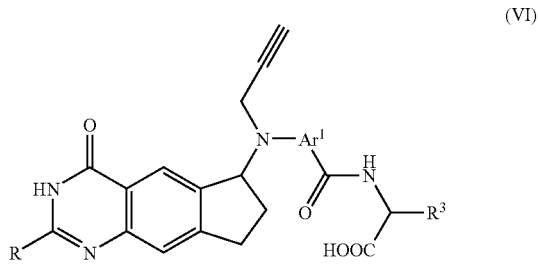

wherein A and $Ar^1$ are as defined above, and $R^3$ is a group of the formula:

$$-A^5-CON(R)CH(Y^4)Y^5$$

in which $A^5$ is a $C_{1-6}$ alkylene group and R is hydrogen, $C_{1-4}$ alkyl, $C_{3-4}$ alkenyl or $C_{3-4}$ alkynyl;

$Y^4$ is carboxy, tetrazol-5-yl, N-($C_{1-4}$ alkylsulfonyl)carbamoyl, N-(phenyl-sulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl; and $Y^5$ is the residue of a naturally occurring amino acid $NH_2CH(CO_2H)Y^5$; or $Y^5$ is a group of the formula:

$$-A^4-CO_2H$$

in which $A^4$ is a $C_{2-6}$ alkylene group; or $Y^5$ is a group of the formula:

$$-A^6-Ar^3-A^7-Y^6$$

in which $A^6$ is a bond between the α-carbon atom of the group $-A^5-CON(R)CH(Y^4)-$ and $Ar^3$ or is a $C_{1-2}$ alkylene group;

$Ar^3$ is phenylene, tetrazolediyl, thiophenediyl, thiazolediyl, pyridinediyl or pyrimidinediyl which in the case of phenylene may optionally bear one or two substituents on the ring selected from halogeno, nitro, $C_{1-4}$ alkyl and $C_{1-4}$ alkoxy;

$A^7$ is a $C_{1-3}$ alkylene or $C_{2-3}$ alkenylene group; and $Y^6$ is carboxy, tetrazol-5-yl, N-($C_{1-4}$ alkylsulfonyl)carbamoyl, N-(phenyl-sulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl;

the compound (VI) optionally being in the form of a pharmaceutically acceptable salt or ester.

The Cyclopenta[g]quinazoline of formula (VI) is produced from the corresponding compound of formula (I) by known methods such as disclosed in WO-A-94/11354 and WO-A-95/30673. Preferred values for the various substituents are as expressed in WO-A-94/11354 and WO-A-95/30673.

The invention is illustrated by the following Examples. Thin layer chromatography (TLC) was performed on pre-coated sheets of silica 60F$_{254}$ (Merck Art 5735) visualised under UV light. Merck silica 60 (Art 15111) was used in low-pressure column chromatography. Petrol refers to light petroleum (b.p. 60-80° C.). Electrospray ionisation (ESI) mass spectra were recorded using a TSQ 700 triple quadrupole mass spectrometer (Finnigan MAT) fitted with an electrospray ionisation source (Analytica). Proton NMR spectra were recorded using a Bruker AC250 spectrometer at 250 MHz. Field strengths are expressed in units of δ (ppm) relative to tetramethylsilane, and peak multiplicities are designated as follows: s, singlet; d, doublet; dd, doublet of doublets; dm, doublet of multiplets; t, triplet; q, quartet, br s, broad singlet, m, multiplet. Melting points were determined on a Kofler block and are uncorrected. Elemental analyses were determined by C.H.N. Analysis Ltd., Leicester, UK.

EXAMPLE 1 synthesis of 4{N-[(6RS)-2-Methyl-4-oxo-3,4,7,8-tetrahydro-6H-cyclopenta[g]quinazolin-6-yl]-N-(prop-2-ynyl)amino}benzoic acid

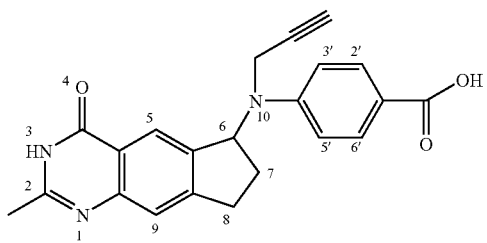

Synthesis is as in Scheme 1.

5-Acetamido-6-bromoindan-1-one 6

This compound was prepared as described in *J. Med. Chem.*, 1995, 38, 4897 (Li et al.). To a solution of 5-acetamido-6-bromoindan (5.74 g, 22.6 mmol) in glacial acetic acid (52 ml) heated at 55° C. was dropwise added a solution of CrO$_3$ (9.04 g, 90.4 mmol) in aqueous glacial acetic acid, (52 ml v/v 1:1) over a 20 min period. The dark red mixture was then stirred at this temperature for 20 min. The reaction mixture was cooled in an ice-bath, then propan-2-ol (15 ml) was added and the mixture was stirred at this temperature for 10 min before being concentrated in vacuo. The black residue was broken up with a spatula with the aid of water and then partitioned between water (200 ml) and ethyl acetate (150 ml). The aqueous layer was extracted with more ethyl acetate (2×150 ml); the combined extracts were dried (Na$_2$SO$_4$), and concentrated in vacuo to give a white residue. Purification by column chromatography using a gradient of ethyl acetate in dichloromethane (10 to 20%) afforded in order of elution:

a. 5-acetamido-6-bromoindan-1-one as a white solid which was further purified by trituration with ethyl acetate/hexanes (1:4, v/v): 2.60 g (43%), m.p. 162-164° C. (Found: C, 49.18; H, 3.65; N, 5.13; Br, 29.89; C$_{11}$H$_{10}$BrNO$_2$ requires C, 49.28; H, 3.76; N, 5.22; Br, 29.80%); δ$_H$ (CDCl$_3$) 2.30 (1H, s, Me), 2.71 (2H, m 2-H), 3.11 (2H, t, J 5.6, 3-H), 7.93 (1H, br s, CONH), 7.94, 8.60 (each 1H, s, 4-H, 7-H); m/z (ESI) 268, 270 {(M+H)$^+$, 100%, 95% respectively, bromine isotopic pattern}, 226 (25).

b. 5-acetamido-6-bromoindan-3-one as a white solid which was further purified by trituration with ethyl acetate/hexanes (1:4, v/v): 0.45 g, (8%), m.p. 219-220° C. (Found: C, 49.24; H, 3.67; N, 5.12; Br, 29.73; C$_{11}$H$_{10}$BrNO$_2$ requires C, 49.28; H, 3.76; N, 5.22; Br, 29.80%); δ$_H$ (CDCl$_3$) 2.26 (3H, s, Me), 2.71 (2H, m, 2-H), 3.10 (2H, t, J 5.6, 1-H), 7.60 (1H, br s, CONH), 7.72, 8.62 (each 1H, s, 4-H, 7-H); m/z (ESI) 268, 270 {(M+H)$^+$, 100%, 95% respectively, bromine isotopic pattern}, 188 (90).

tert-Butyl 4-[N-(5-acetamido-6-bromoindan-1-yl)amino]benzoate 7

Method A: To a flask containing 5-acetamido-6-bromoindan-1-one (6) (0.900 g, 3.36 mmol), 4-toluenesulfonic acid monohydrate (0.045 g), and tert-butyl 4-aminobenzoate (0.972 g, 5.04 mmol) was added 1,2-dimethoxyethane (dried by distillation over CaH$_2$; 48 ml). An azeotropic distillation apparatus (Aldrich) containing molecular sieves (3A) was fitted to the reaction flask that was placed in an oil bath preheated to 60° C. The temperature was raised to 110° C. and stirring was continued at this temperature for 7 h under argon. The reaction mixture was then allowed to cool to room temperature, then a solution of sodium cyanoborohydride (0.336 g) in anhydrous methanol (11 ml) was added followed immediately by acetic acid (0.6 ml). The black reaction mixture was stirred at room temperature for 24 h under argon; then partitioned between ethyl acetate (170 ml) and saturated aqueous sodium bicarbonate (100 ml). The aqueous layer was extracted with more ethyl acetate (2×100 ml); the organic extracts were combined, dried (MgSO$_4$) and concentrated in vacuo to leave a dark oily residue. Purification by column chromatography on elution with ethyl acetate/hexane (1:1, v/v) afforded the title compound 7 as a white solid: 0.520 g (35%).

Method B: To a nearly clear solution of 5-acetamido-6-bromoindan-1-one (0.964 g, 3.60 mmol) in anhydrous methanol (70 ml) was added tert-butyl 4-aminobenzoate (0.733 g, 3.8 mmol) followed by decaborane (0.130 g, 1.08 mmol); a clear solution had obtained after stirring for approximately 0.5 h. The reaction mixture was stirred at room temperature overnight before being concentrated in vacuo. Purification by column chromatography, on elution with a gradient of ethyl acetate in hexane (35 to 40%), afforded a gummy residue which was further purified by trituration with dichloromethane/hexane (1:4, v/v). The title compound 7 was obtained as a white solid: 1.32 g (81%) m.p. 153° C. (Found: C, 59.36; H, 5.62; N, 6.31; Br, 17.96; C$_{11}$H$_{10}$BrNO$_2$ requires C, 59.33; H, 5.66; N, 6.29; Br, 17.94%); δ$_H$ (CDCl$_3$) 1.57 (9H, s, C(CH$_3$)$_3$), 2.25 (3H, s, Me), 1.91, 2.63 (each 1H, m, 2-H), 2.95 (2H, m, 3-H), 5.03 (1H, t, J 6.60, 1-H), 6.64 (2H, d, J 8.75, 3',5'-H), 7.60 (1H, br s, CONH), 7.49, 8.25 (each 1H, s, 4-H, 7-H), 7.85 (2H, d, J 8.75, 2',6'-H); m/z )ESI) 467, 469 {(M+Na)$^+$, 100%, 95% respectively, bromine isotopic pattern}, 252, 254 (35).

tert-Butyl 4-[N-(5-acetamido-6-cyanoindan-1-yl)amino]benzoate 8

To a solution of 7 (1.170 g, 2.62 mmol) in NMP (13 ml) was added copper(I) cyanide (0.400 g, 4.70 mmol). The reaction mixture was placed in an oil-bath preheated to 140°

C. and stirred at this temperature for 1 h and 40 min. The reaction mixture was allowed to cool to room temperature, then poured into a mixture of aqueous ammonia (d=0.88, 12 ml) and ice (~34 ml) and the resulting brown mixture was stirred at room temperature for ~10 min. The brown solid was collected by filtration washed with plenty of water, then suspended in dichloromethane (100 ml). The mixture was stirred at room temperature for 10 min, dried (MgSO$_4$), and concentrated in vacuo. Purification by column chromatography, on elution with 35% ethyl acetate in hexane, afforded a crispy solid that was reprecipitated from ethyl acetate/hexane. The title compound 8 was obtained as a white solid: 0.714 g, (70%) m.p. 173-174° C. (Found: C, 70.35; H, 6.44; N, 10.62; $C_{23}H_{25}N_3O_3$ requires C, 70.57; H, 6.44; N, 10.73%); $\delta_H$ (CDCl$_3$) 1.58 (9H, s, C(CH$_3$)$_3$), 2.28 (3H, s, Me), 1.96, 2.67 (each 1H, m, 2-H), 3.04 (2H, m, 3-H), 4.23 (1H, d, J 8.31, N—H), 5.06 (1H, q, J 7.50, 1-H), 6.65 (2H, d, J 8.75, 3',5'-H), 7.60 (1H, br s, CONH), 7.54, 8.32 (each 1H, s, 4-H, 7-H), 7.87 (2H, d, J 8.75, 2',6'-H); m/z (ESI) 783 {(2M+H)$^+$, 100%,}, 414 {(M+Na)$^+$, 55%}, 199 (15).

tert-Butyl 4-{N-[(6RS)-2-Methyl4-oxo-3,4,7,8-tetrahydro-6H-cyclopenta-[g]quinazolin-6-yl]amino}benzoate 9

A mixture of 8 (1.33 g, 3.40 mmol), ethanol (15 ml), and water (3.1 ml) was cooled in an ice-bath, then 30% aqueous H$_2$O$_2$ solution (2.8 ml) was added followed by granulated sodium hydroxide pellets (0.230 g, 5.78 mmol). The reaction mixture was stirred at ~0° C. for 10 min, then it was placed in an oil bath preheated to 55° C. and stirred at this temperature for 40 min. The reaction mixture was allowed to cool to room temperature, then the solvents were removed in vacuo and the residue was suspended in water (~40 ml). The pH of this mixture was adjusted to ~5 with 1N hydrochloric acid. The white precipitate was collected by filtration, washed with water, dried in vacuo over P$_2$O$_5$, then it was triturated with ether, collected by filtration and dried in vacuo. The title compound 9 was obtained as a white solid 1.11 g (83%), m.p. 277-281° C. (it melts with decomposition), (Found: C, 70.22; H, 6.43; N, 10.65; $C_{23}H_{25}N_3O_3$ requires C, 70.57; H, 6.44; N, 10.73%); $\delta_H$ ((CD$_3$)$_2$SO) 1.50 (9H, s, C(CH$_3$)$_3$), 2.31 (3H, s, Me), 1.87, 2.55 (each 1H, m, 7-H), 2.97 (2H, m, 8-H), 5.15 (1H, q, J 7.50, 6-H), 6.77 (2H, d, J 8.6, 3',5'-H), 6.91 (1H, d, J 8.70, N$^{10}$—H), 7.44, 7.87 (each 1H, s, 5-H, 9-H), 7.66 (2H, d, J 8.75, 2',6'-H); m/z ESI) 783 {(2M+H)$^+$, 100%}, 392 {(N+H)$^+$, 30%}, 199 (90).

Dicobalthexacarbonyl propargyl complex 11

This is a known compound (K.-D. Roth and U. Muller, *Tetrahedron Letters* 1993, 34, 2919) and in this study was prepared according to Nicholas' methodology (K. L. Salazar and K. M. Nicholas, *Tetrahedron* 2000, 56, 2211). To a round bottom flask charged with Co$_2$(CO)$_8$ (5.12 g, 15.0 mmol) under argon in a well ventilated hood was added anhydrous dichloromethane (170 ml) followed by a solution of propargyl alcohol (0.840 g, 15.0 mmol) in anhydrous dichloromethane (20 ml). The deep red reaction mixture was stirred at room temperature for 7 h under argon, then it was filtered through a thin layer of neutral alumina. The filtrate was concentrated in vacuo to give a red residue. Purification by column chromatography, on elution with 40% diethyl ether in hexane, afforded the title compound 11 as a red solid 4.10 g (80%); $\delta_H$ (CDCl$_3$) 1.83 (1H, t, J 6.0, OH), 4.80 (2H, d, J 6.0, CH$_2$), 6.08 (1H, s, C—H).

Propargyl)Co$_2$(CO)$_6$$^+$BF$_4$$^-$12

This is a known compound (K.-D. Roth and U. Muller, *Tetrehedron Letters* 1993, 34, 2919) and in this study was prepared according to Nicholas' methodology (K. L. Salazar and K. M. Nicholas, *Tetrahedron* 2000, 56, 2211). To a round bottom flask charged with the dicobalthexacarbonyl complex 11 (1.60 g, 4.7 mmol) under argon was added (syringed via a septum) propionic acid (2.2 ml). The reaction mixture was cooled to −20° C. and then a solution of HBF4 in diethyl ether (54% w/w, 2.05 ml) was slowly syringed into the reaction mixture via a septum. The reaction mixture was stirred at −20° C. for 40 min, then cooled diethyl ether (50 ml) was added. Trituration afforded a red precipitate that was collected by filtration, washed with plenty of dry diethyl ether and dried in vacuo over P$_2$O$_5$: 1.71 g (90%). This was immediately used in the next reaction without any further purification.

tert-Butyl 4-{N-[(6RS)-2-Methyl-4-oxo-3,4,7,8-tetrahydro-6H-cyclopenta-[g]quinazolin-6-yl]-N-(prop-2-ynyl)amino}benzoate 14

To a round-bottomed flask containing the tetrafluoroborate salt 12 (1.44 g, 3.5 mmol) was added anhydrous dichloromethane (dried by distillation over P$_2$O$_5$; 100 ml). The nearly clear red dark solution was stirred at room temperature for few minutes under argon, then 9 (1.04 g, 2.66 mmol) was added in one portion; a clear solution had obtained after approximately 2 min. Stirring was continued at this temperature for 5 min then diisopropylethylamine (0.92 ml, 5.32 mmol) was added and the reaction mixture was stirred at room temperature for 45 min under argon. The reaction mixture was partitioned between ethyl acetate (300 ml) and brine (120 ml). The organic layer was washed with 10% aqueous citric acid (100 ml), brine (100 ml), dried (Na$_2$SO$_4$), and concentrated in vacuo. Purification by column chromatography, on gradient elution with ethyl acetate in dichloromethane (60 to 70%/o), gave 13 as a red solid 1.45 g (76%), m.p. >150° C. (it decomposes, red crystals turn black); $\delta_H$ (CDCl$_3$) 1.58 (9H, s, C(CH$_3$)$_3$), 2.53 (3H, s, 2-Me), 2.32, 2.60 (each 1H, m, 7-H), 3.05, 3.20 (each 1H, m, 8-H), 4.55 (2H, ABq, J 17.2, N$^{10}$—CH$_2$), 5.63 (1H, t, J 8.6, 6-H), 5.96 (1H, s, propargyl complex C—H, 6.93 (2H, d, J 8.9, 3',5'-H), 7.58, 8.00 (each 1H, s, 5-H, 9-H), 7.90 (2H, d, J 8.9, 2',6'-H), 10.58 (1H, s, N$^3$—H); m/z (ESI) 716 {(M+H)$^+$, 80%}, 231 (100), 199 (70). To a solution of this complex (1.40 g, 1.96 mmol) in ethanol (200 ml) was added Fe(NO$_3$)$_3$ (26 g). The clear solution was stirred at room temperature for 10 min then a second portion of Fe(NO$_3$)$_3$ (~15 g) was added. The reaction mixture was stirred at room temperature for a longer 10 min then a final portion of Fe(NO$_3$)$_3$ (~10 g) was added; the nearly clear solution was turned into a dark red mixture. Stirring was continued at room temperature for an extra 15 min, then the reaction mixture was partitioned between ethyl acetate (700 ml) and dilute brine (200 ml). The organic (not clear) layer was washed with more brine (3×150 ml), dried (Na$_2$SO$_4$), and concentrated in vacuo to leave a brown solid. Purification by column chromatography, on elution with 5% methanol in chloroform, afforded a solid. Trituration with dichloromethane/hexane gave the title compound 14 as an off white solid, 0.565 g (67%), m.p. 244-246° C.; (Found: C, 72.60; H, 6.37; N, 9.67; $C_{26}H_{27}N_3O_3$ requires C, 72.71; H, 6.34; N, 9.78%); $\delta_H$ ((CD$_3$)$_2$SO) 1.50 (9H, s, C(CH$_3$)$_3$), 2.32 (3H, s, 2-Me), 2.18, 2.55 (obscured by the DMSO peak) (each 1H, m, 7-H), 2.97 (1H, m, 8-H), 3.14 (2H, m, C≡CH, 8-H), 3.96 (2H, ABq, J 18.1, CH$_2$C≡C), 5.75 (1H, t, J 8.2, 6-H), 6.98 (2H, d, J 9.5, 3', 5'-H), 7.48, 7.76 (each 1H, s, 5-H, 9-H), 7.74 (2H, d, J 8.7, 2', 6'-H); 12.11(1H, s, N$^3$—H); m/z (ES) 430 {(M+H)$^+$, 90%}, 374 {(M−Bu$^t$)$^+$, 55%}, 231 (100), 199 (60).

N-[(6RS)-2-Methyl-4-oxo-3,4,7,8-tetrahydro-6H-cyclopenta[g]quinazolin-6-yl]-N-(prop-2-ynyl)amino}benzoic acid 3

A solution of 14 (0.245 g, 0.57 mmol) in dichloromethane (2 ml) and trifluoroacetic acid (10 ml) was stirred at room temperature for 1.5 hours, then the solvents were removed in vacuo. The residue was triturated with diethyl ether and the precipitate was collected by filtration, washed with diethyl ether and dried in vacuo over P$_2$O$_5$ to afford the title compound as the trifluoroacetate salt (0.255 g). Part of this material (0.067 g) was suspended in water (6 ml), and the pH was adjusted to ~12 with 1N aqueous sodium hydroxide. The pH of the clear solution was adjusted to ~4 with 1N aqueous hydrochloric acid. The white precipitate was collected by filtration, washed with water and dried in vacuo over P$_2$O$_5$ to afford the title compound 3 as a white solid (0.040 g) m.p. 305-307° C.; (Found: C, 68.65; H, 4.97; N, 10.87; C$_{22}$H$_{19}$N$_3$O$_3$ 0.6H$_2$O requires C, 68.78; H, 5.29; N, 10.93%); $\delta_H$ ((CD$_3$)$_2$SO) 2.33 (3H, s, 2-Me), 2.24, 2.50 (obscured by the DMSO peak) (each 1H, m, 7-H), 2.97 (1H; m, 8-H), 3.20 (1H, m (obscured by H$_2$O peak), 8-H), 3.13 (1H, s, C≡CH), 3.96 (2H, ABq, J 19.0, CH$_2$C≡C), 5.75 (1H, t, J 8.3, 6-H), 7.01 (2H, d, J 9.0, 3', 5'-H), 7.48, 7.78 (each 1H, s, 5-H, 9-H), 7.80 (2H, d, J 9.4, 2', 6'-H); 12.11(1H, s, N$^3$—H); m/z (ESI) 747 {(2M+H)$^+$, 100%}, 374 {(M+H)$^+$, 70%}, 199 (20%).

EXAMPLE 2 synthesis of N-{N-{4-[N-((6RS)-2-Methoxymethyl4oxo-3,4,7,8-tetrahydro-6H-cyclopent[g]quinazolin-6-yl)-N-(prop-2-ynyl)amino]-benzoyl}-L-γ-glutamyl}-D-glutamic acid [CB300951]

(100 ml), dried (Na$_2$SO4) and concentrated in vacuo. The residue was triturated with diethyl ether; the white precipitate was collected by filtration, washed with diethyl ether to afford the title compound (5.93 g, 83%), m.p. 104-105° C.; $^1$H-NMR (250 MHz, CDCl$_3$, TMS) 2.06 (m, 2H, 2-CH$_2$), 2.87 (m, 4H, 1-CH$_2$ and 3-CH$_2$), 3.50 (s, 3H, OCH$_3$), 400 (s, 2H, 2-CH$_2$OMe), 7.22 (m (overlap with CHCl$_3$ peak), 2H, 6-H, 7-H), 7.52 (s, 1H, 4-H), 8.18 (s, 1H, CONH); MS (ES, m/z): 432 [(2M+Na)$^+$, 30%], 206[(M+H)$^+$, 100%]; Found C, 70.10; H, 7.38; N, 6.81; C$_{12}$H$_{15}$NO$_2$ requires C, 70.22; H, 7.37; N, 6.82%.

5-Methoxyacetamido-6bromoindan

A mixture of 5-methoxyacetamidoindan (5.50 g, 0.027 mol) and glacial acetic acid (25 ml) was cooled in an ice-water bath (~10° C.). Bromine (1.5 ml, 0.029 mol) was then dropwise added over a 20 min period while the temperature was kept between 10-15° C. The reaction mixture was then stirred for a longer 1 hour and then it was poured into an ice-water bath (100 ml) with the aid of water (70 ml). The precipitate was collected by filtration, washed with plenty of water (150 ml) and dried in vacuo over P$_2$O$_5$ to afford the title compound (6.98 g, 91%), m.p. 84-86° C.; $^1$H-NMR (250 MHz, CDCl$_3$, TMS) 2.09 (m, 2H, 2-CH$_2$), 2.88 (m, 4H, 1-CH$_2$ and 3-CH$_2$), 3.55 (s, 3H, OCH$_3$), 4.04 (s, 2H, 2-CH$_2$OMe), 7.34, 8.22 (2×s, 2H, 4-H, 7-H), 8.83 (s, 1H, CONH);

MS (ESI, m/z): 284, 286 [(M+H)$^+$, 98%, 100%; Br isotopic pattern]; Found C, 50.62; H, 4.93; N, 4.92; Br, 28.05; C$_{12}$H$_{14}$BrNO$_2$ requires C, 50.72; H, 4.97; N, 4.93; Br, 28.12%.

5-Methoxyacetamido-6-bromoindan-1-one

To a solution of 5-methoxyacetamido-6-bromoindan (0.85 g, 3.0 mmol) in glacial acetic acid (7 ml) heated at 55° C. was dropwise added a solution of CrO$_3$ (1.2 g, 12.0 mmol) in aqueous glacial acetic acid, (7 ml; v/v 1:1) over a 15 min period. The reaction mixture was then stirred at this temperature for 45 min. The reaction mixture was cooled in an ice-bath, then propan-2-ol (4 ml) was added and the

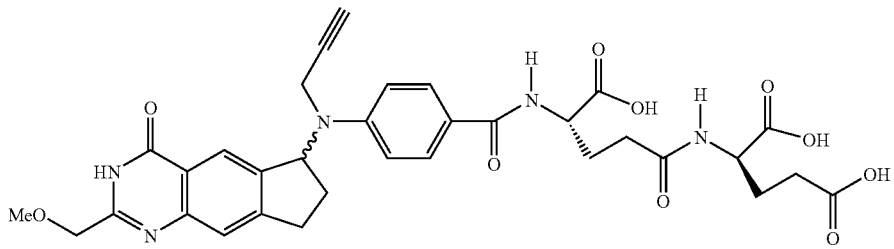

Synthesis is as in Scheme 2.

5-Methoxyacetamidoindan

To a solution of 5-aminoindan (4.66 g, 35.0 mmol) in anhydrous DMF (26 ml) was slowly added methoxyacetyl chloride (5.70 g, 52.50 mmol) followed by pyridine (8.5 ml, 105.0 mmol). The red solution was stirred at room temperature for 3.5 hours under argon, then it was partitioned between ethyl acetate (200 ml) and 1N HCl (120 ml). The organic layer was washed with more 1N HCl (120 ml), brine mixture was stirred at this temperature for 10 min before being concentrated in vacuo. The black residue was broken up with a spatula with the aid of water and then partitioned between water (50 ml) and ethyl acetate (150 ml). The aqueous layer was extracted with more ethyl acetate (2×40 ml); the combined extracts were dried (Na$_2$SO$_4$), and concentrated in vacuo to give an off white residue. Purification by column chromatography on elution with 5% ethyl acetate in dichloromethane afforded in order of elution:

a. 5-methoxyacetamido6-bromoindan-1-one as a white solid which was further purified by trituration with ethyl acetate/hexanes (1:5, v/v): 0.50 g (55%), m.p. 162-163° C.; $^1$H-NMR (250 MHz, CDCl$_3$, TMS) 2.72 (m, 2H, 2-CH$_2$), 3.11 (m, 2H, 3-CH$_2$), 3.57 (s, 3H, OCH$_3$), 4.09 (s, 2H, 2-CH$_2$OMe), 7.95 (s, 1H) and 8.65 (s, 1H) (2H, 4-H, 7-H), 9.27 (s, 1H, CONH); MS (ESI, m/z) 298, 300 {(M+H)$^+$, 100%, 97% respectively, bromine isotopic pattern}; Found: C, 48.13; H, 3.99; N, 4.70; Br, 26.95; C$_{12}$H$_{12}$BrNO$_3$ requires C, 48.34; N, 4.06; N, 4.70; Br, 26.80%); and b. 5-acetamido6-bromoindan-3-one as a solid which was further purified by trituration with ethyl acetate/hexanes (1:5, v/v): 0.026 g, (3%), m.p. 149-151° C. $^1$H-NMR (250 MHz, CDCl$_3$, TMS) 2.71 (m, 2H, 2-CH$_2$), 3.01 (m, 2H, 1-CH$_2$), 3.56 (s, 3H, OCH$_3$), 4.08 (s, 2H, 2-CH$_2$OMe), 7.73 (s, 1H) and 8.71 (s, 1H) (2H, 4-H, 7-H), 8.97 (s, 1H, CONH); MS (ESI, m/z) 298, 300 {(M+H)$^+$, 100%, 98% respectively, bromine isotopic pattern}; Found: C, 47.95; H, 3.96; N, 4.59; Br, 26.63; C$_{12}$H$_{12}$BrNO$_3$ requires C, 48.34; H, 4.06; N, 4.70; Br, 26.80%).

tert-Butyl 4-[N-(5-methoxyacetamido-6-bromoindan-1-yl)amino]benzoate

Method A: To a flask containing 5-methoxyacetamido-6-bromoindan-1-one (0.357 g, 1.2 mmol), 4-toluenesulfonic acid monohydrate (0.015 g), and tert-butyl 4-aminobenzoate (0.289 g, 1.5 mmol) was added 1,2-dimethoxyethane (dried by distillation over CaH$_2$; 15 ml). An Aldrich azeotropic distillation apparatus containing molecular sieves (3A) was fitted to the reaction flask that was placed in an oil bath preheated to 115° C. The reaction mixture was stirred at this temperature for 3.5 hours under argon; then allowed to cool to room temperature, and a solution of sodium cyanoborohydride in tetrahydrofuran (1M; 1.55 ml. 1.55 mmol) was added followed immediately by acetic acid (0.044 ml). The black reaction mixture was stirred at room temperature for 1 hour under argon; then it was partitioned between ethyl acetate (150 ml) and saturated aqueous sodium bicarbonate (100 ml). The aqueous layer was extracted with more ethyl acetate (100 ml); the organic extracts were combined, washed with brine (100 ml), dried (Na$_2$SO$_4$), and concentrated in vacuo to leave a reddish residue. Purification by column chromatography, on elution with 35% ethyl acetate in petroleum ether (60-80° C.), afforded the desired product as a white solid: 0.175 g (31%).

Method B: To a nearly clear solution of 5-methoxyacetamido-6-bromo-indan-1-one (0.300 g, 1.0 mmol) in anhydrou 4-aminobenzoate (0.193 g, 1.0 mmol) followed by decaborane (0.044 g). The reaction mixture was stirred at room temperature for 24 hours before being concentrated in vacuo. Purification by column chromatography, on elution with 35% ethyl acetate in petroleum ether (60-80° C.), afforded a white solid that was further purified by reprecipitation from dichloromethane/hexane: 0.340 g, (72%) m.p. 152-153° C.; $^1$H-NMR (250 MHz, CDCl$_3$, TMS) 1.57 (s, 9H, C(CH$_3$)$_3$), 1.93, 2.63 (2×m, 2H, indanyl 2-H), 2.97 (m, 2H, indanyl 3-H), 3.55 (s, 3H, OCH$_3$), 4.06 (s, 2H, CH$_2$OMe), 5.04 (t, J=6.50 Hz, 1H, 1-H), 6.64 (d, J 8.78 Hz, 2H, 3, 5-H), , 7.51, 8.33 (2×s, each 1H, indanyl 4-H, 7-H), 7.85 (d, J=8.75 Hz, 2, 6-H), 8.93 (s, 1H, CONH); MS (ESL, m/z) 499, 497 {(M+Na)$^+$, bromine isotopic pattern}.

tert-Butyl 4-[N-(5-methoxyacetamido-6-cyanoindan-1-yl)amino]benzoate

To a solution of tert-butyl 4-[N-(5-methoxyacetamido-6-bromoindan-1-yl)-amino]benzoate (0.714 g, 1.50 mmol) in NMP (8 ml) [1-methyl-2-pyrrolidone] was added copper(I) cyanide (0.230 g, 2.55 mmol). The reaction mixture was placed in an oil-bath preheated to 140° C. and stirred at this temperature for 2 h. More copper(I) cyanide (0.100 g, 1.10 mmol) was then added and stirring was continued for a longer 3 hours. The reaction mixture was allowed to cool to room temperature, then poured into a mixture of aqueous ammonia (d=0.88, 7 ml) and ice (~20 ml) and the resulting brown mixture was stirred at room temperature for ~5 min. The brown solid was collected by filtration washed with plenty of water, then suspended in dichloromethane (100 ml). The mixture was stirred at room temperature for 10 min, dried (Na$_2$SO$_4$), and concentrated in vacuo. Purification by column chromatography, on elution with 35% ethyl acetate in hexane, afforded an off white solid that was reprecipitated from dichloromethane-ethyl acetate/hexane: 0.328 g, (52%) m.p. 163-164° C. $^1$H-NMR (250 MHz, DMSO-d$_6$, TMS) 1.50 (s, 9H, C(CH$_3$)$_3$), 1.85, 2.58 (2×m, 2H, indanyl 2-H), 2.89 (m, 2H, indanyl 3-H), 3.41 (s, 3H, OCH$_3$), 4.05 (s, 2H, CH$_2$OMe), 5.06 (m, 1H, indanyl 1-H), 6.73 (d, J=8.82 Hz, 2H, 3, 5-H), 6.82 (d, J=8.37 Hz, 1H, N$^{10}$-H), 7.59, 7.57 (2×s, each 1H, indanyl 4-H, 7-H), 7.66 (d, J=8.77 Hz, 2, 6-H), 9.88 (s, 1H, CONH); MS (ESI, m/z) 444 {(M+Na)$^+$, 100%}; Found: C, 68.21; H, 6.47; N, 9.81; C$_{24}$H$_{27}$N$_3$O$_4$ requires C, 68.39; H, 6.46; N, 9.97%.

tert-Butyl 4{N-[(6RS)-2-methoxymethyl4-oxo-3,4,7,8-tetrahydro-6H-cyclopenta[g]quinazolin-6-yl]amino}benzoate A mixture of tert-butyl 4-[N-(5-methoxyacetamido-6-cyanoindan-1-yl)amino]benzoate (0.295 g, 0.70 mmol), ethanol (3.2 ml), and water (0.64 ml) was cooled in an ice-bath, then 30% aqueous H$_2$O$_2$ solution (0.60 ml) was added followed by granulated sodium hydroxide pellets (0.047 g, 1.19 mmol). The reaction mixture was stirred at ~0° C. for 10 min then it was placed in an oil bath preheated to 55° C. and stirred at this temperature for 30 min. The reaction mixture was allowed to cool to room temperature, then the solvents were removed in vacuo and the residue was suspended in water (~15 ml). The pH of this mixture was adjusted to ~12 with 1N NaOH (got a clear solution), then to ~4 with 1N hydrochloric acid. The off white precipitate was collected by filtration, washed with water, dried in vacuo over P$_2$O$_5$: 0.262 g (89%), m.p. >122° C. (softens); $^1$H-NMR (250 MHz, DMSO-d$_6$, TMS) 1.50 (s, 9H, C(CH$_3$)$_3$), 1.87, 2.56 (2×m, each 1H, 7-H), 3.00 (m, 2H, 8-H), 3.34 (s, 3H, OCH$_3$), 4.30 (s, 2H, 2-CH$_2$), 5.16 (m, 1H, 6-H), 6.78 (d, J=8.55 Hz, 2H, 3', 5'-H), 6.89 (d, J=8.10, N$^{10}$-H), 7.52, 7.90 (2×s, each 1H, 5-H, 9-H), 7.67 (d, J=8.45 Hz, 2', 6'-H), 12.12 (s, 1H, N$^3$-H); MS (ESI, m/z) 444 {(M+Na)$^+$, 40%}; Found: C, 67.19; H, 6.31; N, 9.69; C$_{24}$H$_{27}$N$_3$O$_4$ 0.5H$_2$O requires C, 66.96; H, 6.50; N, 9.76%.

(Propargyl)Co$_2$(CO)$_6$$^+$BF$_4$$^-$

This was prepared as in Example 1 from the dicobaltexacarbonyl propargyl alcohol complex. It was immediately used in the next reaction without any further purification.

tert-Butyl 4-{N-[(6RS)-2-methoxymethyl4-oxo-3,4,7,8-tetrahydro-6H-cyclopenta[g]quinazolin-6yl]-N-(prop-2-ynyl)amino}benzoate To a round-bottomed flask containing the tetrafluoroborate salt (propargyl)Co$_2$(CO)$_6$$^+$BF$_4$$^-$ (0.271 g, 0.66 mmol) was added anhydrous dichloro-methane (dried by distillation over P$_2$O$_5$; 22 ml). The nearly clear red dark solution was stirred at room temperature for few minutes under argon, then tert-butyl 4-{N-[(6RS)-2-methoxymethyl-4-oxo-3,4,7,8-tetrahydro-6H-cyclopenta[g]quinazolin-6-yl]amino}benzoate (0.215 g, 0.51 mmol) was added in one portion. Stirring was continued at this temperature for 5 min then diisopropylethylamine (0.18 ml, 1.04 mmol) was added and the reaction mixture was stirred at room temperature for 45 min under argon. The reaction mixture was partitioned between ethyl acetate (150 ml) and brine (60 ml). The aqueous layer was extracted with more ethyl acetate (2×50 ml). The combined extracts were washed with 10% aqueous citric acid (50 ml), brine (50 ml), dried (Na$_2$SO$_4$), and concentrated in vacuo. Purification by column chromatography, on elution with 40% ethyl acetate in dichloromethane, gave a red solid: 0.285 g (75%). To a solution of this complex (0.267 g, 0.36 mmol) in ethanol (60 ml) was added Fe(NO$_3$)$_3$.9H$_2$O (~8.0 g). The clear solution was stirred at room temperature for 10 min then a second portion of Fe(NO$_3$)$_3$.9H$_2$O (~4.0 g) was added. The reaction mixture was stirred at room temperature for a longer 5 min then a final portion of Fe(NO$_3$)$_3$.9H$_2$O (~5.0 g) was added; the nearly clear solution was turned into a dark red mixture. Stirring was continued at room temperature for an extra 25 min, then the reaction mixture was partitioned between ethyl acetate (150 ml) and dilute brine (70 ml). The aqueous layer was extracted with more ethyl acetate (2×70 ml), The combined organics were washed with brine (3×70 ml), dried (Na$_2$SO$_4$), and concentrated in vacuo. Purification by column chromatography, on elution with 2% methanol in dichloromethane, afforded a white solid which was reprecipitated from dichloromethane/hexane: 0.122 g (74%), m.p. 191-192° C.; $^1$H-NMR (250 MHz, DMSO-d$_6$, TMS) 1.51 (s, 9H, C(CH$_3$)$_3$), 2.23, 2.53 (m-obscured by DMSO peak) (2×m, each 1H, 7-H), 2.95-3.20 (m, 3H, C≡CH, 8-H), 3.34 (s (obscured by the H$_2$O peak), 3H, OCH$_3$), 3.96 (ABq, J=18.0 Hz, 2H, CH$_2$C≡C), 4.31 (s, 2H, 2-CH$_2$), 5.79 (t, J=7.0 Hz, 1H, 6-H), 7.02 (d, J=9.01 Hz, 2H, 3', 5'-H), 7.58, 7.80 (2×s, each 1H, 5-H, 9-H), 7.76 (d, J=8.45 Hz, 2', 6'-H), 12.17 (s, 1H, N$^3$-H); MS (ESI, m/z) 4.82 {(M+Na)$^+$, 10%}; Found: C, 70.32; H, 6.31; N, 9.09; C$_{27}$H$_{29}$N$_3$O$_4$ requires C, 70.57; H, 6.36; N, 9.14%.

4-{N-[(6RS)-2-Methoxymethyl4-oxo-3,4,7,8-tetrahydro-6H-cyclopenta-[g]quinazolin-6-yl]-N-(prop-2-ynyl)amino}benzoic acid A solution of tert-butyl 4-{N-[(6RS)-2-methoxymethyl-4-oxo-3,4,7,8-tetra-hydro-6H-cyclopenta[g]quinazolin-6-yl]-N-(prop-2-ynyl)amino}benzoate (0.069 g, 0.15 mmol) in dichloromethane (1 ml) and trifluoroacetic acid (3 ml) was stirred at room temperature for 1 hour and 10 min, then the solvents were removed in vacuo. The residue was triturated with diethyl ether and the precipitate was collected by filtration, washed with diethyl ether and dried in vacuo over P$_2$O$_5$ to afford the title compound as the tifluoroacetate salt: 0.061 g, m.p. 225° C. (dec); $^1$H-NMR (250 MHz, DMSO-d$_6$, TMS) 2.23, 2.53 (obscured by DMSO peak) (2×m, each 1H, 7-H), 2.90-3.20 (m, 3H, C≡CH, 8-H), 3.34 (s (obscured by the H$_2$O peak), 3H, OCH$_3$), 3.97 (ABq, J=18.0 Hz, 2H, CH$_2$C≡C), 4.32 (s, 2H, 2-CH$_2$), 5.79 (t, J=8.1 Hz, 1H, 6-H), 7.03 (d, J=9.02 Hz, 2H, 3', 5'-H), 7.58, (s, 1H, 9-H), 7.81 (m, 3H, 5-H, 2', 6'-H), 12.17 (s, 1H, N$^3$-H); MS (ESI, m/z) 426 {(M+Na)$^+$, 25%}, 404 {(M+H)$^+$, 70%}.

Tri-tert-butyl N-{N-{4-[N-((6RS)-2-methoxymethyl-4-oxo-3,4,7,8-tetra-hydro-6H-cyclopenta[g]quinazolin-6-yl)-N-(prop-2-ynyl)amino]benzoyl}-L-γ-glutamyl}-D-glutamate To a mixture of 4-{N-[(6RS)-2-methoxymethyl-4-oxo-3,4,7,8-tetrahydro-6H-cyclopenta[g]quinazolin-6-yl]-N-(prop-2-ynyl)amino}benzoic acid trifluoro-acetate salt (0.056 g, ~0.14 mmol), tri-tert-butyl L-γ-glutamyl-D-glutamate (0.090 g, 0.20 mmol) and anhydrous DMF (2.5 ml) was added diethyl cyanophosphonate (0.050 g, 0.31 mmol) followed by triethylamine (0.035 g, 0.35 inmol). The clear solution was stirred at room temperature for 2 hours, then it was partitioned between ethyl acetate (150 ml) and water (80 ml). The aqueous layer was extracted with ethyl acetate (2×70 ml). The combined organics were washed with 10% aqueous citric acid (2×40 ml), saturated sodium bicarbonate solution (100 ml) and brine (100 ml), dried (Na$_2$SO$_4$), and concentrated in vacuo. Purification by column chromatography, on elution with 1.5% methanol in ethyl acetate, afforded a white solid that was further purified by trituration with hexane with the aid of some dichloromethane: 0.072 g (64 %); m.p. >120° C.; $^1$H-NMR (250 MHz, DMSO-d$_6$, TMS) 1.38, 1.39, 1.41 (3×s, 27H, 3×C (CH$_3$)$_3$), 1.60-2.35 (m, 9H, 2×β-CH$_2$, 2×γ-CH$_2$, 7-H), 2.52 (m obscured by DMSO peak, 1H, 7-H), 2.90-3.25 (m, 3H, C≡CH, 8-H), 3.97 (ABq, J=17.0 Hz, 2H, CH$_2$C≡C), 4.08, 4.12 (2×m, 2H, 2×α-CH), 4.32 (s, 2H, 2-CH$_2$), 5.77 (t, J=7.50 Hz, 1H, 6-H), 7.02 (d, J=8.85 Hz, 2H, 3', 5'-H), 7.58 (s, 1H, 9-H), 7.80 (d, J=9.0 z, 2H, 2', 6'-H), 7.82 (s, 1H, 5-H), 8.17 (d, J=8.12 Hz, 1H, CONH), 8.36 (d, J=7.00 Hz, 1H, CONH), 12.16 (s, 1H, N$^3$—H); MS (ESI, m/z) 852 {(M+Na)$^+$, 20%}, 830 {(M+H)$^+$, 100%}; Found C, 64.71; H, 7.21; N, 8.27. C$_{45}$H$_{59}$N$_5$O$_{10}$ requires C, 65.12; H, 7.17; N, 8.44%.

N-{N-{4-[N-((6RS)-2-Methoxymethyl4-oxo-3,4,7,8-tetrahydro-6H-cyclo-penta[g]quinazohn-6yl)-N-(prop2-ynyl)amino]benzoyl}-L-γ-glutamyl}-D-glutamic acid A solution of tri-tert-butyl N-{N-{4-[N-((6RS)-2-methoxymethyl4-oxo-3,4,7,8-tetrahydro-6H-cyclopenta[g]quinazolin-6-yl)-N-(prop-2-ynyl)amino]-benzoyl}-L-γ-glutamyl}-D-glutamate (0.056 g, 0.07 mmol) in trifluoroacetic acid (4.5 ml) was stirred at room temperature for 1 hour and 10 min with protection from the light. The solvent was then removed in vacuo and the residue was suspended in water (4 ml). The pH was adjusted to ~10 with 1N NaOH, then to ~4 with 1N hydrochloric acid. The white precipitate was collected by filtration and dried in vacuo over P$_2$O$_5$: 0.020 g (45%), m.p. 150-155° C. (softens); $^1$H-NMR (250 MHz, DMSO-hd6, TMS) 1.60-2.30 (m, 9H, 2×β-CH$_2$, 2×γ-CH$_2$, 7-H), 2.52 (m obscured by DMSO peak, 1H, 7-H), 2.90-3.25 (m, 3H, C≡CH, 8-H), 3.36 (s, 3H, OCH$_3$), 3.97 (ABq, J=17.0 Hz, 2H, CH$_2$C≡C), 4.20, 4.34 (2×m, 2H, 2×α-CH), 4.32 (s, 2H, 2-CH$_2$), 5.77 (t, J=8.02 Hz, 1H, 6-H), 7.02 (d, J=8.85 Hz, 2H, 3', 5'-H), 7.58 (s, 1H, 9-H), 7.81 (d, J=9.0 z, 2H, 2', 6'-H), 7.83 (s, 1H, 5-H), 8.14 (d, J=8.12 Hz, 1H, CONH), 8.33 (d, J=7.78 Hz, 1H, CONH), 12.10 (s, 1H, N$^3$—H); MS (ESI, m/z) 662 {(M+H)$^+$, 100%}.

EXAMPLE 3 synthesis of N-{N-{4-[N-((6RS)-2-Hydroxymethyl-4-oxo-3,4,7,8-tetrahydro-6H-cyclopenta[g]quinazolin-6-yl)-N-(prop-2-ynyl)amino]-benzoyl}-L-γ-glutamyl}-D-glutamic acid [CB300945]

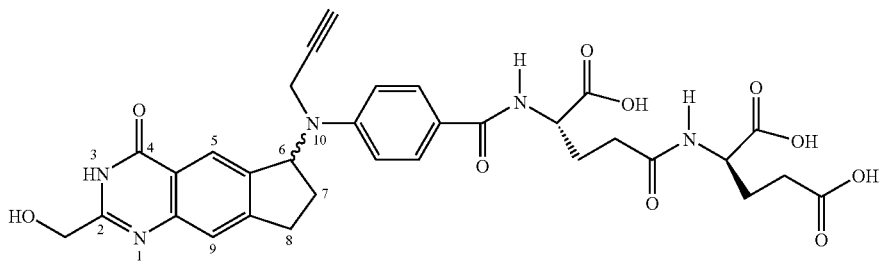

CB300945

Synthesis is as in Scheme 3.

2-Hydroxymethyl-3,4,7,8-tetrahydro-6H-cyclopenta[g]quinazolin-4-one

A solution of caesium acetate (14.4 g, 75.2 mmol) in dry DMF (40 ml) was heated to 60° C. under argon for 30 min. The mixture was cooled to 40° C. and a suspension of 2chloromethyl-3,4,7,8-tetrahydro-6H-cyclopenta[g] quinazolin-4-one (L. Skelton, V. Bavetsias, A. Jaclinan, WO 00/050417-A1; 2.2 g, 9.4 mmol) in dry DA (60 ml) was added via a cannula. The mixture was heated to 80° C. under argon for 16 h. The mixture was cooled to room temperature and the solvent was removed in vacuo. The residue was suspended in water (50 ml) and MeOH (20 ml). The pH was adjusted to 12.5 with 1M sodium hydroxide solution and the brown suspension was stirred for 2 h at room temperature. The insoluble brown solid was removed by filtration and the resulting solution was acidified to pH 5 with 1M hydrochloric acid. The precipitate was collected by filtration, washed with acidified water and dried in vacuo over P$_2$O$_5$ to yield the product as a pale yellow solid (1.17 g, 58%); m.p. 205-210° C.; $^1$H NMR (DMSO-d$_6$) δ 2.07 (quin, J=7.4 Hz, 2H, 7-H), 2.98 (q, J=6.95 Hz, 4H, 6-H and 8-H), 4.38 (s, 2H, 2-CH$_2$), 7.46 (s, 1H, 9-H), 7.92 (s, 1H, 5-H); MS (FAB-m/z): Found 217 [(M+H)$^+$, 100%]; RRMS: measured 217.0977; calculated for C$_{12}$H$_{13}$N$_2$O$_2$ (M+H)$^+$: 217.0977.

2-(2,2-Dimethylpropionyloxymethyl)-3,4,7,8-tetrahydro-6H-cyclopenta-[g]quinazolin4one 2-Hydroxymethyl-3,4,7,8-tetrahydro-6H-cyclopenta[g]quinazolin-4-one (1.0 g, 4.6 mmol), triethylamine (0.77 ml, 5.6 mmol), DMAP (50 mg, 0.4 mmol) and anhydrous CH$_2$Cl$_2$ (50 ml) were mixed in a flask under argon. Pivalic anhydride (1.2 ml, 6.0 mmol) was added dropwise and the suspension stirred at room temperature under argon for 5 h. The solvent was removed in vacuo and the residue partitioned between EtOAc (100 ml) and saturated aqueous NaHCO$_3$ (100 ml). The organic extract was washed with saturated aqueous NaHCO$_3$ (70 ml), water (70 ml), brine (70 ml), dried (Na$_2$SO$_4$) and the solvent removed in vacuo. The residue was triturated with hexane (60 ml) and the product collected by filtration as a yellow solid (1.21 g, 87%); m.p. 185-190° C.; $^1$H-NMR (DMSO-d$_6$) δ 1.22 (s, 9H, CMe$_3$), 2.07 (quin, J=7.4 Hz, 2H, 7-H), 2.98 (q, J=5.72 Hz, 4H, 6-H and 8-H), 4.94 (s, 2H, 2-CH$_2$), 7.42 (s, 1H, 9-H), 7.92 (s, 1H, 5-H), 12.20 (br, 1H, NH); MS (FAB, m/z): Found 301 [(+H)$^+$, 100%]; HMS: measured 301.1539; calculated for C$_{17}$H$_{21}$N$_2$O$_3$ (M+H)$^+$: 301.1552; Found C, 67.65; H, 6.54; N, 9.54. C$_{17}$H$_{21}$N$_2$O$_3$ requires C, 67.98; H, 6.71; N, 9.33%.

2-(2,2-Dimethylpropionyloxymethyo)-3,4,7,8-tetrahydro6H-cyclopenta-[g]quinazolin-4,6-dione and 2-(2,2-Dimethylpropionyloxymethyl)-3,4,7,8-tetra-hydro-6H-cyclopenta[g]quinazolin-4,8-dione To a stirred solution of (Ph$_3$SiO)$_2$CrO$_2$ (L. M. Baker and W. L. Carrick, *J. Org. Chem.* 1970, 35, 774) (10.6 mg, 0.017 mmol) in CH$_2$Cl$_2$ (5 ml) was added sequentially aqueous 70% tert-butyl hydroperoxide (0.18 ml, 1.3 mmol) and 2-(2,2-dimethylpropionyloxymethyl)-3,4,7,8-tetrahydro-6H-cyclopenta[g]quinazolin-4-one (0.1 g, 0.33 mmol). The mixture was stirred at room temperature with protection from the light for 24 h. The solvents were removed in vacuo and the residue purified by column chromatography (20 g of silica gel) eluting with a gradient of 10-30% EtOAc in CHCl$_3$ to yield 2-(2,2-dimethylpropionyloxymethyl)-3,4,7,8-tetrahydro-6H-cyclopenta[g]quinazolin-4,6-dione as a white solid (47 mg, 45%); m.p. 185-190° C.; $^1$H-NMR (DMSO-d$_6$) δ 1.23 (s, 9H, CMe$_3$), 2.72 (m, 2H, 7-H), 3.25 (m, 2H, 8-H), 5.00 (s, 2H, 2-CH$_2$), 7.70 (s, 1H, 9-H), 8.29 (s, 1H, 5-H), 12.20 (br, 1H, NH); MS (FAB, m/z): Found 315 [(M+H)$^+$, 100%], 337 [(M+Na)$^+$, 75%]; HRMS: measured 315.1360; calculated for C$_{17}$H$_{19}$N$_2$O$_4$ (M+H)$^+$: 315.1345; Found C, 64.18; H, 5.72; N, 8.81. C$_{17}$H$_{18}$N$_2$O$_4$.0.2H$_2$O requires C, 64.23; H, 5.79; N, 8.82%.

2-(2,2-Dimethylpropionyloxymethyl)-3,4,7,8-tetrahydro-6H-cyclopenta[g]-quinazolin-4,8-dione; $^1$H-NMR (DMSO-d$_6$) δ 1.23 (s, 9H, CMe$_3$), 2.76 (m, 2H, 7-H), 3.26 (m, 2H, 8-H), 4.98 (s, 2H, 2-CH$_2$), 7.72 (s, 1H, 9-H), 8.29 (s, 1H, 5-H), 12.3 (br, 1H, NH).- tert-Butyl 4-[N-((6RS)-2-(2,2-dimethylpropionyloxymethyl)-4-oxo-3,4,7,8-tetrahydro-6H-cyclopenta[g]quinazolin-6-yl)amino]benzoate A suspension of 2-(2,2-dimethylpropionyloxymethyl)-3,4,7,8-tetrahydro-6H-cyclopenta[g]quinazolin-4,6-dione (0.47 g, 1.50 mmol) in anhydrous methanol (33 ml) and anhydrous $CH_2Cl_2$ (5 ml) was treated with tert-butyl 4-aminobenzoate (0.34 g, 1.78 mmol) followed by decaborane (0.07 g, 0.58 mmol) and the mixture stirred at room temperature under argon for 18 h. The solvent was removed in vacuo and the residue purified by column chromatography (50 g of silica gel) eluting with 30% ethyl acetate in $CH_2Cl_2$ to yield the desired product as a white solid (0.43 g, 58%); m.p. 231° C.; $^1$H-NMR ($CDCl_3$) δ 1.26 (s, 9H, $CMe_3$), 1.58 (s, 9H, $CO_2CMe_3$), 2.00 (m, 1H, 7-H), 2.72 (m, 1H, 7-H), 3.08 (m, 2H, 8-H), 5.10 (s, 2H, 2-$CH_2$), 5.15 (m, 1H, 6-H), 6.67 (d, J=8.8 Hz, 2H, 3'-H, 5'-H), 7.58 (s, 1H, 9-H), 7.87 (d, J=8.8 Hz, 2H, 2'-H, 6'-H), 8.24 (s, 1H, 5-H); MS (FAB, mz): Found 491 [$(M+H)^+$, 25%], 514 [$(M+Na)^+$, 100%]; Found C, 68.37; H, 6.86; N, 8.35. $C_{28}H_{33}N_3O_5$ requires C, 68.41; H, 6.77; N, 8.55%.

tert-Butyl 4-[N-((6RS)-2-(2,2-dimethylpropionyloxymethyl)4-oxo-3,4,7,8-tetrahydro-6H-cyclopentag[g]quinazolin-6-yl)-N-(prop-2-ynyl)amino]benzoate A suspension of (propargyl)$Co_2(CO)_6^+BF_4^-$ (213 mg, 0.52 mmol) in anhydrous $CH_2Cl_2$ (25 ml) was treated with tert-butyl 4-[N-((6RS)-2-(2,2-dimethyl-propionyloxymethyl)-4-oxo-3,4,7,8-tetrahydro-6H-cyclopenta[g]quinazolin-6-yl)-amino]benzoate (200 mg, 0.41 mmol) and the red solution stirred at room temperature under argon for 15 minutes. Diisopropylethylamine (0.15 ml, 0.86 mmol) was added and the mixture stirred at room temperature under argon for 1 h. The mixture was partitioned between ethyl acetate (30 ml) and brine (30 ml). The organic extract was dried ($Na_2SO_4$) and the solvent removed in vacuo. The residue was purified by column chromatography (20 g of silica gel) eluting with a gradient of 0-10% ethyl acetate in $CH_2Cl_2$ to yield the complex as a red oil (191 mg, 58%); $^1$H-NMR ($CDCl_3$) δ 1.26 (s, 9H, $CMe_3$), 1.59 (s, 9H, $CO_2CMe_3$), 2.31 (m, 1H, 7-H), 2.62 (m, 1H, 7-H), 3.13 (m, 2H, 8-H), 4.57 (AB system, J=16.9 Hz, 2H, propargyl $CH_2$), 5.09 (s, 2H, 2-$CH_2$), 5.63 (t, J=8.3, 1H, 6-H), 5.98 (s, 1H, propargyl CH), 6.91 (d, J=8.9 Hz, 2H, 3'-H, 5'-H), 7.61 (s, 1H, 9-H), 7.90 (d, J=8.9 Hz, 2H, 2'-H, 6'-H), 8.14 (s, 1H, 5-H), 10.25 (br s, 1H).

A solution of this complex (186 mg, 0.23 mmol) in ethanol (30 ml) was treated with $Fe(NO_3)_3.9H_2O$ (1.1 g) and the solution stirred at room temperature for 2 h. The solution was partitioned between ethyl acetate (30 ml) and water (30 ml). The organic extract was washed with brine (30 ml), dried ($Na_2SO_4$) and the solvent removed in vacuo. The residue was purified by column chromatography (20 g of silica gel) eluting with 10% ethyl acetate in $CH_2Cl_2$ to yield the desired product as a white solid (94 mg, 78%); m.p. 134° C.; $^1$H-NMR ($CDCl_3$) δ 1.32 (s, 9H, $CMe_3$), 1.61 (s, 9H, $CO_2CMe_3$), 2.23 (s, 1H, propargyl CH), 2.38 (m, 1H, 7-H), 2.62 (m, 1H, 7-H), 3.07 (m, 1H, 8-H), 3.25 (m, 1H, 8-H), 3.94 (AB system, J=18.6 Hz, 2H, propargyl $CH_2$), 5.12 (s, 2H, 2-$CH_2$), 5.68 (t, J=8.2 Hz, 1H, 6-H), 6.99 (d, J=9.1 Hz, 2H, 3'-H, 5'-H), 7.63 (s, 1H, 9-H), 7.95 (d, J=9.0 Hz, 2H, 2'-H, 6'-H), 8.16 (s, 1H, 5-H), 9.55 (br s, 1H); MS (ESI, m/z) 552 {$(M+Na)^+$, 100%}, 530 {$(M+H)^+$, 20%}; Found C, 70.14; H, 6.80; N, 7.73. $C_{31}H_{35}N_3O_5$ requires C, 70.30; H, 6.66; N, 7.93%.

4-[N-((6RS)-2-(2,2-Dimethylpropionyloxymethyl)4-oxo-3,4,7,8-tetra-hydro-6H-cyclopenta[g]quinazolin-6-yl)-N-(prop-2-ynyl)amino]benzoic acid A solution of tert-butyl 4-[N-((6RS)-2-(2,2-dimethylpropionyloxymethyl)-4-oxo-3,4,7,8-tetrahydro-6H-cyclopenta[g]quinazolin-6-yl)-N-(prop-2-ynyl)amino]-benzoate (80 mg, 0.15 mmol) in trifluoroacetic acid (5 ml) was stirred at room temperature with protection from the light for 1.5 h. The solvent was removed in vacuo and the residue triturated with 1:1 diethyl ether and hexane to yield the desired product as a white solid (81 mg, TFA salt); m.p. 133° C.; $^1$H-NMR (DMSO-d6) δ 1.23 (s, 9H, $CO_2CMe_3$), 2.22 (m, 1H, 7-H), 2.50 (m, 1H, 7-H), 3.03 (m, 2H, 8-H), 3.14 (s, 1H, propargyl CH), 3.97 (AB system, J=18.8 Hz, 2H, propargyl $CH_2$), 4.95 (s, 2H, 2-$CH_2$), 5.79 (t, J=8.6 Hz, 1H, 6-H), 7.03 (d, J=9.0 Hz, 2H, 3'-H, 5'-H), 7.51 (s, 1H, 9-H), 7.81 (d, J=6.6 Hz, 2H, 2'-H, 6'-H), 7.83 (s, 1H, 5-H).

Tri-tert-butyl N-{N-{4-[N-((6RS)-2-(2,2-dimethylpropionyloxymethyl)-4-oxo-3,4,7,8-tetrahydro-6H-cyclopenta[g]quinazolin-6-yl)-N-(prop-2-ynyl)-amino]benzoyl}-L-γ-glutamyl}-D-glutamate A solution of 4-[N-((6RS)-2-(2,2-dimethylpropionyloxymethyl)4-oxo-3,4,7,8-tetrahydro-6H-cyclopenta[g]quinazolin-6-yl)-N-(prop-2-ynyl)amino]benzoic acid (80 mg, 0.15 mmol) in anhydrous dimethylformamide (7 ml) was treated with tri-tert butyl-L-γ-glutamyl-D-glutamate (150 mg, 0.33 mmol), diethyl cyano-phosphonate (0.06 ml, 0.40 mmol) and triethylarnine (0.06 ml, 0.40 mmol). The solution was stirred at room temperature under argon with protection from the light for 2.5 h. The solution was partitioned between ethyl acetate (25 ml) and water (25 ml). The aqueous layer was extracted with ethyl acetate (2×20 ml). The combined organic extracts were washed with 10% aqueous citric acid (2×30 ml), saturated aqueous $NaHCO_3$ (30 ml), dilute brine (30 ml), dried ($Na_2SO_4$) and the solvent removed in vacuo. The residue was purified by column chromatography (30 g of silica gel) eluting with 40% ethyl acetate in $CH_2Cl_2$ to yield the desired product as a white solid (94 mg, 62%); m.p. 109° C.; $^1$H-NMR ($CDCl_3$) δ 1.29 (s, 9H, —$COCMe_3$), 1.43 (s, 9H, $COOCMe_3$), 1.47 (s, 9H, $COOCMe_3$), 1.48 (s, 9H, $COOCMe_3$), 1.60-2.10 (m, 5H, 2×glu β-$CH_2$, 7-CH), 2.21 (s, 1H, propargyl CH), 2.22-2.50 (m, 4H, 2×glu γ-$CH_2$), 2.59 (m, 1H, 7-H), 3.08 (m, 1H, 8-H), 3.20 (m, 1H, 8-H), 3.92 (AB system, J=19.0 Hz, 2H, propargyl $CH_2$), 4.48, 4.76 (2×m, 2H, 2×glu α-CH), 5.12 (s, 2H, 2-$CH_2$), 5.64 (t, J=8.1 Hz, 1H, 6-H), 6.99 (d, J=8.8 Hz, 2H, 3'-H, 5'-H), 7.07 (m, 2H, 2×CONH), 7.64 (s, 1H, 9-H), 7.80 (d, J=8.8 Hz, 2H, 2'-H, 6'-H), 8.13 (s, 1H, 5-H); MS (ESI, m/z) 922 {$(M+Na)^+$, 100%}, 900 {$(M+H)^+$, 40%}; Found C, 64.85; H, 7.23; N, 7.33. $C_{49}H_{65}N_5O_{11}.0.5H_2O$ requires C, 64.76; H, 7.27; N, 7.71%.

N-{N-{4-[N-((6RS)-2-Hydroxymethyl-4-oxo-3,4,7,8-tetrahydro-6H-cyclo-penta[g]quinazolin-6-yl)-N-(prop-2-ynyl)amino]benzoyl}-L-γ-glutamyl}-D-glutamic acid Tri-tert-butyl N-{N-{4-[N-((6RS)-2-(2,2-dimethylpropionyloxymethyl)-4-oxo-3,4,7,8-tetrahydro-6H-cyclopenta[g]quinazolin-6-yl)-N-(prop-2-ynyl)amino]-benzoyl}-L-γ- glutamyl}-D-glutamate (80 mg, 0.09 mmol) was dissolved in trifluoro-acetic acid (5 ml) and stirred at room temperature with protection from the light for 1 h. The solvent was removed in vacuo and the residue dissolved in methanol (3 ml) and water (3 ml). The pH of the solution was adjusted to pH 12 with 1M sodium hydroxide solution and stirred at room temperature for 6 h. The solution was acidified to pH 4 with 1M hydrochloric acid and cooled to 0° C. The precipitate was collected by filtration and dried under vacuum over $P_2O_5$ to yield the desired product as a pale brown solid (27 mg, 47%); m.p. 172° C.; $^1$H-NMR (DMSO-$d_6$) δ 1.60-2.10 (m, 5H, 2×glu β-$CH_2$, 7-CH), 2.15-2.40 (m, 5H, 2×glu γ-$CH_2$, 7-H), 2.99 (m, 1H, 8-H), 3.12 (s, 1H, propargyl CH), 3.16 (m, 1H, 8-H), 3.98 (AB system, J=19.9 Hz, 2H, propargyl $CH_2$), 4.18, 4.30 (2×m, 2H, 2×glu α-CH), 4.36 (s, 2H, 2-$CH_2$), 5.58 (br s, 1H, —OH), 5.77 (t, J=7.9 Hz, 1H, 6-H), 7.01 (d, J=8.9 Hz, 2H, 3'-H, 5'-H), 7.54 (s, 1H, 9-H), 7.80 (d, J=8.5 Hz, 2H, 2'-H, 6'-H), 7.82 (s, 1H, 5-H), 8.15 (d, J=7.5 Hz, 1H), 8.35 (d, J=7.2 Hz, 1H) (2×CONH); MS (ESI, m/z) 670 {(M+Na)$^+$, 45%}, 648 {(M+H)$^+$, 100%}; HRMS: measured 648.2313; calculated for $C_{32}H_{35}N_5O_{10}$ (M+H)$^+$: 648.2306.

EXAMPLE 4 synthesis of N-{N-{4[N-((6RS)-2-methyl-4-oxo-3,4,7,8-tetra-hydro-6H-cyclopental[g]quinazolin-6-yl)-N-(prop2-ynyl)amino]-2-fluoro-benzoyl}-L-γ-glutamyl}-D-glutamic acid [CB300947]

each 1H, indanyl 4-H, 7-H, CONH), 7.72 (t, J=8.75 Hz, 6-H); MS (ESI, mz) 485, 487 {(M+Na)$^+$, bromine isotopic pattern}.

Tert-butyl 4-[N-(5-acetamido-6-cyanoindan-1-yl) amino]-2-fluorobenzoate

To a solution of tert-butyl 4-[N-(5-acetamido-6-bromoindan-1-yl)amino]-2-fluorobenzoate (0.420 g, 0.90 mmol) in NMP (10 ml) was added copper(I) cyanide (0.137 g, 1.53 mmol). The reaction mixture was placed in an oil-bath preheated to 145° C. and stirred at this temperature for 2 hours. The reaction mixture was allowed to cool to room temperature, then poured into a mixture of aqueous ammonia (d=0.88, 5 ml) and ice (~15 ml) and the resulting brown mixture was stirred at room temperature for ~5 min. The brown solid was collected by filtration washed with water, then suspended in dichloromethane (60 ml). The mixture was stirred at room temperature for 5 min, dried ($Na_2SO_4$), and concentrated in vacuo. Purification by column chromatography, on elution with 40% ethyl acetate in hexane, afforded a solid that was triturated with diethyl ether/hexane. The desired compound was obtained as a white solid: 0.202 g, (55%) m.p. 172-173° C.; $^1$H-NMR (250 MHz, CDCl$_3$, TMS) 1.57 (s (obscured by water peak), 9H, C(CH$_3$)$_3$), 2.27 (s, 3H, COCH$_3$), 1.96, 2.65 (2×m, 2H, indanyl 2-H), 3.00 (m, 2H, indanyl 3-H), 4.30 (d, J=8.40 Hz, 1H, N-H), 4.99 (q, J=7.80 Hz, 1H, indanyl 1-H), 6.38 (m, 2H, 3,5-H), 7.52, 8.33, 7.62 (3×s, each 1H, indanyl 4-H, 7-H, CONH), 7.74 (t, J=8.60 Hz, 1H, 6-H); MS (ESI m/z) 432 {M+Na)$^+$, 100%};

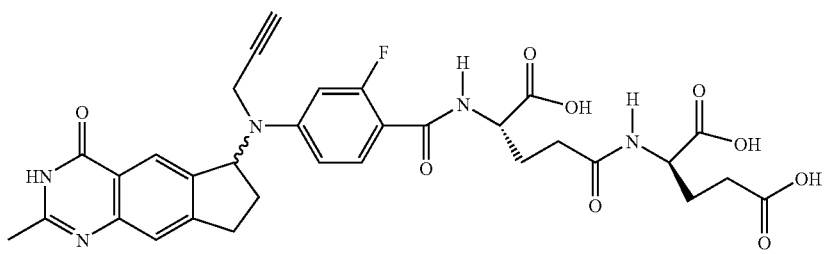

CB300947

Synthesis is as in Scheme 4.

tert-Butyl 4-[N-(5-acetamido-6-bromoindan-1-yl) amino]-2-fluorobenzoate

To a solution of 5-acetamido-6-bromoindan-1-one (0.370 g, 1.38 mmol) in anhydrous methanol (32 ml) was added tert-butyl 4-amino-2-fluorobenzoate (V. Bavetsias et al, *J. Med. Chem.* 1996, 39, 73-85; 0.322 g, 1.52 mmol) followed by decaborane (0.030 g). The reaction mixture was stirred at room temperature for 11 hours then more decaborane (0.005 g) was added and stirring was continued for a longer 12 hours under argon. The solvent was removed in vacuo, and the residue was purified by column chromatography eluting with a gradient of ethyl acetate in hexane (30 to 40%). The desired compound was obtained as a white solid: 0.455 g (71%) m.p.>70° C. (softens); $^1$H-NMR (250 MHz, CDCl$_3$, TMS) 1.57 (s, 9H, C(CH$_3$)$_3$), 2.24 (s, 3H, COCH$_3$), 1.98, 2.56 (2×m, 2H, indanyl 2-H), 2.94 (m, 2H, indanyl 3-H), 4.33(d, J=7.90 Hz, 1H, N—H), 4.99 (q, J=7.06 Hz, 1H, indanyl 1-H), 6.37 (m, 2H, 3,5-H), 7.48, 8.25, 7.60 (3×s, Found: C, 67.44; H, 5.88; N, 10.25; F, 4.63; $C_{23}H_{24}FN_3O_3$ requires C, 67.47; H, 5.91; N, 10.26%; F, 4.64%.

tert-Butyl 4-{N-[(6RS)-2-methyl-4-oxo-3,4,7,8-tetrahydro-6H-cyclopenta-[g]quinazolin-6-yl]aminio}-2-fluorobenzoate A mixture of tert-butyl 4-[N-(5-acetamido-6-cyanoindan-1-yl)amino]-2-fluorobenzoate (0.182 g, 0.44 mmol), ethanol (2 ml), and water (0.4 ml) was cooled in an ice-bath, then 30% aqueous $H_2O_2$ solution (0.37 ml) was added followed by granulated sodium hydroxide pellets (0.030 g, 0.75 mmol). The reaction mixture was stirred at ~0° C. for 10 min, then it was placed in an oil bath preheated to 55° C. and stirred at this temperature for 30 min. The reaction mixture was allowed to cool to room temperature, then the solvents were removed in vacuo and the residue was suspended in water (~15 ml). The pH of this mixture was adjusted to ~4 with 1N hydrochloric acid. The white precipitate was collected by filtration, washed with water, and dried in vacuo over $P_2O_5$. The desired compound was obtained as a white solid 0.155 g (85%), m.p. 150-152° C.; $^1$H-NMR (250 MHz, DMSO-$d_6$, TMS) 1.50 (s, 9H, C(CH$_3$)$_3$), 2.32 (s, 3H, 2-CH$_3$), 1.83, 2.53 (2×m, 2H, 7-H), 3.00 (m, 2H, 8-H), 5.15 (q, J=7.40 Hz, 1H, 6-H), 6.57 (m, 2H, 3', 5'-H), 7.16 (d, J=7.75 Hz, 1H, N$^{10}$-H), 7.44, 7.87 (2×s, each 1H, 5-H, 9-H), 7.59 (t, J=8.73 Hz, 6'-H), 12.11 (s, 1H, N$^3$-H); MS (ESI m/z) 819 {(2M+H)$^+$, 100%}, 432 {(M+Na)$^+$, 10%}, 410 {M+H}$^+$, 15%}; Found: C, 66.81; H, 5.89; N, 10.11; F, 4.58; C$_{23}$H$_{24}$FN$_3$O$_3$ 0.25H$_2$O requires C, 66.74; H, 5.96; N, 10.15%; F, 4.59%.

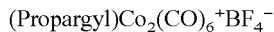

This was prepared as in Example 1 from the dicobalthexacarbonyl propargyl alcohol complex. It was used immediately in the next reaction without any further purification.

tert-Butyl 4-{N-[(6RS)-2-methyl-4-oxo-3,4,7,8-tetrahydro-6H-cyclopenta-[g]quinazolin-6-yl]-N-(prop-2ynyl)amino}-2-fluorobenzoate To a round-bottomed flask containing (Propargyl)Co$_2$(CO)$_6^+$BF$_4^-$ (0.174 g, 0.43 mmol) was added anhydrous dichloromethane (dried by distillation over P$_2$O$_5$; 14 ml). The solution was stirred at room temperature for few minutes under argon, then tert-butyl 4-{N-[(6RS)-2-methyl-4-oxo-3,4,7,8-tetrahydro-6H-cyclopenta[g]-quinazolin-6-yl]amino}-2-fluorobenzoate (0.135 g, 0.33 mmol) was added. Stirring was continued at this temperature for 5 min then diisopropylethylamine (0.4 ml) was added and the reaction mixture was stirred at room temperature for 25 min under argon. The reaction mixture was partitioned between ethyl acetate (80 ml) and brine (40 ml). The organic layer was washed with 10% aqueous citric acid (30 ml), brine (40 ml), dried (Na$_2$SO$_4$), and concentrated in vacuo. Purification by column chromatography, on gradient elution with ethyl acetate in dichloromethane (25 to 50%), gave a red solid 0.140 g (58%); $^1$H-NMR (250 MHz, CDCl$_3$, TMS) 1.58 (s, 9H, C(CH$_3$)$_3$), 2.54 (s, 3H, 2-Me), 2.32, 2.61 (m, each 1H, 7-H), 3.03, 3.23 (m, each 1H, 8-H), 4.55 (ABq, J=16.92 Hz, 2H, N$^{10}$—CH$_2$), 5.59 (t, J=8.30, 1H, 6-H), 6.00 (s, 1H, propargyl complex C—H), 6.59 (d, J=14.52 Hz, 1H, 3'-H), 6.69 (d, J=8.70 Hz, 1H, 5'-H), 7.58, 7.98 (s, each 1H, 5-H, 9-H), 7.79 (d, J=8.82 Hz, 6'-H), 10.96 (s, 1H, N$^3$-H). To a solution of this complex (0.100 g, 0.136 mmol) in ethanol (15 ml) was added Fe(NO$_3$)$_3$.9H$_2$O (~2 g). The clear solution was stirred at room temperature for 5 min then a second portion of Fe(NO$_3$)$_3$.9H$_2$O (~1.0 g) was added. The reaction mixture was stirred at room temperature for a longer 25 min then a final portion of Fe(NO$_3$)$_3$.9H$_2$O (~1.2 g) was added. Stirring was continued at room temperature for an extra 35 min, then the reaction mixture was partitioned between ethyl acetate (70 ml) and water (30 ml). The organic layer was washed with brine (2×30 ml), dried (Na$_2$SO$_4$), and concentrated in vacuo to leave a crispy solid. Purification by column chromatography, on elution with 5% methanol in chloroform, afforded a white solid; 0.040 g (67%), m.p. 248-250° C.; $^1$H-NMR (250 Mz, DMSO-$d_6$, TMS) 1.50 (s, 9H, C(CH$_3$)$_3$), 2.32 (s, 3H, 2-CH$_3$), 2.15 (m), 2.50 (m (obscured) (2H, 7-H), 2.90-3.20 (m, 3H, 8-H, C≡CH), 3.95 (ABq, J=18.52 Hz, 2H, CH$_2$C≡C), 5.74 (t, J=7.70 Hz, 1H, 6-H), 6.80 (m, 2H, 3', 5'-H), 7.48, 7.76 (2×s, each 1H, 5-H, 9-H), 7.68 (t, J=9.01 Hz, 1H, 6'-H), 12.10 (s, 1H, N$^3$-H); MS (ESI m/z) 470 {(M+Na)$^+$, 55%}, 448 {M+H}$^+$, 70%}; FAB-HRMS; measured: 470.1840, calculated for C$_{26}$H$_{26}$FN$_3$O$_3$Na: 470.1856.

N-[(6RS)-2-Methyl-4oxo-3,4,7,8-tetrahydro-6H-cyclopenta[g]quinazolin-6-yl]-N-(prop-2-ynyl) amino}-2-fluorobenzoic acid A solution of tert-butyl 4-{N-[(6RS)-2-methyl-4-oxo-3,4,7,8-tetrahydro-6H-cyclopenta[g]quinazolin-6-yl]-N-(prop-2-ynyl)amino}-2-fluorobenzoate (0.061 g, 0.14 mmol) in dichloromethane (1 ml) and trifluoroacetic acid (2.4 ml) was stirred at room temperature for 1.5 hours, then the solvents were removed in vacuo. The residue was triturated with diethyl ether and the precipitate was collected by filtration, washed with diethyl ether and dried in vacuo over P$_2$O$_5$ to afford the desired compound as the trifluoroacetate salt (0.046 g). $^1$H-NMR (250 MHz, DMSO-$d_6$, TMS) 2.33 (s, 3H, 2-CH$_3$), 2.18 (m), 2.50 (m (obscured)) (2H, 7-H), 2.85-3.20 (m, 3H, 8-H, C≡CH), 3.95 (ABq, J=19.02 Hz, 2H, CH$_2$C≡C), 5.76 (t, J=7.95 Hz, 1H, 6-H), 6.80 (d, J=16.40 Hz, 1H, 3'-H), 6.84 (d, J=9.46 Hz, 1H, 5'-H), 7.48, 7.78 (2×s, each 1H, 5-H, 9-H), 7.74 (t, J=9.02 Hz, 6'-H), 12.14 (s, 1H, N$^3$-H); MS (ESI m/z) 783 {(2M+H)$^+$, 100%}, 392 {(M+H)$^+$, 55%}.

Tri-tert-butyl N-{N-{4-[N-((6RS)-2-methoxymethyl-4-oxo-3,4,7,8-tetra-hydro-6H-cyclopenta[g]quinazolin-6-yl)-N-(prop-2-ynyl)amino]-2-fluorobenzoyl}-L-γ-glutamyl}-D-glutamate To a solution of tri-tert-butyl L-γ-glutamyl-D-glutamate (V. Bavetsias et al, *J. Med. Chem.* 1996, 39, 73-85; 0.066 g, 0.14 mmol) in anhydrous DMF (2.5 ml) was added 4-{N-[(6RS)-2-methyl-4-oxo-3,4,7,8-tetrahydro-6H-cyclopenta[g]quinazolin-6-yl]-N-(prop-2-ynyl)amino}-2-fluorobenzoic acid trifluoroacetate salt (0.045 g, 0.11 mmol), followed by diethyl cyanophosphonate (0.051 g, 0.31 mmol) and triethyl-amine (0.032 g, 0.32 mmol). The reaction mixture was stirred at room temperature for 2.5 hours, then it was partitioned between ethyl acetate (150 ml) and water (100 ml). The aqueous layer was extracted with more ethyl acetate (100 ml). The combined organics were washed with 10% aqueous citric acid (2×50 ml), saturated sodium bicarbonate solution (2×50 ml), and brine (50 ml), then dried (Na$_2$SO$_4$), and concentrated in vacuo. Purification by column chromatography, on elution with 1% methanol in ethyl acetate, afforded a white solid: 0.077 g (67%); m.p.>110° C. (softens); $^1$H-NMR (250 MHz, DMSO-$d_6$, TMS) 1.37, 1.38, 1.41 (3×s, 27H, 3×C(CH$_3$)$_3$), 1.60-2.35 (m, 9H, 2×β-CH$_2$, 2×γ-CH$_2$, 7-H), 2.32 (s, 3H, 2-CH$_3$), 2.52 (m obscured by DMSO peak, 1H, 7-H), 2.86-3.23 (m, 3H, C≡CH, 8-H), 3.97 (ABq, J=19.0 Hz, 2H, CH$_2$C≡C), 4.12, 4.30 (2×m, 2H, 2×α-CH), 5.74 (t, J=8.70 Hz, 1H, 6-H), 6.80 (d, J=14.20 Hz, 1H, 3'-H), 6.85 (d, J=8.07 Hz, 1H, 5'-H), 7.48 (s, 1H, 9-H), 7.58 (t, J=8.8 Hz, 1H, 6'-H), 7.78 (s, 1H, 5-H), 7.98 (t, J=6.42 Hz, 1H, CONH), 8.13 (d, J=7.4 Hz, 1H, CH$_2$CONH), 12.11 (s, 1H, N$^3$-H); (ESI, m/z) 818 {(M+H)$^+$, 100%}; Found C, 64.34; H, 7.09; N, 8.20; F, 2.22. C$_{44}$H$_{56}$FN$_5$O$_9$ requires C, 64.61; H, 6.90; N, 8.56; F, 2.32%.

N-{N-{4-[N-((6RS)-2-methyl-4-oxo-3,4,7,8-tetrahydro-6H-cyclopenta[g]-quinazolin-6-yl)-N-(prop-2-ynyl)amino]-2-fluorobenzoyl}-L-γ-glutamyl}-D-glutamic acid A solution of tri-tert-butyl N-{N-{4-[N-((6RS)-2-methyl-4-oxo-3,4,7,8-tetra-hydro-6H-cyclopenta[g]quinazolin-6-yl)-N-(prop-2-ynyl)amino]-2-fluorobenzoyl}-L-γ-glutamyl}-D-glutamate (0.066 g, 0.08 mmol) in trifluoroacetic acid (4.5 ml) was stirred at room temperature for 1 hour and 10 min with protection from the light. The solvent was then removed in vacuo and the residue was suspended in water (5 ml). The pH was adjusted to ~12 with 1N NaOH, then to ~4 with 1N hydrochloric acid. The white precipitate was collected by filtration and dried in vacuo over $P_2O_5$: 0.032 g (63%), m.p. 175° C. (dec); $^1$H-NMR (250 MHz, DMSO-$d_6$, TMS) 1.65-2.25 (m, 9H, 2×β-$CH_2$, 2×γ-$CH_2$, 7-H), 2.32 (s, 3H, 2-$CH_3$), 2.52 (m obscured by DMSO peak, 1H, 7-H), 2.90-3.22 (m, 3H, C≡CH, 8-H), 3.95 (ABq, J=19.15 Hz, 2H, $CH_2$C≡), 4.18, 4.37 (2×m, 2H, 2×α-CH), 5.74 (t, J=8.30 Hz, 1H, 6-H), 6.81 (d, J=15.50 Hz, 1H, 3'-H), 6.85 (d, J=7.88 Hz, 1H, 5'-H), 7.48 (s, 1H, 9-H), 7.62 (t, J=8.8 Hz, 1H, 6'-H), 7.78 (s, 1H, 5-H), 7.97 (t, J=6.55 Hz, 1H, CONH), 8.12 (d, J=8.05 Hz, 1H, $CH_2$CONH), 12.11 (s, 1H, $N^3$-H); (ESI, m/z) 650 {(M+H)$^+$, 100%}; FAB-HRMS, measured: 672.2060; calculated for $C_{32}H_{32}FN_5O_9Na$: 672.2082.

EXAMPLE 5 synthesis of N-{N-{4-[N-((6RS)-2-hydroxymethyl-4-oxo-3,4,7,8-tetrahydro-6H-cyclopenta[g]quinazolin-6yl)-N-(prop-2-ynyl)amino]-benzoyl}-L-γ-glutamyl}-N-methyl-L-glutamic acid [CB300960]

3.97 (ABq, J=18.6 Hz, 2H, $CH_2$C≡C), 4.37 (d, J=6.1 Hz, 2H, 2-$CH_2$), 5.56 (t, 1H, $CH_2$OH), 5.78 (t, J=7.51 Hz, 1H, 6-H), 7.03 (d, J=8.9 Hz, 2H, 3', 5'-H), 7.55 (s, 1H, 9-H), 7.82 (m, 3H, 2', 6'-H, 5-H); MS (ESI, m/z) 779 {(2M+H)$^+$, 100%}, 390 {(M+H)$^+$, 60%}.

Method B: A solution of tert-butyl 4-{N-[(6RS)-2-hydroxymethyl-4-oxo-3,4,7,8-tetrahydro-6H-cyclopenta[g] quinazolin-6-yl]-N-(prop-2-ynyl)amino}-benzoate (0.050 g, 0.11 mmol) in dichloromethane (1 ml) and trifluoroacetic acid (2.4 ml) was stirred at room temperature for 1 hour. The solvents were then removed in vacuo, and the residue was triturated with diethyl ether. The off-white precipitate was collected by filtration, and washed with ether to obtain the desired product as the trifluoroacetate salt: 0.044 g.

Tri-tert-butyl N-{N-{4-[N-((6RS)-2-hydroxymethyl4-oxo-3,4,7,8-tetra-hydro-6H-cyclopenta[g] quinazolin-6-yl)-N-(prop-2-ynyl)amino]benzoyl}-L-γ-glutamyl}-N-methyl-L-glutamate To a mixture of 4-{N-[(6RS)-2-hydroxymethyl-4-oxo-3,4,7,8-tetrahydro-6H-cyclopenta[g]quinazolin-6-yl]-N-(prop-2-ynyl)amino}benzoyl acid (0.075 g, ~0.19 mmol), tri-tert-butyl L-γ-glutamyl-N-methyl-L-glutamate (V. Bavetsias et al., *J. Med. Chem.,* 1997, 40, 1495-1510; 0.110

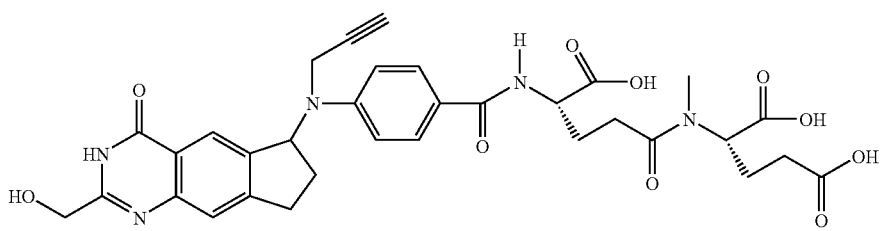

CB300960

Synthesis is as in Scheme 5.

4-{N-[(6RS)-2-Hydroxymethyl-4-oxo-3,4,7,8-tetrahydro-6H-cyclopenta[g]quinazolin-6-yl]-N-(prop-2-ynyl)amino}benzoic acid Method A: A solution of tert-butyl 4-{N-[(6RS)-2-(2,2-dimethyl-propionyloxymethyl)-4-oxo-3,4,7,8-tetrahydro-6H-cyclopenta[g]quinazolin-6-yl]-N-(prop-2-ynyl) amino}benzoate (0.150 g, 0.28 mmol) in dichloromethane (2 ml) and trifluoroacetic acid (6 ml) was stirred at room temperature for 1 hour. The solvents were then removed in vacuo, and the residue was suspended in methanol (3 ml) and water (5 ml). The pH was adjusted to ~10 with 1N NaOH (1.1 ml), and the mixture was stirred at room temperature for 4 hours. The reaction mixture was diluted with water (5 ml) and the pH was adjusted to ~5 with 1N HCl. The solid was then collected by filtration, but $^1$H-NNMR indicated no complete removal of the pivaloyl group. This solid was suspended into the filtrate and then 1N NaOH (0.9 ml, 0.9 mmol) was added (pH~12). The mixture was stirred at room temperature for 3.5 hours, then more 1N NaOH (0.2 ml) was added, and the mixture was stirred at room temperature for a further 0.5 hours. The pH was then adjusted to ~5.0 with 1N HCl. The off-white precipitate was collected by filtration, washed with water, and dried in vacuo over $P_2O_5$: 0.086 g, (79%); $^1$H-NMR (250 MHz, DMSO-$d_6$, TMS) 2.22 (m, 1H 7-CH), 2.90-3.30 (m, 3H, C≡CH, 8-H), g, 0.24 mmol), and anhydrous DMF (2.0 ml) was added diethyl cyanophosphonate (0.036 g, 0.22 mmol) with the aid of anhydrous DMF (0.2 ml) followed by triethylamine (0.022 g, 0.22 mmol). The clear solution was stirred at room temperature for 1.5 hours, then it was partitioned between ethyl acetate (50 ml) and brine (40 ml). The aqueous layer was extracted with more ethyl acetate (2×50 ml). The combined organics were washed with 10% aqueous citric acid (40 ml), saturated sodium bicarbonate solution (40 ml), and brine (40 ml), dried ($Na_2SO_4$), and concentrated in vacuo. Purification by column chromatography, on elution with a gradient of methanol in dichloromethane (0 to 6%), afforded an off-white solid that was further purified by trituration with hexane/dichloro-methane/diethyl ether: 0.062 g (40%); mp 116-120° C. (softens); $^1$H-NMR (250 MHz, DMSO-$d_6$, TMS) 1.36, 1.37, 1.38, 1.41 (4×s, 27H, 3×C($CH_3$)$_3$), 1.70-2.35 (m) and 2.50 (m obscured by DMSO peak) (10H, 2×β-$CH_2$, 2×γ-$CH_2$, 7-$CH_2$), 2.63, 2.82 (2×s, 3H, CONMe), 2.90-3.25 (m, 3H, C≡CH, 8-H), 3.97 (ABq, J=17.6 Hz, 2H, $CH_2$C≡C), 4.32 (m, 1H, glu α-CH), 4.38 (d, J=6.1 Hz, 2H, 2-$CH_2$), 4.50, 4.82 (2×dd, 1H, Meglu α-CH), 5.56 (t, J=6.9 Hz, 1H, $CH_2$OH), 5.78 (t, J=7.10 Hz, 1H, 6-H), 7.02 (d, J=8.6 Hz, 2H, 3',5'-H), 7.55 (s, 1H, 9-H), 7.78 (d, J=8.9 Hz, 2H, 2',6'-H), 7.82 (s, 1H, 5-H), 8.32 (m, 1H, CONH), 11.81 (s, 1H, $N^3$—H); MS (ES, m/z) 830{(M+H)$^+$, 100%}.

N-{N-{4-[N-((6RS)-2-hydroxymethyl-4oxo-3,4,7,8-tetrahydro-6H-cyclo-penta[g]quinazolin-6-yl)-N-(prop-2-ynyl)amino]benzoyl}-L-γ-glutamyl}-N-methyl-L-glutamic acid A solution of tri-tert-butyl N-{N-{4-[N-((6RS)-2-hydroxymethyl-4-oxo-3,4,7,8-tetrahydro-6H-cyclopenta[g]quinazolin-6yl)-N-(prop-2-ynyl)amino]-benzoyl}-L-γ-glutamyl}-N-methyl-L-glutamate (0.060 g, 0.07 mmol) in trifluoroacetic acid (3.5 ml) was stirred at room temperature for 1 hour and 10 min with protection from the light. The solvent was then removed in vacuo and the residue was suspended in water (6 ml). The pH was adjusted to ~10 with 1N NaOH, then to ~4 with 1N hydrochloric acid. The white precipitate was collected by filtration, and dried in vacuo over $P_2O_5$: 0.035 g (77%), mp >165° C. (dec); $^1$H-NMR (250 MHz, DMSO-$d_6$, TMS) 1.80-2.35 (m) and 2.50 (m obscured by DMSO peak) (10H, 2×β-$CH_2$, 2×γ-$CH_2$, 7-$CH_2$), 2.66, 2.83 (2×s, 3H, CONMe), 2.90-3.25 (m, 3H, C≡CH, 8-H), 3.97 (ABq, J=18.4 Hz, 2H, $CH_2$C≡C), 4.32 (m obscured, 1H, glu α-CH), 4.38 (d, J=5.6 Hz, 2H, 2-$CH_2$), 4.55, 4.91 (2×dd, J=10.0, 4.5 Hz, 1H, Meglu α-CH), 5.56 (poorly resolved t, 1H, $CH_2OH$), 5.77 (t, J=8.06 Hz, 1H, 6-H), 7.02 (d, J=7.8 Hz, 2H, 3',5'-H), 7.55 (s, 1H, 9-H), 7.81 (d, J=10.1 Hz, 3H, 2',6'-H, 5-H), 8.3 (m, 1H, CONH), 11.82 (s, 1H, $N^3$—H); MS (ESI, m/z) 662 {(M+H)$^+$, 100%}; Found: C, 57.52; H, 5.52; N, 10.17; $C_{33}H_{35}N_5O_{10}$ 1.5 $H_2O$ requires: C, 57.55; H, 5.56; N, 10.17%.

EXAMPLE 6 synthesis of 4-{N-[(6RS)-2-hydroxymethyl-4-oxo-3,4,7,8-tetra-hydro-6H-cyclopenta[g]quinazolin-6-yl]-N-(prop-2-ynyl)amino}benzoic acid

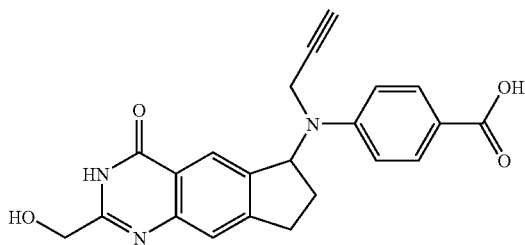

Synthesis is as in Scheme 6.

5-Amino-6-bromoindan-1-one

A solution of 5-acetamido-6-bromoindan-1-one (2.85 g, 10.60 mmol) in 48% HBr (90 ml) was placed in an oil bath preheated to 70° C. The mixture was stirred at this temperature for 1.5 h then cooled in an ice-bath and diluted with aqueous NaOH (1N, 50 ml). The pH was then adjusted to ~5 with aqueous NaOH (50% w/w). The brown solid was collected by filtration, washed with water, and dried in vacuo over $P_2O_5$. Purification by column chromatography, on elution with 8% AcOEt in $CH_2Cl_2$, gave an orange solid. This solid was triturated with 30% hexane in diethyl ether to obtain a pale brown solid (1.80 g, 75%), mp 209-211° C.; $^1$H-NMR (250 MHz, CDCl$_3$, TMS) 2.65 (m, 2H, 2-$CH_2$), 2.99 (m, 2H, 3-$CH_2$), 4.65 (br s, 2H, $NH_2$), 6.73, 7.86 (2 ×s, 1H each, 4-H and 7-H); MS (ESI, m/z) 226, 228 {(M+H)$^+$, bromine isotopic pattern}; Found: C, 47.59; H, 3.49; N, 6.11; Br, 35.16; $C_9H_8BrNO$ requires C, 47.82; H, 3.57; N, 6.20; Br, 35.34%.

2-Benzyloxy-N-(6-bromo-1-oxo-indan-5-yl)acetamide

To a stirred solution of 5-amino-6-bromoindan-1-one (1.70 g, 7.5 mmol) in anhydrous DMF (15 ml) was slowly added benzyloxyacetyl chloride (2.07 g, 11.25 mmol) followed by pyridine (3.0 ml, 37.5 mmol). The reaction mixture was stirred at room temperature for 18 h under argon and then partitioned between AcOEt (200 ml) and 1N HCl (150 ml). The aqueous layer was extracted with more AcOEt (100 ml) and the combined extracts were washed with 1N aqueous HCl (100 ml), and brine (100 ml), dried ($Na_2SO_4$), and concentrated in vacuo. Purification by column chromatography, on elution with 40% AcOEt in hexane and then 2% AcOEt in $CH_2Cl_2$/hexane (v/v, 9:1), afforded a yellow solid. This solid was reprecipitated from $CH_2Cl_2$/hexane to obtain a pale yellow solid (2.07 g, 75%); mp 120° C.; $^1$H-NMR (250 MHz, CDCl$_3$, TMS) 2.72 (m, 2H, 2-$CH_2$), 3.10 (m, 2H, 3-$CH_2$), 4.18, 4.72 (2×s, 2H each, PhCH$_2$ and OCH$_2$CO), 7.39 (m, 5H, PhCH$_2$), 7.95, 8.65 (2×s, 1H each, 4-H and 7-H), 9.39 (s, 1H, CONH); MS (ESI, m/z) 396, 398 {(M+Na)$^+$, ~50% each, bromine isotopic pattern}; 374, 376 {(M+H)$^+$, ~100% each, bromine isotopic pattern}; Found: C, 57.53; H, 4.23; N, 3.71; Br, 21.35; $C_{18}H_{16}BrNO_3$ requires C, 57.77; H, 4.31; N, 3.74; Br, 21.35%.

tert-Butyl 4-[N-(5-(2-benzloxyethanoylamino)-6bromoindan-1-yl)-amino]benzoate Method A: To a round-bottom flask containing 2-benzyloxy-N-(6-bromo-1-oxo-indan-5-yl)-acetamide (0.750 g, 2.0 mmol), 4-toluenesulfonic acid (0.030 g), tert-butyl 4-aminobenzoate (0.540 g, 2.8 mmol) was added anhydrous DME (distilled over CaH$_2$, 24 ml). An Aldrich azeotropic distillation apparatus containing molecular sieves (3A) was fitted to the reaction flask, which was then placed in an oil bath preheated to 115° C. The mixture was stirred at this temperature for 3.5 h under argon, then allowed to cool to room temperature. A solution of Na(CN)BH$_3$ in THF (1M, 2.8 ml, 2.8 mmol) was then added followed by AcOH (0.094 ml). The reaction mixture was stirred at room temperature for 2.5 h, then it was partitioned between AcOEt (200 ml) and saturated aqueous NaHCO$_3$ (150 ml). The aqueous layer was extracted with more AcOEt (100 ml) and the combined extracts were washed with brine (100 ml), dried ($Na_2SO_4$), and concentrated in vacuo. Purification by column chromatography, on elution with AcOEt/petroleum ether (v/v, 1:1), afforded a solid. This solid was reprecipitated from AcOEt/hexane to obtain the desired compound as a pale yellow solid (0.233 g, 21%); mp 150-151° C.; $^1$H-NMR (250 MHz, CDCl$_3$, TMS) 1.56 (s, 9H, C(CH$_3$)$_3$), 1.92, 2.63 (2×m, 1H each, 2-$CH_2$ indanyl), 2.82-3.00 (m, 2H, 3-$CH_2$ indanyl), 4.15, 4.71 (2×s, 2H each, PhCH$_2$ and OCH$_2$CO), 4.24 (d, J=8.12 Hz, 1H, $N^{10}$—H), 5.02 (m, 1H, 1-CH indanyl), 6.64 (d, J=8.73 Hz, 2H, 3,5-ArH), 7.39 (m, 5H, PhCH$_2$), 7.50, 8.33 (2×s, 1H each, 4-H and 7-H), 7.85 (d, J=8.7 Hz, 2H, 2,6-ArH), 9.06 (s, 1H, CONH); ESI, m/z) 575, 573 {(M+Na)$^+$, 100%, 98%, bromine isotopic pattern}; Found: C, 63.03; H, 5.65; N, 5.04; Br, 14.46; $C_{29}H_{31}BrN_2O_4$ requires C, 63.16; H, 5.67; N, 5.08; Br, 14.49%.

Method B: To a nearly clear solution of 2-benzyloxy-N-(6-bromo-1-oxo-indan-5-yl)-acetamide (0.540 g, 1.44 mmol) in anhydrous methanol (45 ml) and CH$_2$Cl$_2$ (10 ml) was added tert-butyl 4-aminobenzoate (0.305 g, 1.58 mmol) followed by decaborane (0.055 g). The reaction mixture was stirred at room temperature overnight before being concentrated in vacuo. Purification by column chromatography, on elution with 40% ethyl acetate in petroleum ether (60-80° C.), afforded the desired product: 0.66 g, (84%).

tert-Butyl 4-[N-(5-(2-benzyloxyethanoylamino)-6-cyanoindan-1-yl)-amino]benzoate To a stirred solution of tert-butyl 4-[N-(5-(2-benzyloxyethanoylamino)-6-bromoindan-1-yl)amino]benzoate (0.210 g, 0.38 mmol) in anhydrous NMP (2.2 ml) was added CuCN (0.068 g, 0.76 mmol). The reaction flask was placed in an oil bath preheated to 150° C. and it was stirred at this temperature for 3 h under argon. The mixture was then allowed to cool to room temperature and poured into a mixture of liquid ammonia (d=0.88, 2 ml) and ice-water (5 ml). This mixture was stirred at room temperature for 5 min, the brown precipitate was then collected by filtration and washed with water. This precipitate was then suspended in $CH_2Cl_2$ (70 ml), dried ($Na_2SO_4$), and concentrated in vacuo. Purification of the residue by column chromatography, on elution with 35% AcOEt in hexane, afforded a brown solid (0.084 g, 45%); mp 194-195° C.; $^1$H-NMR (250 MHz, $CDCl_3$, TMS) 1.55 (s, 9H, $C(CH_3)_3$), 1.95, 2.64 (2×m, 1H each, 2-$CH_2$ indanyl), 2.99 (m, 2H, 3-$CH_2$ indanyl), 4.13, 4.72 (2×s, 2H each, $PhCH_2$ and $OCH_2CO$), 4.22 (d, J=8.1 Hz, 1H, $N^{10}$—H), 5.05 (m, 1H, 1-CH indanyl), 6.65 (d, J=8.7 Hz, 2H, 3,5-ArH), 7.39 (m, 5H, $PhCH_2$), 7.54, 8.37 (2×s, 1H each, 4-H and 7-H), 7.86 (d, J=8.7 Hz, 2H, 2,6-ArH), 9.06 (s, 1H, CONH); MS (ESI, m/z) 520 {(M+Na)$^+$, 100%,}; Found: C, 72.26; H, 6.26; N, 8.41; $C_{30}H_{31}N_3O_4$ requires C, 72.41; H, 6.28; N, 8.44%.

tert-Butyl 4-{N-[(6RS)-2-benzyloxymethyl-4-oxo-3,4,7,8-tetrahydro-6H-cyclopenta[g]quinazolin-6-yl]amino}benzoate To a stirred, ice-bath cooled mixture of tert-butyl 4-[N-(5-(2-benzyloxy-ethanoylamino)-6-cyanoindan-1-yl)amino] benzoate (3.77 g, 7.59 mmol), EtOH (70 ml), and $H_2O$ (11 ml) was added 30% $H_2O_2$ (8.05 ml) followed by granulated NaOH pellets (0.640 g, 16.0 mmol). The reaction mixture was stirred at 0° C. for 10 min, then placed in an oil-bath preheated to 55° C. and stirred at this temperature for 1 hour. The solvents were then removed in vacuo; the residue was treated with $H_2O$ (80 ml) and the pH was adjusted to ~5 with 1N HCl. The pale yellow solid was collected by filtration, washed with $H_2O$ and dried in vacuo over $P_2O_5$ (3.56 g, 95%); mp 194-195° C.; $^1$H-NMR (250 MHz, DMSO-$d_6$, TMS) 1.52 (s, 9H, $C(CH_3)_3$), 1.90 (m), 2.62 (m) (1H each, 7-CH), 2.90-3.17 (m, 2H, 8-$CH_2$), 4.43, 4.60 (2×s, 2H each, $PhCH_2$ and $OCH_2CO$), 5.18 (q, J=7.43 Hz, 1H, 6-CH), 6.79 (d, J=8.8 Hz, 2H, 3',5'-ArH), 6.87 (d, J=8.0 Hz, 1H, $N^{10}$—H), 7.34 (m, 5H, $PhCH_2$), 7.54, 7.92 (2×s, 1H each, 5-H and 9-H), 7.68 (d, J=8.9 Hz, 2H, 2',6'-ArH), 12.20 (s, 1H, CONH); MS (ESI, m/z) 520 {(M+Na)$^+$, 90%,}, 498 {(M+H)$^+$, 100%}; Found: C, 72.13; H, 6.25; N, 8.38; $C_{30}H_{31}N_3O_4$ requires C, 72.41; H, 6.28; N, 8.44%.

tert-Butyl 4-{N-[(6RS)-2-hydroxymethyl-4-oxo-3,4,7,8-tetrahydro-6H-cyclopenta[g]quinazolin-6-yl]amino}benzoate To a solution of tert-butyl 4-{N-[(6RS)-2-benzyloxymethyl-4-oxo-3,4,7,8-tetrahydro-6H-cyclopenta[g]quinazolin-6-yl]amino}benzoate (1.40 g, 2.8 mmol) in EtOH (150 ml) was added 10% Pd/C (0.665 g). The mixture was stirred at 45° C. for 3 h, then more catalyst (0.200 g) was added and stirring was continued at 50° C. for 6 h. The catalyst was removed by filtration, washed with EtOH, and the filtrate was concentrated in vacuo. Purification of the residue by column chromatography, on elution with 8% methanol in ethyl acetate, gave a white solid (0.679 g, 60%); mp 265-266° C.; $^1$H-NMR (250 MHz, DMSO-$d_6$, TMS) 1.52 (s, 9H, $C(CH_3)_3$), 1.88, 2.57 (2×m, 1H each, 7-CH), 2.90-3.17 (m, 2H, 8-$CH_2$), 4.38 (d, J=6.0 Hz, 2H 2-$CH_2OH$), 5.17 (m, 1H, 6-CH), 5.54 (t, J=6.1 Hz, 1H, $CH_2OH$), 6.79 (d, J=8.8 Hz, 2H, 3',5'-ArH), 6.91 (d, J=7.8 Hz, $N^{10}$—H), 7.51, 7.91 (2×s, 1H each, 5-H and 9-H), 7.68 (d, J=8.8 Hz, 2H, 2',6'-ArH), 11.83 (s, 1H, CONH); MS (ESI, m/z) 408 [M+H]$^+$, 65%], 352 [(M-tBu)$^+$, 100%], 215 (60%); Found: C, 67.41; H, 6.20; N, 10.17; $C_{23}H_{25}N_3O_4$ requires C, 67.80; H, 6.18; N, 10.31%.

(Propargyl)$Co_2(CO)_6^+BF_4^-$

This was prepared as in Example 1 from the dicobalt hexacarbonyl propargyl alcohol complex. It was immediately used in the next reaction without any further purification.

tert-Butyl 4-{N-[(6RS)-2-hydroxymethyl-4-oxo-3,4,7,8-tetrahydro-6H-cyclopenta[g]quinazolin-6yl]-N-(prop-2-ynyl)amino}benzoate To a round-bottomed flask containing the salt (propargyl)$Co_2(CO)_6^+BF_4^-$ (0.390 g, 0.95 mmol) under argon was added anhydrous dichloromethane (dried by distillation over $P_2O_5$; 14 ml), a nearly clear solution was obtained. To this solution a suspension of tert-butyl 4-{N-[(6RS)-2-hydroxymethyl-4-oxo-3,4,7,8-tetrahydro-6H-cyclopenta[g]quinazolin-6-yl]amino}benzoate (0.285 g, 0.71 mmol) in anhydrous $CH_2Cl_2$ (14 ml) and DME (distilled over $CaH_2$, 20 ml) was added in one portion. The mixture was stirred at room temperature for 10 min under argon, then diisopropylethylamine (0.14 ml) was added and stirring was continued at room temperature for 20 min. The reaction mixture was then partitioned between AcOEt (350 ml) and brine (100 ml). The organic layer was washed with 10% aqueous citric acid (100 ml), and brine (100 ml), dried ($Na_2SO_4$), and concentrated in vacuo. Purification by chromatography (FlashMaster personal system by Jones Chromatography, isolute 20 g-70 ml column), on elution with 70% AcOEt in $CH_2Cl_2$, gave a red solid (0.391 g, 76%), mp 190° C. (dec); $^1$H-NMR (250 MHz, DMSO-$d_6$, TMS) 1.52 (s, 9H, $C(CH_3)_3$), 2.24, 2.60 (2×m, 1H each, 7-CH), 2.96-3.25 (m, 2H, 8-$CH_2$), 4.37 (d, J=5.90 Hz, 2H 2-$CH_2OH$), 4.65 (ABq, J=17.2 Hz, 2H, $N^{10}$—$CH_2$), 5.55 (t, J=6.2 Hz, 1H, $CH_2OH$), 5.80 (t, J=7.7 Hz, 1H, 6-CH), 6.68 (s, 1H, propargyl H), 7.01 (d, J=8.8 Hz, 2H, 3',5'-ArH), 7.56, 7.76 (2×s, 1H each, 5-H and 9-H), 7.79 (d, J=9.8 Hz, 2H, 2',6'-ArH), 11.83 (s, 1H, CONH). To a solution of this material (0.380 g, 0.52 mmol) in EtOH (65 ml) was added Fe(NO$_3$)$_3$ 9$H_2O$ (2.60 g, 6.5 mmol). The mixture was stirred at room temperature for 2.5 h, brine (~200 ml) was then added into the reaction mixture that was then extracted with AcOEt (3×150 ml). The combined organic extracts were washed with brine (120 ml), dried ($Na_2SO_4$), and concentrated in vacuo. Purification by column chromatography, on elution with 5% MeOH in AcOEt, gave an off-white solid (0.161 g, 705), mp 195-197° C.; $^1$H-NMR (250 MHz, DMSO-$d_6$, TMS) 1.52 (s, 9H, $C(CH_3)_3$), 2.17 (m), 2.55 (m obscured by the DMSO peak) (1H each, 7-CH), 2.90-3.20 (m, 3H, C≡CH, 8-$CH_2$), 3.98 (ABq, J=18.7 Hz, 2H, $N^{10}$—$CH_2$), 4.38 (d, J=5.8 Hz, 2H 2-$CH_2OH$), 5.56 (t, poorly resolved, 1H, $CH_2OH$), 5.78 (t, J=8.7 Hz, 1H, 6-CH), 7.02 (d, J=9.0 Hz, 2H, 3',5'-ArH), 7.55, 7.80 (2×s, 1H each, 5H and 9-H), 7.76 (d, J=9.8 Hz, 2H, 2',6'-ArH), 11.82 (s, 1H, CONH); MS (ESI, m/z) 468 [(M+Na)+, 60%], 446 [(M+H)+, 50%], 390 [(M-tBu)+, 70%], 215 (100%); Found: C, 69.63; H, 6.13; N, 9.31; $C_{26}H_{27}N_3O_4$ requires C, 70.09; H, 6.11; N, 9.43%. FAB-HRMS, measured: 445.2017, calculated for $C_{26}H_{27}N_3O_4$ ($M^+$): 445.2002.

4-{N-[(6RS)-2-Hydroxymethyl-4-oxo-3,4,7,8-tetrahydro-6H-cyclopenta-[g]quinazolin-6-yl]-N-(prop-2-ynyl)amino}benzoate acid A solution of tert-butyl 4-{N-[(6RS)-2-hydroxymethyl-4-oxo-3,4,7,8-tetra-hydro-6H-cyclopenta[g]quinazolin-6-yl]-N-(prop-2-ynyl)amino}benzoate (0.050 g, 0.11 mmol) in $CH_2Cl_2$ (1 ml) and TFA (2.4 ml) was stirred at room temperature for 1 h. The solvents were then removed in vacuo, and the residue was triturated with diethyl ether. The white precipitate was collected by filtration, washed with diethyl ether and dried in vacuo over $P_2O_5$ to obtain the desired compound as the trifluoroacetate salt (0.044 g); $^1$H-NMR (250 MHz, DMSO-$d_6$, TMS) 2.26 (m), 2.55 (m obscured by the DMSO peak) (1H each, 7-CH), 2.90-3.15 (m, 3H, C≡CH, 8-$CH_2$), 4.02 (ABq, J=18.6 Hz, 2H, $N^{10}$—$CH_2$), 4.42 (s, 2H 2-$CH_2OH$), 5.78 (t, J=8.3 Hz, 1H, 6-CH), 7.03 (d, J=9.0 Hz, 2H, 3',5'-ArH), 7.60, 7.83 (2×s, 1H each, 5H and 9-H), 7.81 (d, J=8.5 Hz, 2H, 2',6'-ArH); MS (ESI m/z) 412 [(M+Na)+, 15%], 390 [(M+H)+, 30%], 215 (100%).

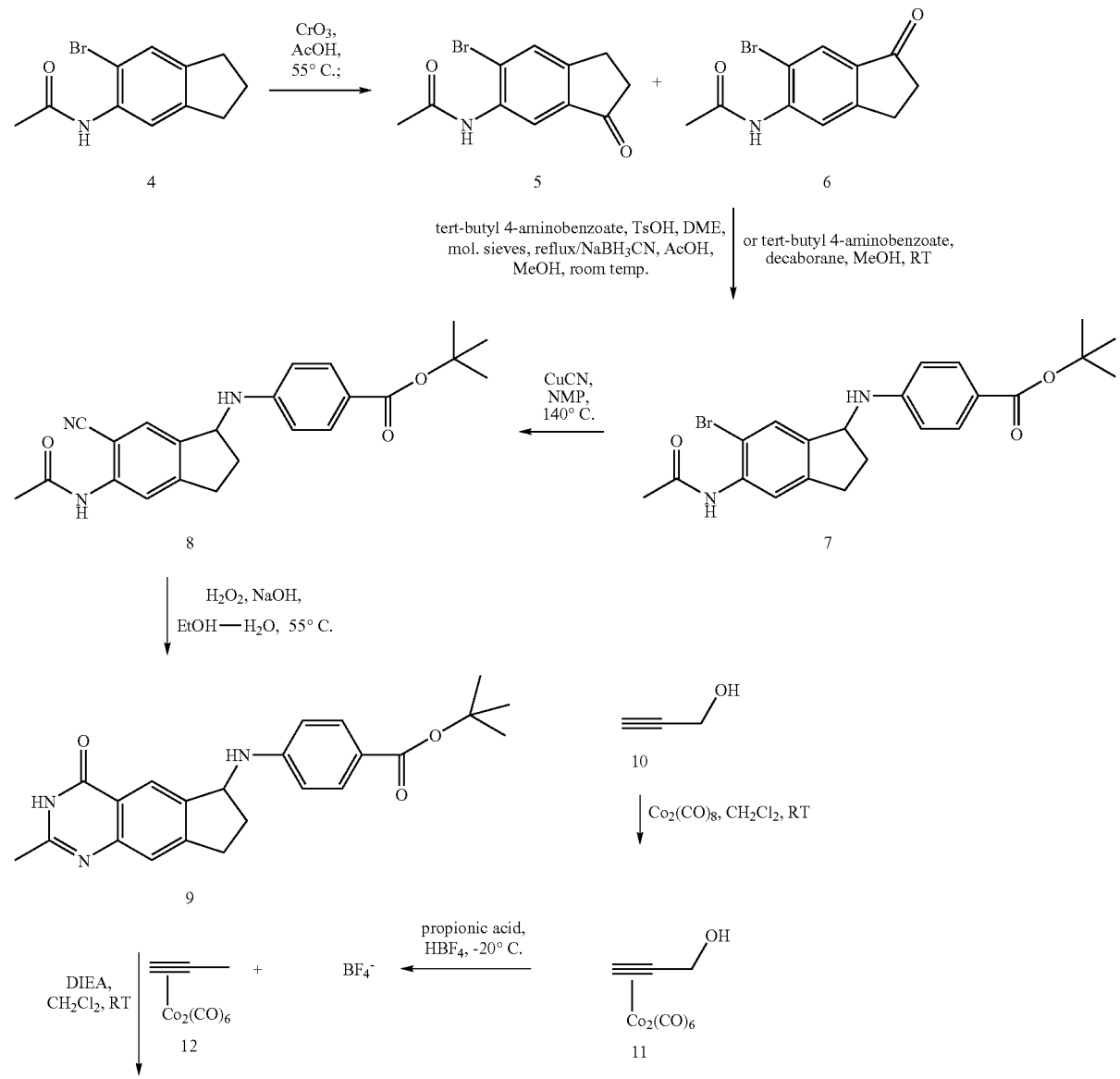

Scheme 1:

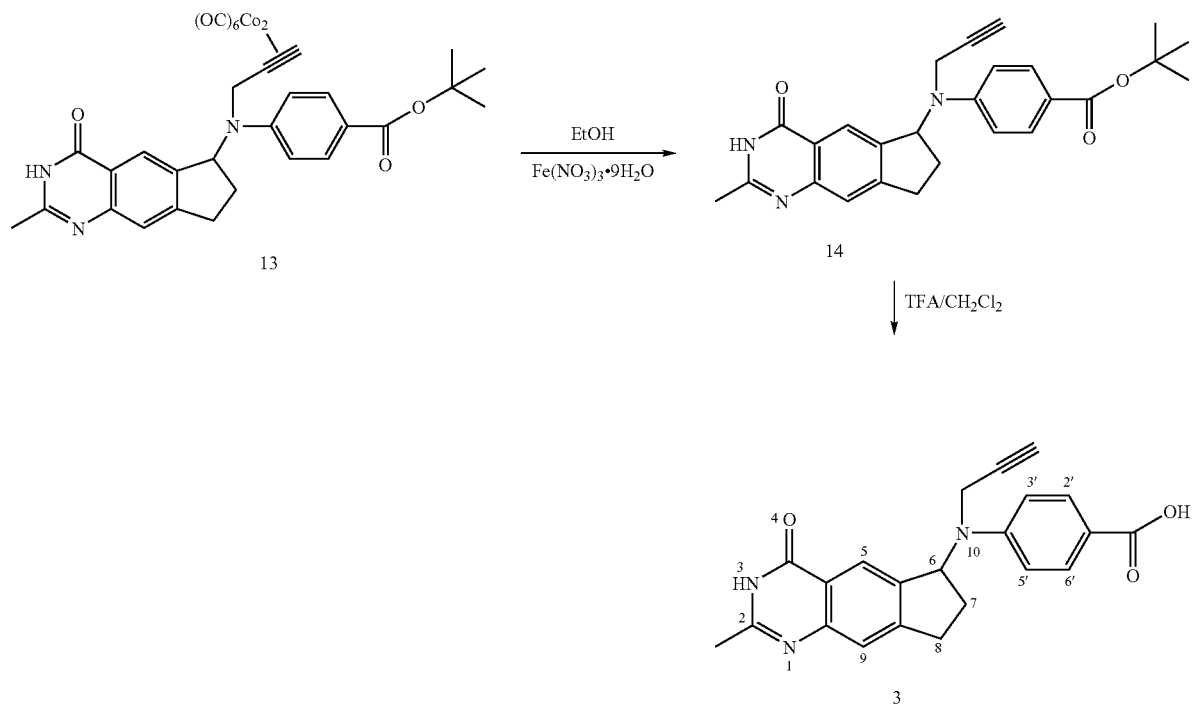
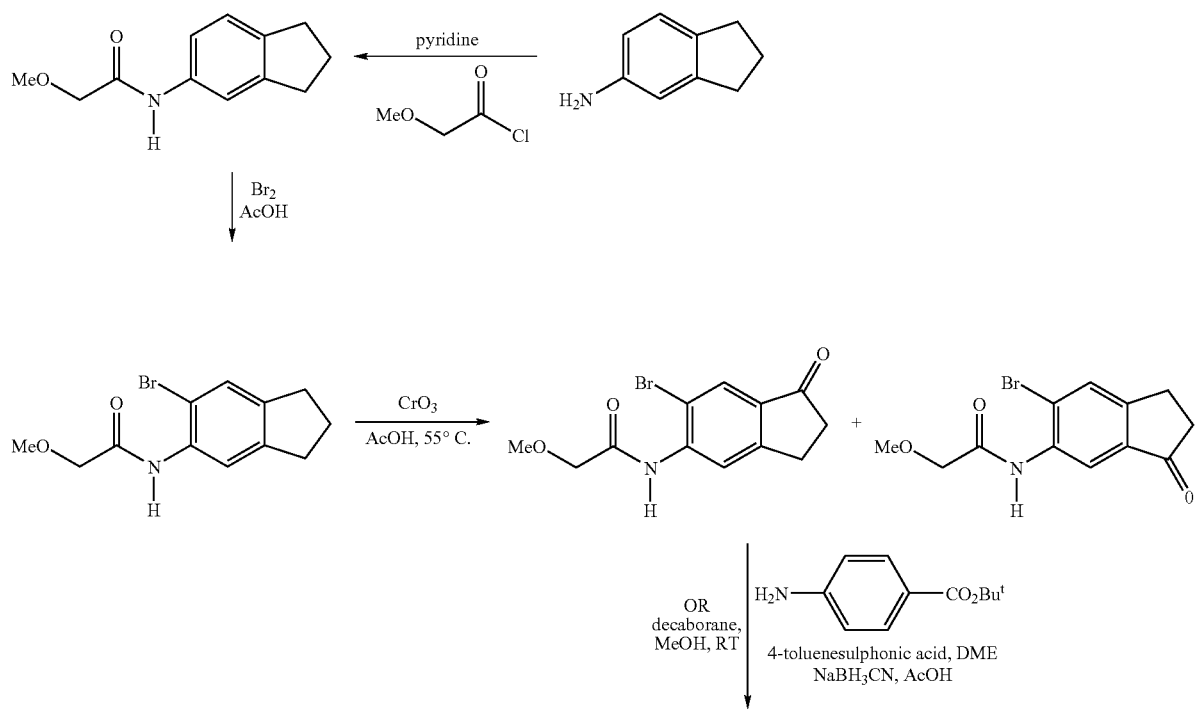

-continued
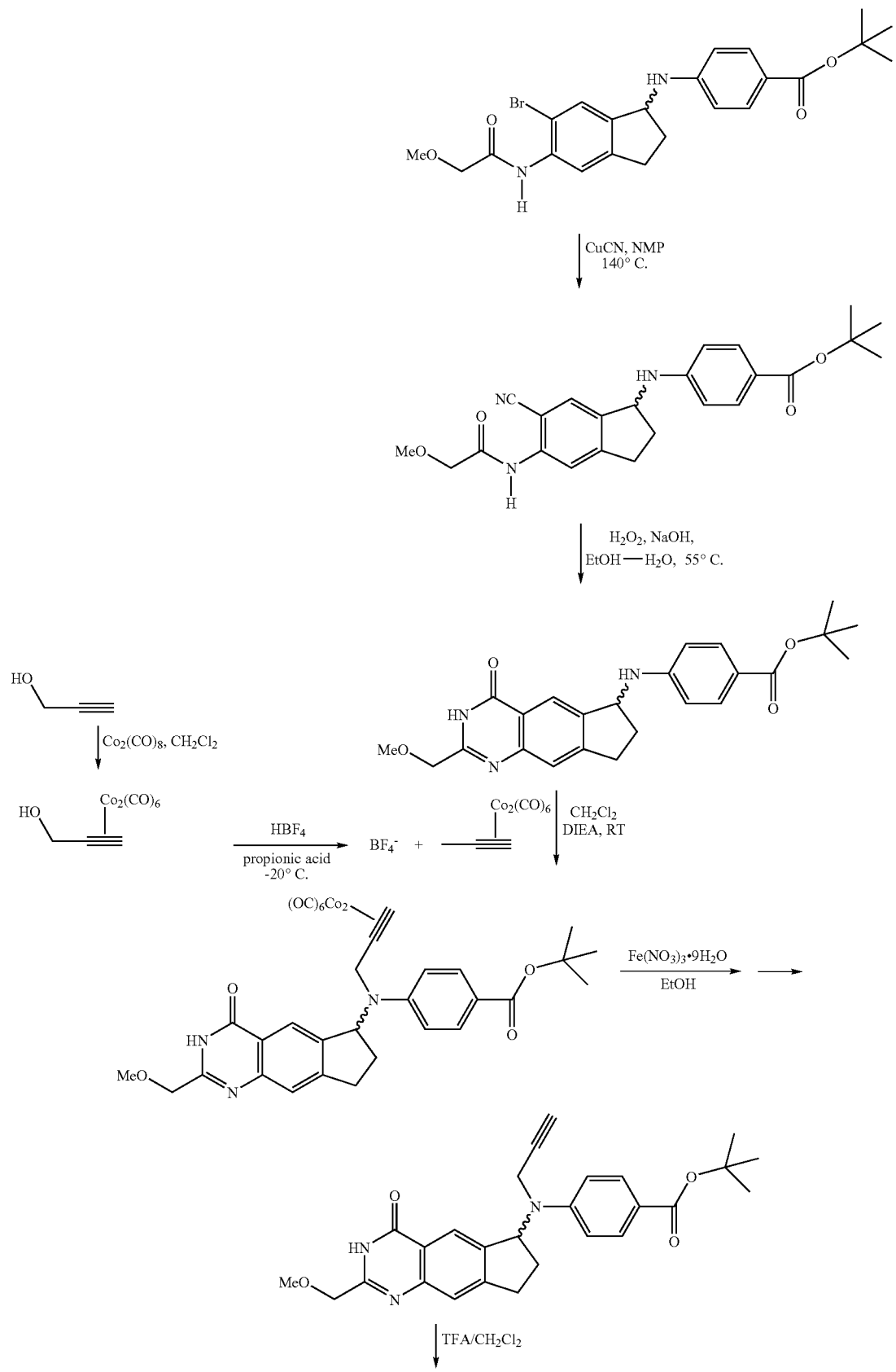

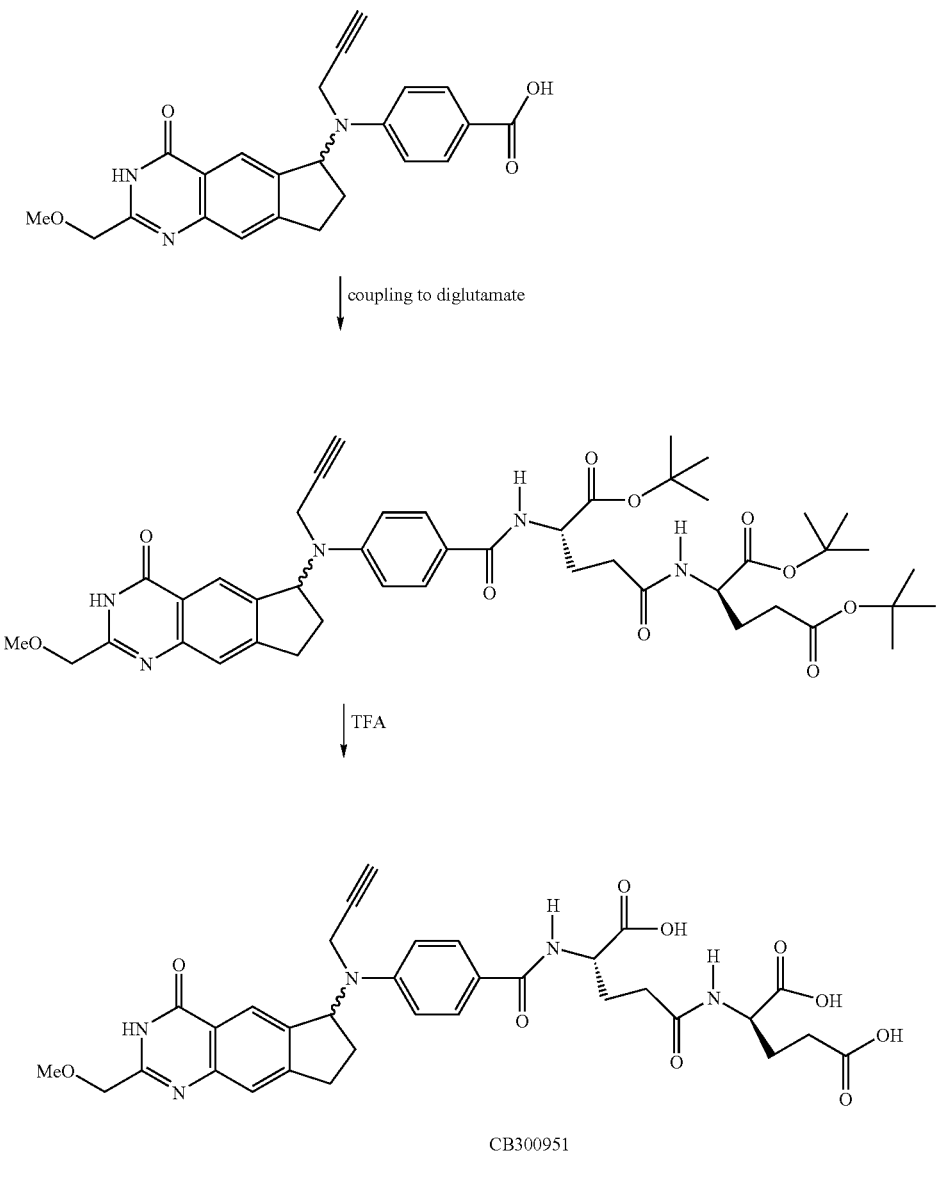
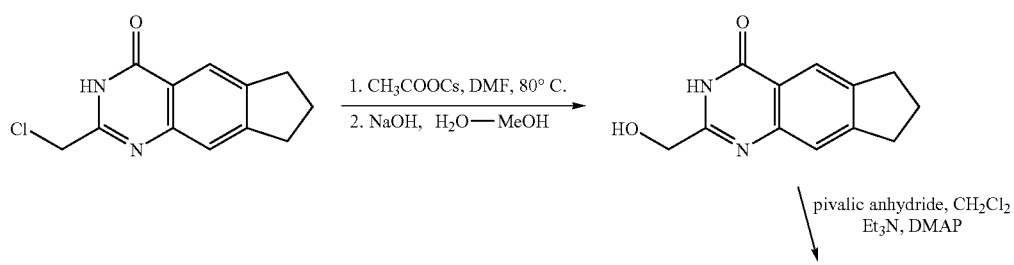
Scheme 3: Synthesis of CB300945

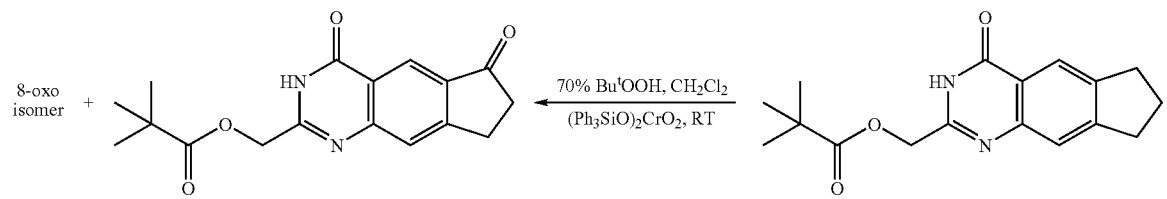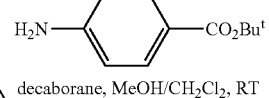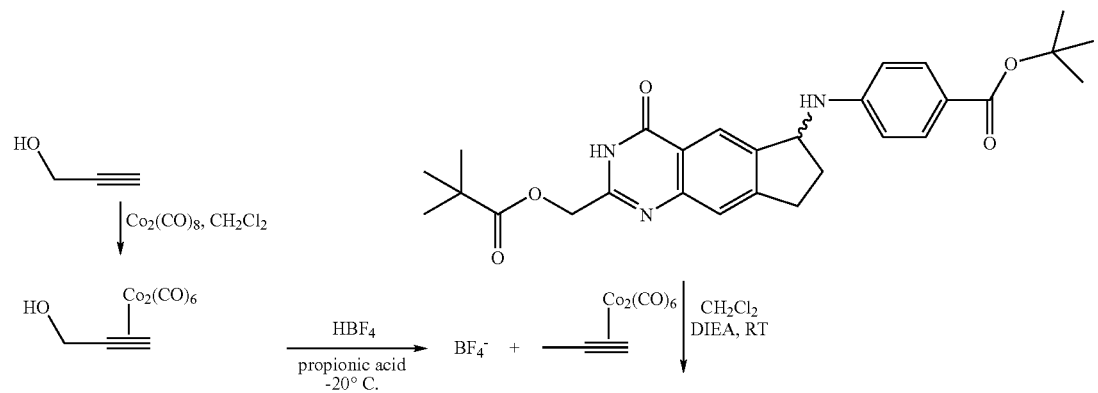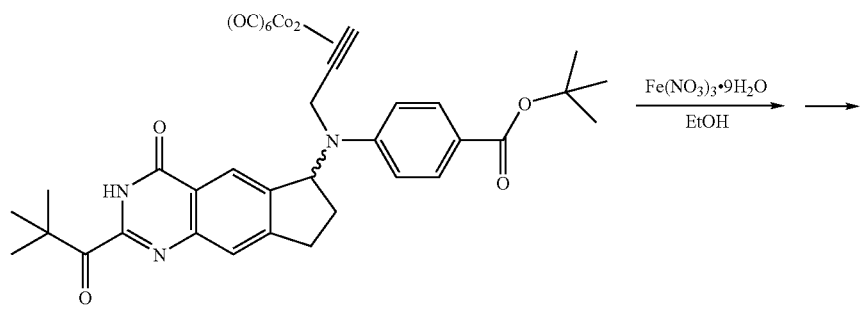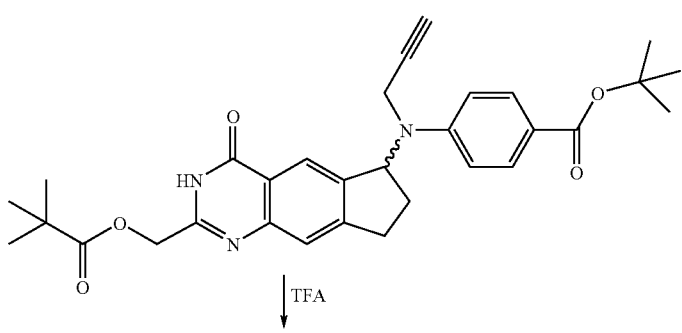

-continued
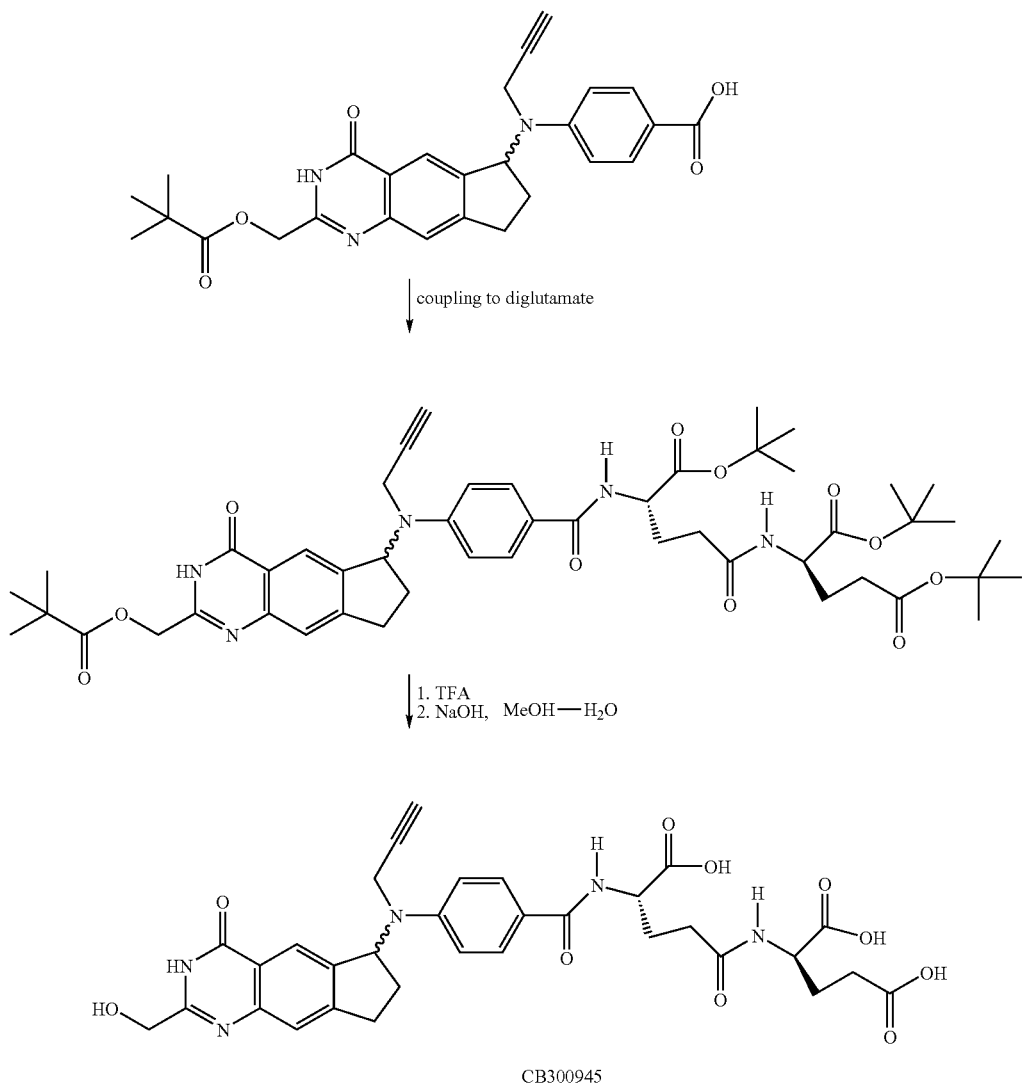
CB300945
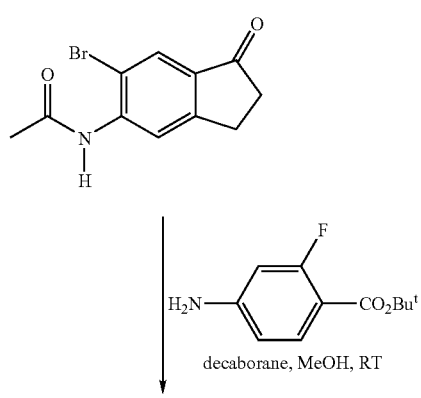

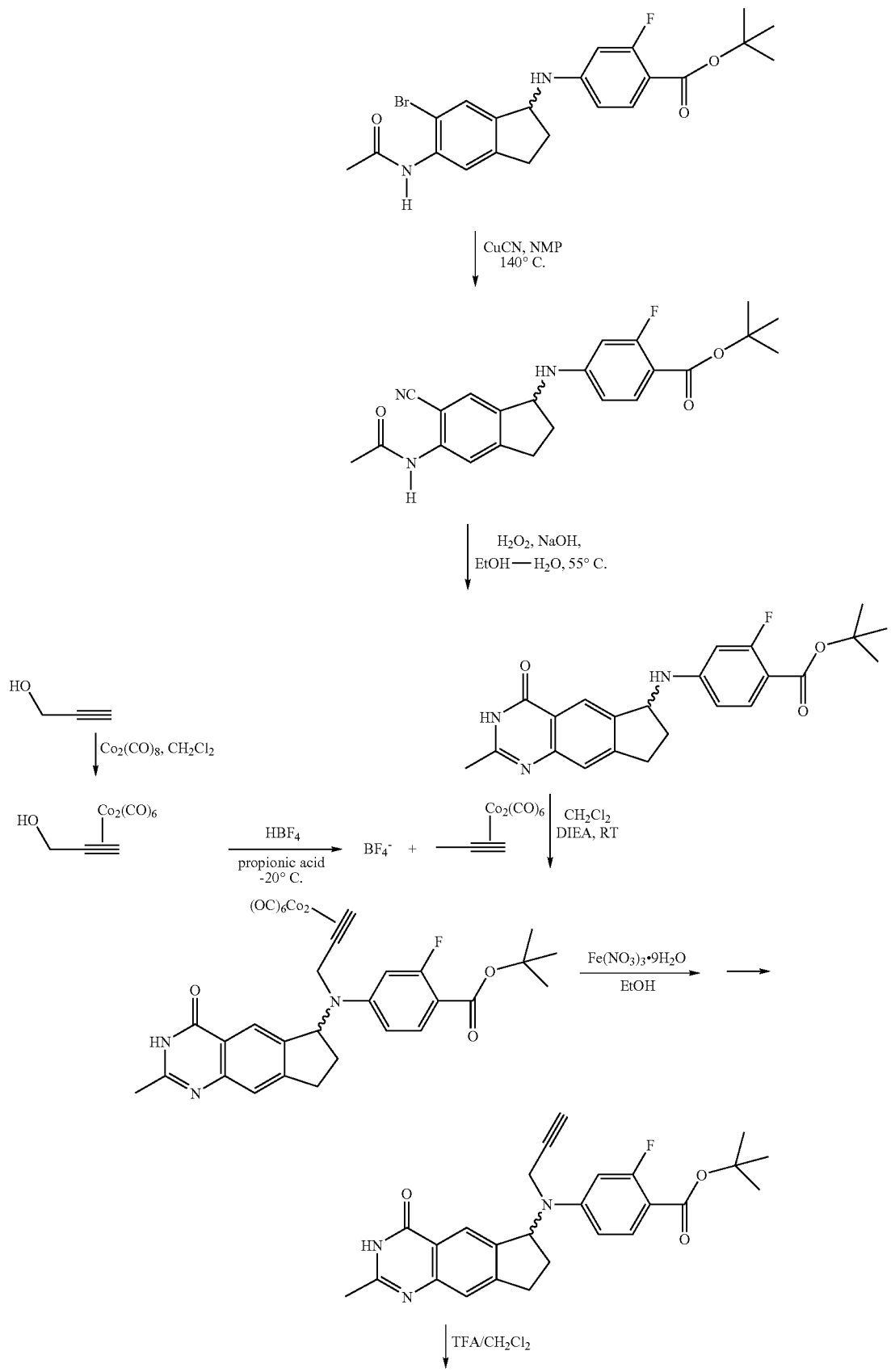

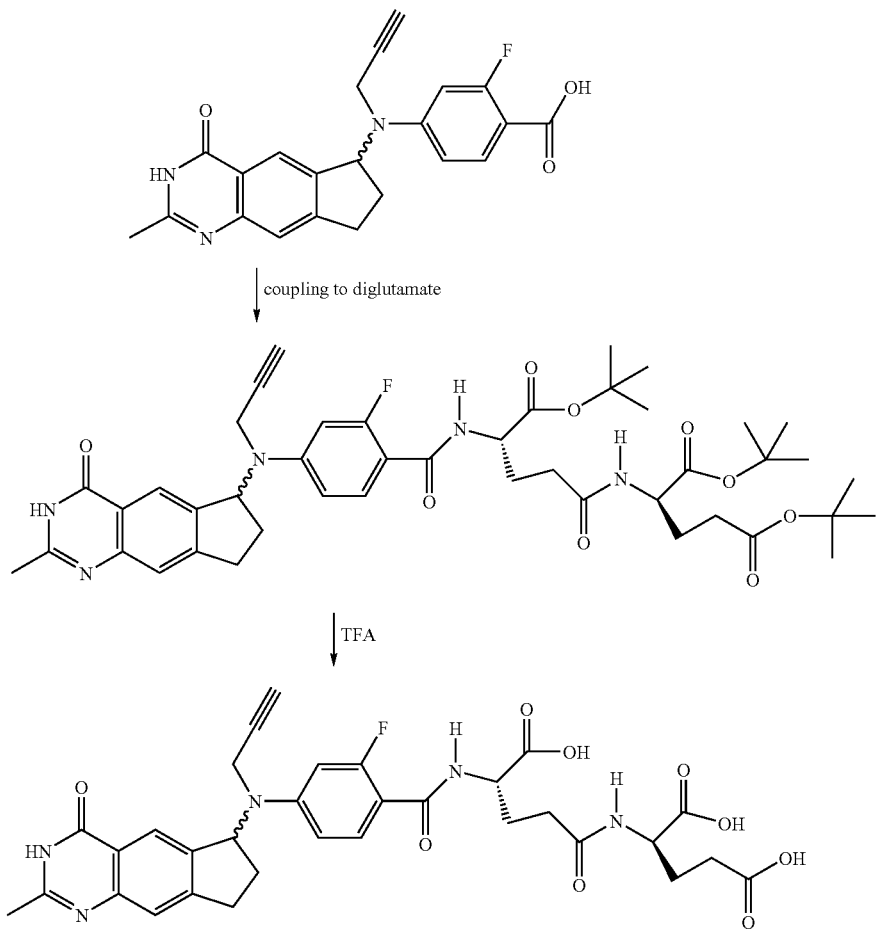
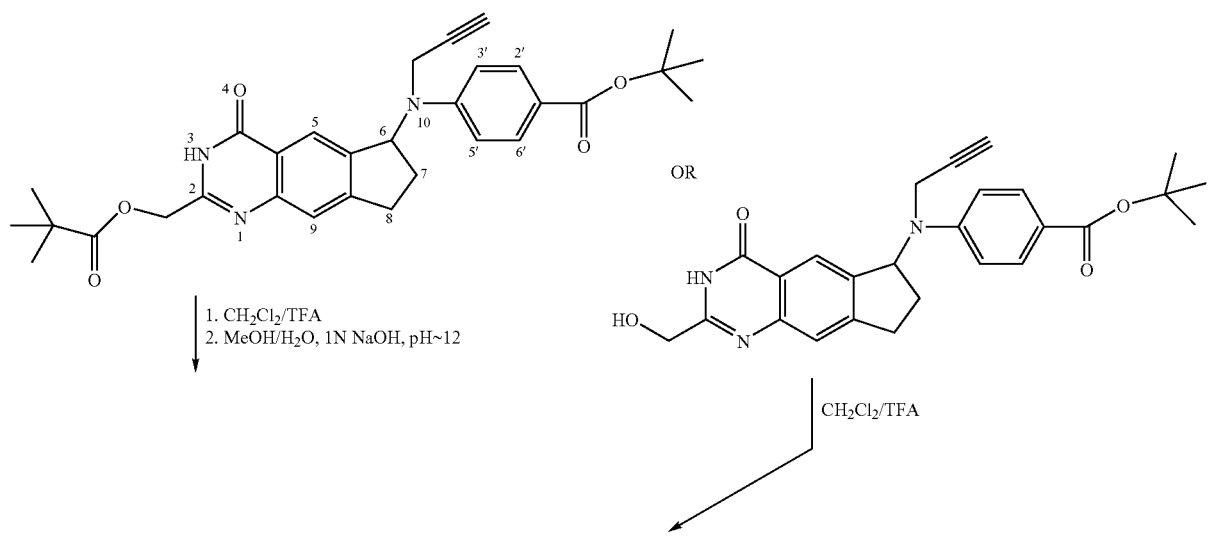
Scheme 5: Synthesis of CB300960

51 52
-continued
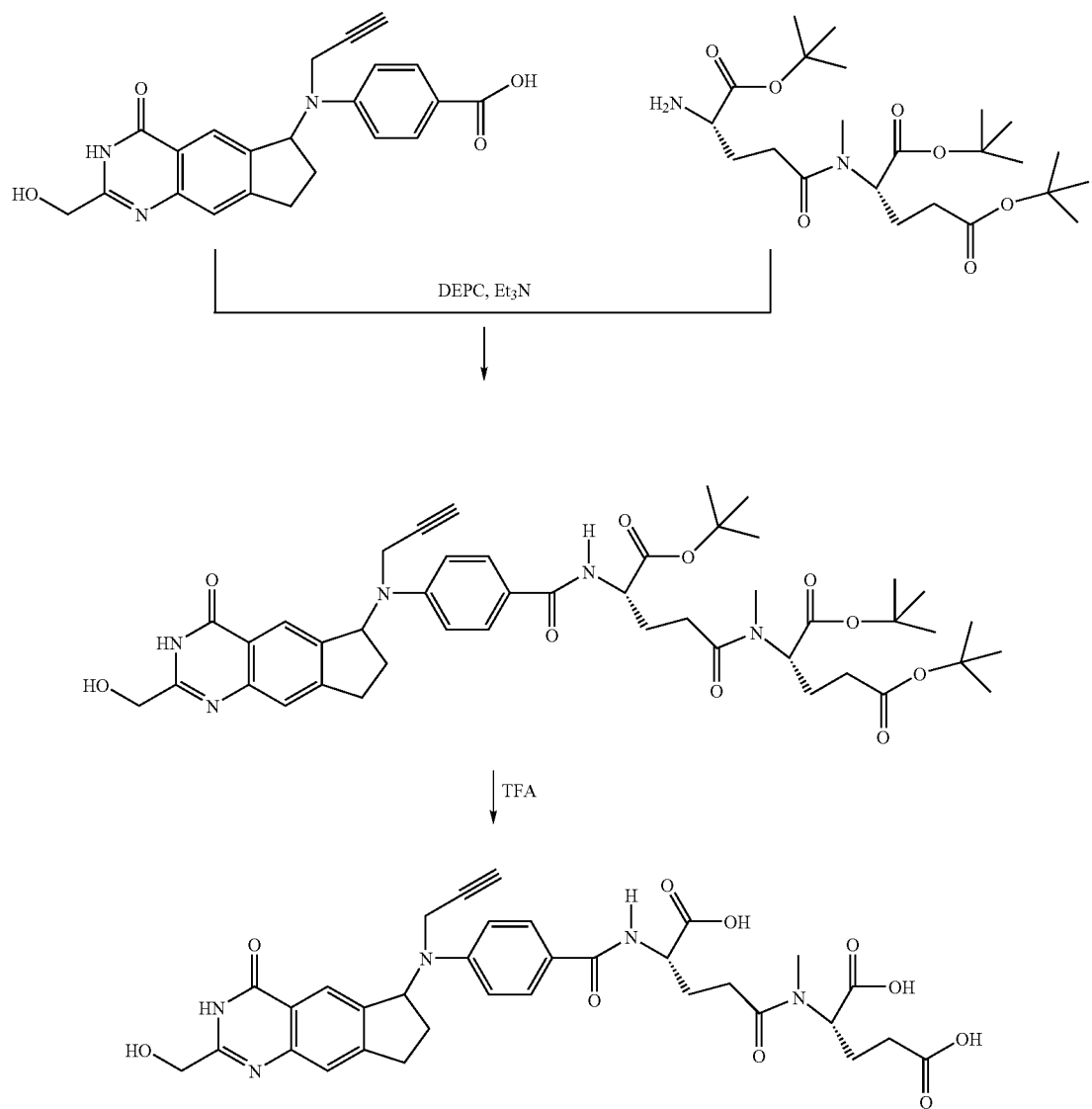
Scheme 6:
NEW ROUTE TO ⇒
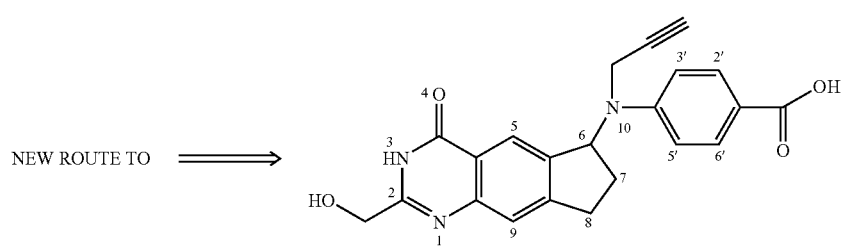

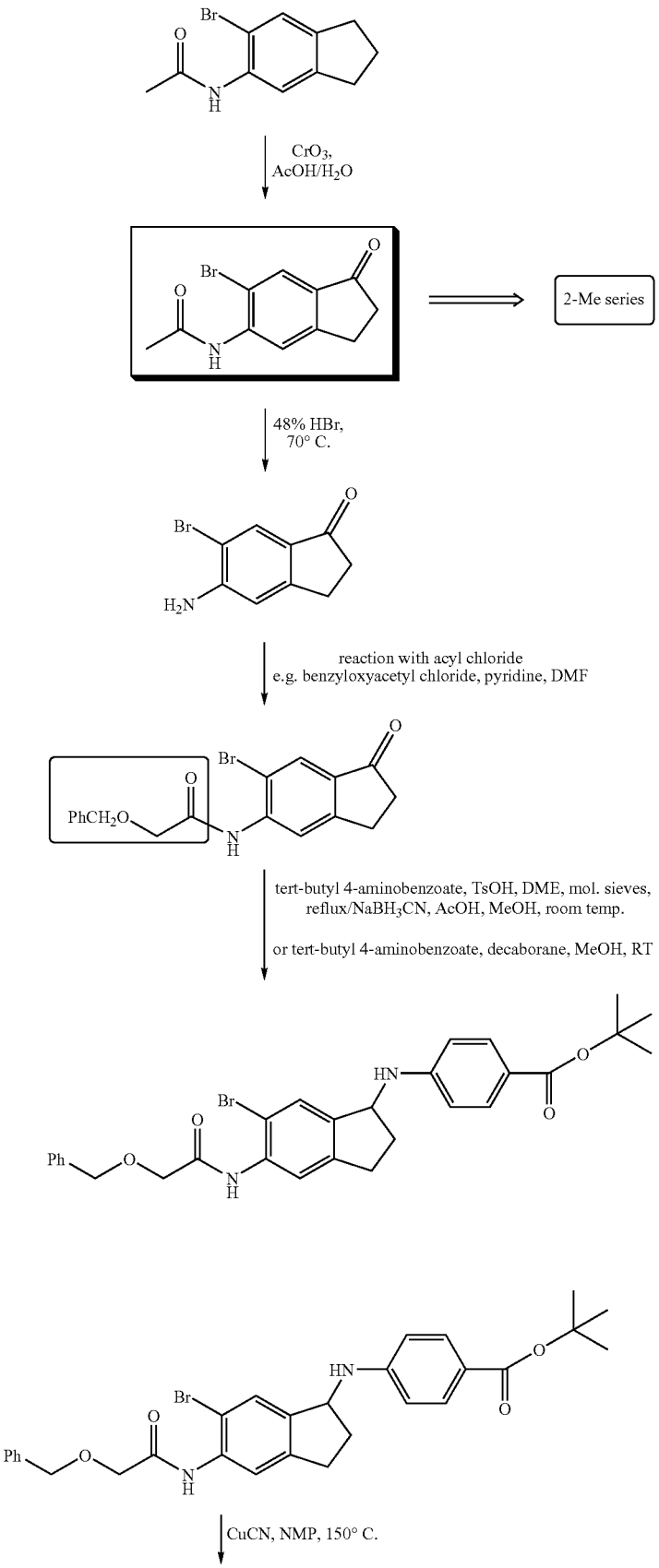
Scheme 6:
ROUTE B:

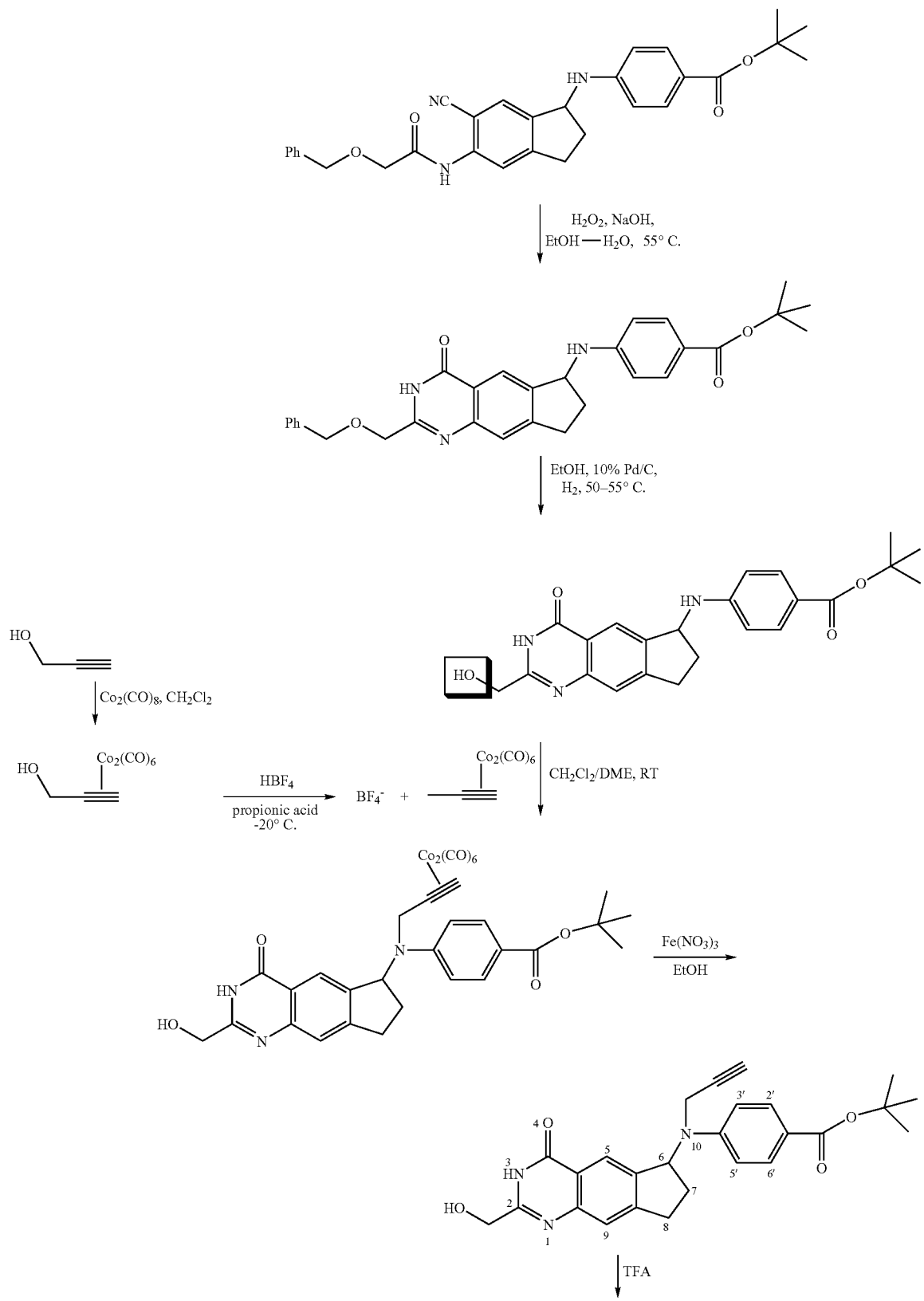

-continued

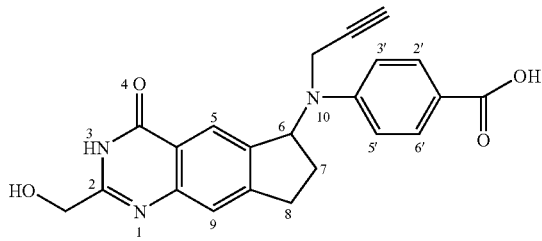

The invention claimed is:
1. A compound of formula (V):

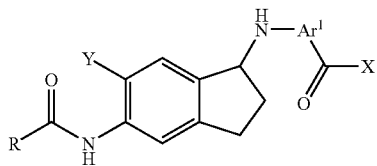

wherein:
R is hydrogen, $C_{1-4}$ alkyl, $C_{2-4}$ alkenyl, $C_{2-4}$ alkynyl, $C_{1-4}$ halogenoalkyl or $C_{1-4}$ cyanoalkyl; or
R is a group $A(CH_2)_p$ where A is $R^OO$ or $R^OR^1N$ wherein $R^O$ and $R^1$ are each independently hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl, or $R^O$ and $R^1$ together with the intermediate N form a five-or six-membered heterocyclic ring and p is an integer in the range 0 to 4; and
$Ar^1$ is phenylene or pyrimidinediyl which may optionally bear one or two substituents selected from halogeno, hydroxy, amino, nitro, cyano, trifluoromethyl, $C_{1-4}$ alkyl and $C_{1-4}$ alkoxy;
X is an alkoxy, aryloxy or optionally substituted amino group;
Y is CN or a leaving group selected from Br, Cl and I;
or a protected derivative thereof.

2. A process for the preparation of a cyclopenta[g] quinazoline of formula (I):

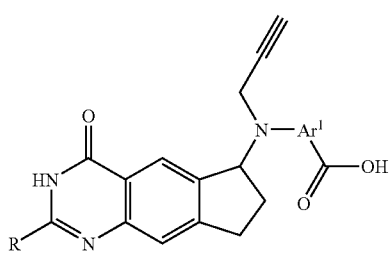

wherein:
R is hydrogen, $C_{1-4}$ alkyl, $C_{2-4}$ alkenyl, $C_{2-4}$ alkynyl, $C_{1-4}$ halogenoalkyl or $C_{1-4}$ cyanoalkyl; or
R is a group $A(CH_2)_p$ where A is $R^OO$ or $R^OR^1N$ wherein $R^O$ and $R^1$ are each independently hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl, or $R^O$ and $R^1$ together with the intermediate N form a five-or six-membered heterocyclic ring and p is an integer in the range 0 to 4; and
$Ar^1$ is phenylene, or pyrimidinediyl which may optionally bear one or two substituents selected from halogeno, hydroxy, amino, nitro, cyano, trifluoromethyl, $C_{1-4}$ alkyl and $C_{1-4}$ alkoxy;
or an ester or amide thereof;
including the step of reacting an ester or amide of formula (II):

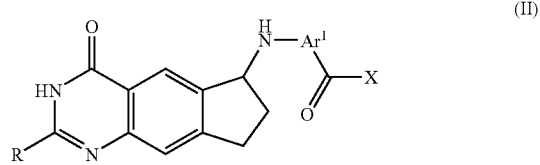

wherein R and $Ar^1$ are as defined above and X is an alkoxy, aryloxy or optionally substituted amino group;
or a protected derivative thereof;
with a complex containing the (propargyl)$Co^2(CO)_6^+$ ion.

3. A process as claimed in claim 2 wherein the complex containing the (propargyl)$Co_2(CO)_6^+$ ion is the tetrafluoroborate salt of formula (propargyl)$Co_2(CO)_6^+$ $BF_4^-$.

4. A process as claimed in claim 2 wherein the reaction is performed in an anhydrous organic solvent in a presence of a base.

5. A process as claimed in claim 2 wherein the reaction is performed at temperatures ranging between −30° C. to room temperature under argon.

6. A process as claimed in claim 2 wherein the ester or amide of formula (II) is made by ring-closing a compound of formula (III):

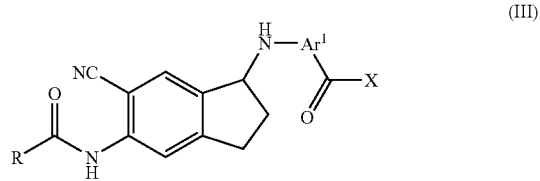

or a protected derivative thereof.

7. A process for the preparation of a cyclopenta[g] quinazoline of formula (I):

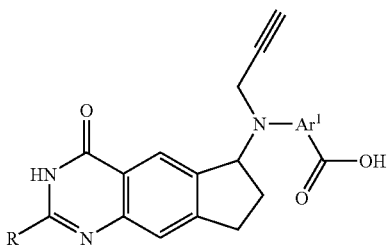

(I)

wherein:

R is hydrogen, $C_{1-4}$ alkyl, $C_{2-4}$ alkenyl, $C_{2-4}$ alkynyl, $C_{1-4}$ halogenoalkyl or $C_{1-4}$ cyanoalkyl; or R is a group $A(CH_2)_p$ where A is $R^0O$ or $R^0 R^1N$ wherein $R^0$ and $R^1$ are each independently hydrogen, $C_{1-4}$ alkyl, $C_{3-4}$ alkenyl, $C_{3-4}$ alkynyl, $C_{2-4}$ hydroxyalkyl, $C_{2-4}$ halogenoalkyl or $C_{1-4}$ cyanoalkyl, or $R^0$ and $R^1$ together with the intermediate N form a five- or six-membered heterocyclic ring and p is an integer in the range 0 to 4; and $Ar^1$ is phenylene or pyrimidinediyl which may optionally bear one or two substituents selected from halogeno, hydroxy, amino, nitro, cyano, trifluoromethyl, $C_{1-4}$ alkyl and $C_{1-4}$ alkoxy;

or an ester or amide thereof;

said process including the step of ring-closing a compound of formula (III):

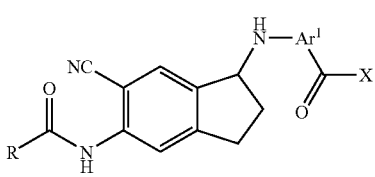

(III)

wherein R and $Ar^1$ are as defined above and X is an alkoxy, aryloxy or optionally substituted amino group; or a protected derivative thereof;

to form a compound of formula (II):

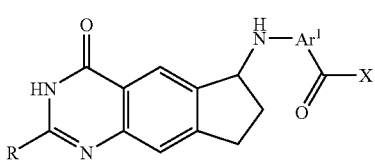

(II)

wherein R and $Ar^1$ are as defined above and X is an alkoxy, aryloxy or optionally substituted amino group; or a protected derivative thereof.

8. A process as claimed in claim 7 wherein the reaction is carried out in basic conditions in the presence of hydrogen peroxide.

9. A process as claimed in claim 2 wherein X is a residue of an aliphatic alcohol of up to 6 carbon.

10. A process as claimed in claim 2 wherein:

R is $C_{1-4}$ alkyl, $C_{2-4}$ alkenyl, $C_{2-4}$ alkynyl or a group $A(CH_2)_p$, wherein $R^0$ and $R^1$ are each independently hydrogen or $C_{1-4}$ alkyl; and $Ar^1$ is 1,4-phenylene which may optionally bear one or two substituents selected from the group consisting of chloro, fluoro, thiophene-2,5-diyl, thiazole-2,5-diyl and pyridine-2,5-diyl.

11. A process as claimed in claim 2 wherein p is 1.

12. A process as claimed in claim 2 wherein the cyclopenta[g]quinazoline of formula (I) or ester or amide thereof is further reacted to prepare a cyclopenta[g]quinazoline of formula (VI):

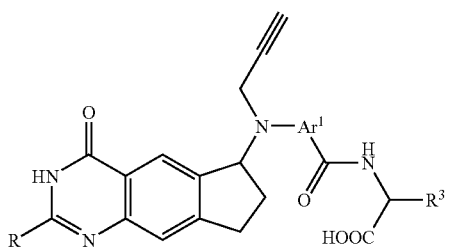

(VI)

wherein A and $Ar^1$ are as defined above, and $R^3$ is a group of the formula:

—$A^5$—CON(R)CH($Y^4$)$Y^5$ in which $A^5$ is a $C_{1-6}$ alkylene group and R is hydrogen, $C_{1-4}$ alkyl, $C_{3-4}$ alkenyl or $C_{3-4}$ alkynyl;

$Y^4$ is carboxy, tetrazol-5-yl, N-($C_{1-4}$ alkylsulfonyl)carbamoyl, N-(pheny-sulfonyl)-carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl; and $Y^5$ is the residue of a naturally occurring amino acid $NH_2CH(CO_2H)Y^5$; or $Y^5$ is a group of the formula:

—$A^4$—$CO_2H$ in which $A^4$ is a $C_{2-6}$ alkylene group; or $Y^5$ is a group of the formula:

—$A^6$—$Ar^3$—$A^7$—$Y^6$ in which $A^6$ is a bond between the a-carbon atom of the group —$A^5$—CON(R)CH($Y^4$)— and $Ar^3$ or is a $C_{1-2}$ alkylene group;

$Ar^3$ is phenylene, tetrazolediyl, thiophenediyl, thiazolediyl, pyridinediyl or pyrimidinediyl which in the case of phenylene may optionally bear one or two substituents on the ring selected from halogeno, nitro, $C_{1-4}$ alkyl and $C_{1-4}$ alkoxy;

$A^7$ is a $C_{1-3}$ alkylene or $C_{2-3}$ alkenylene group; and $Y^6$ is carboxy, tetrazol-5-yl, N-($C_{1-4}$ alkylsulfonyl)carbamoyl, N-(phenyl-sulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl;

the compound (VI) optionally being in the form of a pharmaceutically acceptable salt or ester.

13. A process as claimed in claim 7 wherein X is a residue of an aliphatic alcohol of up to 6 carbon.

14. A process as claimed in claim 7 wherein:

R is $C_{1-4}$ alkyl, $C_{2-4}$ alkenyl, $C_{2-4}$ alkynyl or a group $A(CH_2)_p$, wherein $R^0$ and $R^1$ are each independently hydrogen or $C_{1-4}$ alkyl; and Ar¹ is 1,4-phenylene which may optionally bear one or two substituents selected from the group consisting of chloro, fluoro, thiophene-2,5-diyl, thiazole-2,5-diyl and pyridine-2,5-diyl.

15. A process as claimed in claim 7 wherein p is 1.

16. A process as claimed in claim 7 wherein the cyclopenta[g]quinazoline of formula (I) or ester or amide thereof is further reacted to prepare a cyclopenta[g]quinazoline of formula (VI):

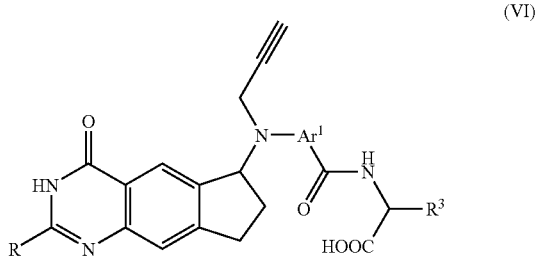

(VI)

wherein A and Ar¹ are as defined above, and $R^3$ is a group of the formula:

—$A^5$—CON(R)CH($Y^4$)$Y^5$ in which $A^5$ is a $C_{1-6}$ alkylene group and R is hydrogen, $C_{1-4}$ alkyl, $C_{3-4}$ alkenyl or $C_{3-4}$ alkynyl;

$Y^4$ is carboxy, tetrazol-5-yl, N-($C_{1-4}$ alkylsulfonyl)carbamoyl, N-(pheny-sulfonyl)-carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl; and $Y^5$ is the residue of a naturally occurring amino acid $NH_2CH(CO_2H)Y^5$; or $Y^5$ is a group of the formula:

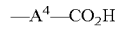

—$A^4$—$CO_2H$ in which $A^4$ is a $C_{2-6}$ alkylene group; or $Y^5$ is a group of the formula:

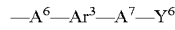

—$A^6$—$Ar^3$—$A^7$—$Y^6$ in which $A^6$ is a bond between the α-carbon atom of the group —$A^5$—CON(R)CH($Y^4$)— and $Ar^3$ or is a $C_{1-2}$ alkylene group;

$Ar^3$ is phenylene, tetrazolediyl, thiophenediyl, thiazolediyl, pyridinediyl or pyrimidinediyl which in the case of phenylene may optionally bear one or two substituents on the ring selected from halogeno, nitro, $C_{1-4}$ alkyl and $C_{1-4}$ alkoxy;

$A^7$ is a $C_{1-3}$ alkylene or $C_{2-3}$ alkenylene group; and $Y^6$ is carboxy, tetrazol-5-yl, N-($C_{1-4}$ alkylsulfonyl)carbamoyl, N-(phenyl-sulfonyl)carbamoyl which may optionally bear one or two substituents on the phenyl ring selected from the group consisting of halogeno, nitro, $C_{1-4}$ alkyl and $C_{1-4}$ alkoxy, tetrazol-5-ylthio, tetrazol-5-ylsulfinyl or tetrazol-5-ylsulfonyl;

the compound (VI) optionally being in the form of a pharmaceutically acceptable salt or ester.

* * * * *

UNITED STATES PATENT AND TRADEMARK OFFICE
CERTIFICATE OF CORRECTION

PATENT NO. : 7,250,511 B2
APPLICATION NO. : 10/487863
DATED : July 31, 2007
INVENTOR(S) : Vassilios Bavetsias It is certified that error appears in the above-identified patent and that said Letters Patent is hereby corrected as shown below:

Column 1, lines 9, 10: please amend "cyclopenta[g]-quinazoline" to read "cyclopenta[g]quinazoline".

Column 1, line 62: please amend "cyclopenta[g]quinazoline-compounds" to read "cyclopenta[g]quinazoline compounds".

Column 3, line 35: please amend "cyclopenta[g]-quinazoline" to read "cyclopenta[g]quinazoline".

Column 6, line 60: please amend "Cyclopenta[g]quinazolines" to read "cyclopenta[g]quinazolines".

Column 8, line 12: please amend "Cyclopenta[g]quinazoline" to read "cyclopenta[g]quinazoline".

Column 8, line 18: please delete "8" before "British".

Column 8, line 62: please amend "benzyl-oxycarbonyl" to read "benzyloxycarbonyl".

Column 10, line 62: please amend "Cyclopenta[g]quinazoline" to read "cyclopenta[g]quinazoline".

Column 12, line 58: please amend "m/z )ESI)" to read "m/z (ESI)".

Column 13, line 22: please amend "2-Methyl4-oxo" to read "2-Methyl-4-oxo".

Column 13, line 23: please amend "cyclopenta-[g]" to read "cyclopenta[g]".

Column 14, line 21: please amend "cyclopenta-[g]" to read "cyclopenta[g]".

Column 15, line 38: please amend "Methoxymethyl4oxo" to read "Methoxymethyl-4-oxo".

Column 15, line 39: please amend "pent[g]" to read "penta[g]".

Column 16, line 1: please amend "$Na_2SO4$" to read "$Na_2SO_4$".

Column 16, line 6: please amend "400" to read "4.00".

UNITED STATES PATENT AND TRADEMARK OFFICE
CERTIFICATE OF CORRECTION

PATENT NO.       : 7,250,511 B2
APPLICATION NO.  : 10/487863
DATED            : July 31, 2007
INVENTOR(S)      : Vassilios Bavetsias It is certified that error appears in the above-identified patent and that said Letters Patent is hereby corrected as shown below:

Column 16, line 13: please amend "6bromoindan" to read "6-bromoindan".

Column 16, line 66: please amend "amido6-bromo" to read "amido-6-bromo".

Column 17, line 10: please amend "5-acetamido6-bromo" to read "5-methoxyacetamido-6-bromo".

Column 17, line 51: please amend "anhydrou" to read "anhydrous".

Column 18, line 34, column 19, line 1, and column 19, line 54: please amend "methoxymethyl4-oxo" to read "methoxymethyl-4-oxo".

Column 19, line 6: please amend "dichloro-methane" to read "dichloromethane".

Column 19, line 58, and column 20, line 11: please amend "tetra-hydro" to read "tetrahydro".

Column 20, line 17: please amend "trifluoro-acetate" to read "trifluoroacetate".

Column 20, line 21: please amend "0.35 inmol" to read "0.35 mmol".

Column 20, line 50: please amend "cyclo-penta[g]quinazhn-6yl" to read "cyclopenta[g]quinazolin-6-yl".

Column 20, line 55: please amend "oxymethyl4-oxo" to read "oxymethyl-4-oxo".

Column 20, line 66: please amend "DMSO-hd6" to read "DMSO-$d_6$".

Column 21, line 40: please amend "2chloromethyl" to read "2-chloromethyl".

Column 21, line 41: please amend "Jaclinan" to read "Jackman".

Column 21, line 42: please amend "DA" to read "DMF".

Column 21, line 58: please amend "RRMS" to read "HRMS".

Column 21, line 62: please amend "cyclopenta-[g]quinazolin4one" to read "cyclopenta[g]quinazolin-4-one".

UNITED STATES PATENT AND TRADEMARK OFFICE
CERTIFICATE OF CORRECTION

PATENT NO.        : 7,250,511 B2
APPLICATION NO. : 10/487863
DATED             : July 31, 2007
INVENTOR(S)       : Vassilios Bavetsias It is certified that error appears in the above-identified patent and that said Letters Patent is hereby corrected as shown below:

Column 22, line 15: please amend "(+H)$^+$" to read "(M+H)$^+$".

Column 22, line 15: please amend "HMS" to read "HRMS".

Column 22, line 33: please amend "oxymethyo" to read "oxymethyl".

Column 22, line 34: please amend "tetrahydro6H" to read "tetrahydro-6H".

Column 22, line 34: please amend "cyclopenta-[g]" to read "cyclopenta[g]".

Column 22, line 36: please amend "tetra-hydro" to read "tetrahydro".

Column 23, line 20: please amend "FAB, mz" to read "FAB, m/z".

Column 24, line 5: please amend "methyl)4-oxo" to read "methyl)-4-oxo".

Column 24, line 6: please amend "tetra-hydro" to read "tetrahydro".

Column 24, line 30: please amend "methyl)4-oxo" to read "methyl)-4-oxo".

Column 24, line 34: please amend "cyano-phosphonate" to read "cyanophosphonate".

Column 24, line 61: please amend "cyclo-penta" to read "cyclopenta".

Column 25, line 2: please amend "trifluoro-acetic" to read "trifluoroacetic".

Column 25, line 27: please amend "tetra-hydro-6H-cyclopental" to read "tetrahydro-6H-cyclopenta".

Column 26, line 50: please amend "aminio" to read "amino".

Column 26, line 50: please amend "cyclopenta-[g]" to read "cyclopenta[g]".

Column 27, line 19: please amend "cyclopenta-[g]" to read "cyclopenta[g]".

Column 27, line 23: please amend "(Propargyl)" to read "(propargyl)".

Column 28, line 1: please amend "N-[(6RS)" to read "4-{N-[(6RS)".

UNITED STATES PATENT AND TRADEMARK OFFICE
CERTIFICATE OF CORRECTION

PATENT NO. : 7,250,511 B2
APPLICATION NO. : 10/487863
DATED : July 31, 2007
INVENTOR(S) : Vassilios Bavetsias It is certified that error appears in the above-identified patent and that said Letters Patent is hereby corrected as shown below:

Column 28, line 1: please amend "4oxo" to read "4-oxo".

Column 28, line 35: please amend "tri-ethyl-amine" to read "triethylamine".

Column 28, line 64: please amend "tetra-hydro" to read "tetrahydro".

Column 29, line 24: please amend "lin-6yl" to read "lin-6-yl".

Column 29, line 47: please amend "dimethyl-propionyl" to read "dimethylpropionyl".

Column 30, line 17: please amend "ethyl4-oxo-3,4,7,8-tetra-hydro" to read "ethyl-4-oxo-3,4,7,8-tetrahydro".

Column 30, line 54: please amend "dichloro-methane" to read "dichloromethane.".

Column 31, line 1: please amend "2-hydroxymethyl-4oxo" to read "2-hydroxymethyl-4-oxo".

Column 31, line 2: please amend "cyclo-penta" to read "cyclopenta".

Column 32, line 27: please amend "-6bro-" to read "-6-bro-".

Column 32, line 60: please amend "$C_{29}H_{31},BrN_2O_4$" to read "$C_{29}H_{31}BrN_2O_4$".

Column 33, line 19: please amend "Na2SO$_4$" to read "Na$_2$SO$_4$".

Column 33, line 38: please amend "2-benzyloxy-ethanoylamino" to read "2-benzyloxyethanoylamino".

Column 35, line 11: please amend "benzoate acid" to read "benzoic acid".

Column 43/44: please amend the second structure from bottom so that, at the 2-position, the carbonyl is attached to the ring via a OCH$_2$, as in the last structure. Please delete the second reaction arrow.

UNITED STATES PATENT AND TRADEMARK OFFICE
CERTIFICATE OF CORRECTION

PATENT NO. : 7,250,511 B2  
APPLICATION NO. : 10/487863  
DATED : July 31, 2007  
INVENTOR(S) : Vassilios Bavetsias It is certified that error appears in the above-identified patent and that said Letters Patent is hereby corrected as shown below:

Column 45/46: please insert --Scheme 4-- between second and third structure from bottom.

Column 58, line 64: please insert --wherein R, $Ar^1$ and X are as defined in claim 1-- after the structure.

Column 60, line 30: please amend "pheny-sulfonyl" to read "phenylsulfonyl".

Column 60, line 44: please amend "a-carbon" to read "α-carbon".

Signed and Sealed this

Sixteenth Day of June, 2009

JOHN DOLL  
*Acting Director of the United States Patent and Trademark Office*